US012179018B2

(12) United States Patent
Athos et al.

(10) Patent No.: US 12,179,018 B2
(45) Date of Patent: Dec. 31, 2024

(54) PULSE GENERATOR WITH INDEPENDENT PANEL TRIGGERING

(71) Applicant: Pulse Biosciences, Inc., Hayward, CA (US)

(72) Inventors: Brian G. Athos, San Francisco, CA (US); Shu Xiao, Norfolk, VA (US); David J. Danitz, San Jose, CA (US); Mark P. Kreis, San Francisco, CA (US); Darrin R. Uecker, San Mateo, CA (US)

(73) Assignee: Pulse Biosciences, Inc., Hayward, CA (US)

( * ) Notice: Subject to any disclaimer, the term of this patent is extended or adjusted under 35 U.S.C. 154(b) by 646 days.

(21) Appl. No.: 17/158,325

(22) Filed: Jan. 26, 2021

(65) Prior Publication Data

US 2021/0146129 A1 May 20, 2021

Related U.S. Application Data

(62) Division of application No. 15/444,738, filed on Feb. 28, 2017, now Pat. No. 10,946,193.

(51) Int. Cl.
*A61N 1/36* (2006.01)
*A61B 18/12* (2006.01)
(Continued)

(52) U.S. Cl.
CPC ............ *A61N 1/36* (2013.01); *A61B 18/1206* (2013.01); *A61N 1/04* (2013.01); *A61N 1/32* (2013.01);
(Continued)

(58) Field of Classification Search
None
See application file for complete search history.

(56) References Cited

U.S. PATENT DOCUMENTS 4,575,671 A * 3/1986 Lee ........................... H02J 3/40
322/29
5,568,035 A 10/1996 Kato et al.
(Continued)

FOREIGN PATENT DOCUMENTS

WO 2011146498 A2 11/2011
WO 2014060854 A1 4/2014
(Continued)

OTHER PUBLICATIONS

PCT/US2018/019213, Preliminary Report on Patentability, mailed Sep. 12, 2019, 9 pages.
(Continued)

*Primary Examiner* — Erica S Lee

(57) ABSTRACT

A pulse generation system is disclosed. The pulse generation system includes a controller, an output terminal, and a plurality of pulse generator circuits. The controller is configured to cause a driving signal pulse to be transmitted to any selected one or more of the pulse generator circuits, and to cause the driving signal pulse to not be transmitted to any selected one or more other pulse generator circuits. Each of the pulse generator circuits is configured to generate an output voltage pulse at the output terminal in response to the driving signal pulse being transmitted thereto.

28 Claims, 29 Drawing Sheets

(51) Int. Cl.

| | | |
|---|---|---|
| *A61N 1/04* | (2006.01) | |
| *A61N 1/32* | (2006.01) | |
| *A61N 1/39* | (2006.01) | |
| *H03K 3/53* | (2006.01) | |
| *H03K 3/57* | (2006.01) | |
| *H03K 3/64* | (2006.01) | |

(52) U.S. Cl.
CPC ..... *A61N 1/36125* (2013.01); *A61N 1/36142* (2013.01); *A61N 1/3912* (2013.01); *H03K 3/53* (2013.01); *H03K 3/57* (2013.01); *H03K 3/64* (2013.01); *A61B 2018/1273* (2013.01)

(56) References Cited

U.S. PATENT DOCUMENTS

| | | | |
|---|---|---|---|
| 5,635,776 | A | 6/1997 | Imi |
| 5,774,348 | A | 6/1998 | Druce et al. |
| 5,902,272 | A | 5/1999 | Eggers et al. |
| 5,907,484 | A | 5/1999 | Kowshik et al. |
| 6,008,690 | A | 12/1999 | Takeshima et al. |
| 6,017,354 | A | 1/2000 | Culp et al. |
| 6,026,003 | A | 2/2000 | Moore et al. |
| 6,048,789 | A | 4/2000 | Vines et al. |
| 6,137,276 | A | 10/2000 | Rudolph |
| 6,190,381 | B1 | 2/2001 | Olsen et al. |
| 6,326,177 | B1 | 12/2001 | SchoentJach et al. |
| 6,831,377 | B2 | 12/2004 | Yampolsky et al. |
| 7,496,401 | B2 | 2/2009 | Bernabei |
| 7,767,433 | B2 | 8/2010 | Kuthi et al. |
| 7,855,904 | B2 | 12/2010 | Kirbie et al. |
| 7,937,143 | B2 | 5/2011 | Demarais et al. |
| 8,000,813 | B2 | 8/2011 | Schoenbach et al. |
| 8,216,224 | B2 | 7/2012 | Morris et al. |
| 8,512,334 | B2 | 8/2013 | Nuccitelli et al. |
| 8,688,227 | B2 | 4/2014 | Nuccitelli et al. |
| 8,822,222 | B2 | 9/2014 | Beebe et al. |
| 9,101,337 | B2 | 8/2015 | Hoegerle et al. |
| 9,101,764 | B2 | 8/2015 | Nuccitelli et al. |
| 9,724,155 | B2 | 8/2017 | Nuccitelli et al. |
| 2001/0025177 | A1 | 9/2001 | Woloszko et al. |
| 2002/0193833 | A1 | 12/2002 | Dimmer et al. |
| 2003/0204161 | A1 | 10/2003 | Ferek-Petric |
| 2003/0233087 | A1 | 12/2003 | Chen et al. |
| 2004/0080964 | A1 | 4/2004 | Buchmann |
| 2004/0240241 | A1 | 12/2004 | Chueh et al. |
| 2006/0020297 | A1* | 1/2006 | Gerber ............... A61N 1/36071 607/39 |
| 2006/0062074 | A1 | 3/2006 | Gundersen et al. |
| 2006/0079886 | A1 | 4/2006 | Orszulak et al. |
| 2006/0090723 | A1 | 5/2006 | Stuart |
| 2006/0139977 | A1 | 6/2006 | Oicles et al. |
| 2007/0066957 | A1 | 3/2007 | Demarais et al. |
| 2007/0129626 | A1 | 6/2007 | Mahesh et al. |
| 2007/0135755 | A1 | 6/2007 | Bernabei |
| 2008/0077189 | A1 | 3/2008 | Ostroff et al. |
| 2008/0169846 | A1 | 7/2008 | Lan et al. |
| 2008/0031337 | A1 | 9/2008 | Krishnaswamy et al. |
| 2009/0198231 | A1 | 8/2009 | Esser et al. |
| 2009/0299362 | A1 | 12/2009 | Long et al. |
| 2010/0038971 | A1 | 2/2010 | Sanders et al. |
| 2010/0042095 | A1 | 2/2010 | Bigley et al. |
| 2010/0063496 | A1 | 3/2010 | Trovato et al. |
| 2010/0086009 | A1 | 4/2010 | Han |
| 2010/0240995 | A1 | 9/2010 | Nuccitelli |
| 2010/0318082 | A1 | 12/2010 | Nuccitelli et al. |
| 2010/0331758 | A1 | 12/2010 | Davalos et al. |
| 2011/0015630 | A1 | 1/2011 | Azure |
| 2011/0092973 | A1 | 4/2011 | Nuccitelli et al. |
| 2011/0118729 | A1 | 5/2011 | Heeren et al. |
| 2011/0144641 | A1 | 6/2011 | Dimalanta et al. |
| 2011/0160514 | A1 | 6/2011 | Long et al. |
| 2011/0270249 | A1 | 11/2011 | Utley et al. |
| 2012/0277763 | A1 | 11/2012 | Greenblatt et al. |
| 2012/0310095 | A1 | 12/2012 | Sato |
| 2012/0310230 | A1 | 12/2012 | Willis et al. |
| 2012/0315704 | A1 | 12/2012 | Beebe et al. |
| 2013/0018441 | A1 | 1/2013 | Childs |
| 2013/0060246 | A1 | 3/2013 | Knopp et al. |
| 2013/0150935 | A1 | 6/2013 | Weissberg et al. |
| 2013/0302409 | A1 | 11/2013 | Fuchs et al. |
| 2013/0345697 | A1 | 12/2013 | Fuchs et al. |
| 2014/0046322 | A1 | 2/2014 | Callas et al. |
| 2014/0081256 | A1 | 3/2014 | Carmel et al. |
| 2014/0228835 | A1 | 8/2014 | Mielekamp et al. |
| 2014/0277219 | A1 | 9/2014 | Nanda |
| 2014/0336638 | A1 | 11/2014 | Deem et al. |
| 2014/0358066 | A1 | 12/2014 | Nuccitelli et al. |
| 2014/0364797 | A1 | 12/2014 | Schoenbach et al. |
| 2015/0032100 | A1 | 1/2015 | Coulson et al. |
| 2015/0065946 | A1 | 3/2015 | Gehl et al. |
| 2015/0201991 | A1 | 7/2015 | Zemlin |
| 2015/0272657 | A1 | 10/2015 | Yates et al. |
| 2016/0157932 | A1 | 6/2016 | Nuccitelli et al. |
| 2017/0245928 | A1 | 8/2017 | Xiao et al. |
| 2017/0246455 | A1 | 8/2017 | Athos et al. |
| 2017/0319851 | A1 | 11/2017 | Athos et al. |
| 2017/0326361 | A1 | 11/2017 | Kreis |
| 2017/0360504 | A1 | 12/2017 | Nuccitelli et al. |
| 2018/0078755 | A1 | 3/2018 | Kreis |
| 2018/0110557 | A1 | 4/2018 | Muratori et al. |
| 2018/0154142 | A1 | 6/2018 | Guo et al. |
| 2019/0046791 | A1 | 2/2019 | Ebbers et al. |
| 2019/0217080 | A1 | 7/2019 | Moss et al. |

FOREIGN PATENT DOCUMENTS

| | | |
|---|---|---|
| WO | 2016089781 A1 | 6/2016 |
| WO | 2017/151260 A1 | 9/2017 |
| WO | 2017/151261 A1 | 9/2017 |
| WO | 2017200954 A1 | 11/2017 |
| WO | 2017201394 A1 | 11/2017 |
| WO | 2018053539 A1 | 3/2018 |
| WO | 2018075946 A1 | 4/2018 |
| WO | 2018089506 A1 | 5/2018 |

OTHER PUBLICATIONS

PCT/US2017/015881, "International Search Report and Written Opinion" mailed May 25, 2017, 13 pages.
Carey et al., "Marx Generator Design and Performance," Applied Physical Electronics, L.C., 4 pages.
Redondo et al., "Solid-State Marx Generator Design with an Energy Recovery Reset Circuit for Output Transformer Association," Power Electronics Specialists Conference, IEEE, 2007, 5 pages.
Harshada C. Bhosale et al., "Design and Simulation of 50 kV, 50 A Solid State Marx Generator," International Conference on Magnetics, Machines & Drives (AICERA—2014 ICMMD), IEEE 2014, pp. 1-5.
Martin Sack et al. "Design Considerations for a Fast Stacked-MOSFET Switch," IEEE Transactions on Plasma Science, vol. 41, No. 10, Oct. 20-13, pp. 2630-2636.
Chenguo Yao et al., "FPGA-Controlled All-Solid-State Nanosecond Pulse Generator for Biological Applications," IEEE Transactions on Plasma Science, vol. 40, No. 10, Oct. 2012, pp. 2366-2372.
W.Jiang et al., "Marx Generator Using Power Mosfets," IEEE 2009, pp. 408-410.
Anand et al., "Adaptive Immune Response to Nano-Pulse Stimulation (NPS), Nov. 11, 2016, Poster presentation at the 31st Annual Meeting and Associated Programs of the Society for Immunotherapy of Cancer," Retrieved from the Internet: URL: http://pulsebiosciences.com/assets/Pulse%20AIR%20poster.pdf, retrieved on Mar. 13, 2018.
Anand et al., "Nano-Pulse Electro-Signaling treatment of murine tumors significantly reduces the percentage of regulatory T cells in the treated tumor," Journal for Immunotherapy of Cancer: 31 st Annual Meeting and Associated Programs of the Society for Immunotherapy of Cancer (SITC 2016), Part Two, National Harbor, MD, USA Nov. 16, 2016, p. 214.
Beebe, S. J., "Hepatocellular carcinoma ablation and possible immunity in the age of nanosecond pulsed electric fields," Journal of Hepatocellular Carcioma, May 2015, No. 2, pp. 49-55.

(56) References Cited

OTHER PUBLICATIONS

McDaniel et al., "Nanosecond pulsed electric field treatment of tumor cell lines triggers immunogenic cell death (ICD)," Nov. 11, 2016, Poster presentation at the 31st Annual Meeting and Associated Programs of the Society for Immunotherapy of Cancer (SITC 2016), National Harbor, MD, USA; Retrieved from the Internet: URL: http://pulsebiosciences.com/assets/Pulse%20ICD%20poster.pdf, retrieved on Mar. 13, 2018.

McDaniel et al., "P329 Nanosecond pulsed electric field treatment of tumor cell lines triggers immunogenic cell death (ICD)," Journal for Immuno Therapy of Cancer: 31st Annual Meeting and Associated Programs of the Society for Immunotherapy of Cancer (SITC 2016): part two: National Harbor, MD, USA, Nov. 16, 2016, p. 175.

PCT/US2017/057698, "International Search Report" mailed Feb. 27, 2018, 3 pages.

PCT/US2017/064685, "International Search Report" mailed Mar. 22, 2018, 5 pages.

PCT/US2018/019213, "International Search Report" mailed May 22, 2018, 4 pages.

PCT/US2017/060654, "International Search Report and Written Opinion," mailed Feb. 27, 2018, 18 pages.

Garon et al., "In Vitro and In Vivo Evaluation and a Case Report of Intense Nanosecond Pulsed Electric Field as a Local Therapy for Human Malignancies", Int. J. Cancer, vol. 121, 2007, pp. 675-682.

Gundersen et al., "Nanosecond Pulse Generator Using a Fast Recovery Diode", IEEE 26.sup.th Power Modulator Conference, 2004, pp. 603-606.

International Application No. PCT/US2015/63025, International Search Report and Written Opinion dated Apr. 21, 2016, 9 pages.

Nader Yatim et al., "RIPK1 and NF-1 kappa.B signaling in dying cells determines cross-priming of CD8.sup+ T cells," Science, Oct. 2015, vol. 350, Issue 6258, pp. 328-335, sciencemag.org.

PCT/US2017/052340, "International Search Report and Written Opinion", Jan. 8, 2018, 12 pages.

Tang et al., "Diode Opening Switch Based Nanosecond High Voltage Pulse Generators for Biological and Medical Applications", IEEE Transactions on Dielectrics and Electrical Insulation, vol. 14, No. 4, 2007, pp. 878-883.

Wang et al., "Solid-State High Voltage Nanosecond Pulse Generator," IEEE Pulsed Power Conference, 2005, pp. 1199-1202.

PCT/US2017//032744, "International Search Report and Written Opinion," mailed Jul. 21, 2017, 11 pages.

PCT/US2017/015884, "International Search Report and Written Opinion" mailed Apr. 21, 2017, 12 pages.

International Application No. PCT/US2017/015881, Invitation to Pay Additional Fees and, Where Applicable, Protest Fee, mailed Mar. 15, 2017, 2 pages.

R. J. Baker et al., "Stacking Power MOSFETs for use in High Speed Instrumentation," Rev. Sci. Instrum. 63 (12), Dec. 1992. pp. 5799-5801, vol. 63, No. 12, American Institute of Physics.

H. Kirbie et al., "An All Solid State Pulse Power Source for High PRF Induction Acceslerators," IEEE 1998, pp. 6-11.

K. Okamura et al., "Development of the High Repetitive Impulse Voltage Generator Using Semiconductor Switches," IEEE 1999, pp. 807-810.

A. Krasnykh et al., "A Solid State Marx Type Modulator for Driving a TWT" Conference Record of the 24th, International Power Modulator Sypolsium 2000, pp. 209-211.

R.J. Richter-Sand et al., "Marx-Stacked IGBT Modulators for High Voltage, High Power Applications," IEEE 2002, pp. 390-393.

Marcel P.J. Gaudreau et al., "Solid-State Pulsed Power Systems for the Next linear Collider," IEEE 2002. pp. 298-301.

Cook et al., "Design and Testing of a Fast, 50 kV Solid-State Kicker Pulser," IEEE 2002. pp. 106-109.

Jeffrey A. Casey et al., "Solid-State Marx Bank Modulator for the Next Generation Linear Collider," Conference Record of the 26.sup.th International Power Modulator Symposium and 2004 High Voltage Workshop {PMC), San Francisco, California. May 23-26, 2004, IEEE 2004, pp. 257-260.

\* cited by examiner

PULSE GENERATOR WITH INDEPENDENT PANEL TRIGGERING

RELATED APPLICATIONS

Pursuant to 35 U.S.C. § 121, this application claims priority to and is a divisional of U.S. patent application Ser. No. 15/444,738, filed Feb. 28, 2017, entitled "PULSE GENERATOR WITH INDEPENDENT PANEL TRIGGERING," issued as U.S. Pat. No. 10,946,193 on Mar. 16, 2021, which is incorporated by reference herein in its entirety for all purposes.

BACKGROUND

1. Field of the Invention

The present application generally relates to high voltage pulse generators for applying high voltage electrical pulses to patients. Specifically, using multiple panels to generate the pulses, where the panels may be triggered independently.

2. Description of the Related Art

Surgical excision of a tumor can result in an infection and leave a scar. Furthermore, if there are more tumors, every cancerous tumor should be identified and individually excised by a surgeon. This can be time consuming and expensive, not to mention uncomfortable for patients.

Cancerous tumors that are internal to a patient may be especially difficult to remove, let alone detect and treat. Many patients' lives are turned upside down by the discovery of cancer in their bodies, sometimes which have formed relatively large tumors before being detected.

A "nanosecond pulsed electric field," sometimes abbreviated as nsPEF, includes an electric field with a sub-microsecond pulse width of between 0.1 nanoseconds (ns) and 1000 nanoseconds, or as otherwise known in the art. It is sometimes referred to as sub-microsecond pulsed electric field. NsPEFs often have high peak voltages, such as 10 kilovolts per centimeter (kV/cm), 20 kV/cm, to 500 kV/cm. Treatment of biological cells with nsPEF technology often uses a multitude of periodic pulses at a frequency ranging from 0.1 per second (Hz) to 10,000 Hz.

NsPEFs have been found to trigger apoptosis in cancerous tumors. Selective treatment of such tumors with nsPEFs can induce apoptosis within the tumor cells without substantially affecting normal cells in the surrounding tissue due to its non-thermal nature.

An example of nsPEF applied to biological cells is shown and described in U.S. Pat. No. 6,326,177 (to Schoenbach et al.), which is incorporated herein by reference in its entirety for all purposes.

The use of nsPEF for the treatment of tumors is a relatively new field. There exists a need for electrodes to deliver nsPEF pulses generated by a pulse generator to patients with minimal distortion and with maximum utility and safety.

BRIEF SUMMARY

Some inventive aspects include pulse generation systems which have individually exercisable portions, such as one or more pulse generators of a plurality of pulse generators. The exercised portions collectively generate a pulse, which may be delivered to a patient, while the unexercised portions do not participate in generating the pulse.

One inventive aspect is a pulse generation system. The pulse generation system includes a controller, an output terminal, and a plurality of pulse generator circuits. The controller is configured to cause a driving signal pulse to be transmitted to any selected one or more of the pulse generator circuits, and to cause the driving signal pulse to not be transmitted to any selected one or more other pulse generator circuits. Each of the pulse generator circuits is configured to generate an output voltage pulse at the output terminal in response to the driving signal pulse being transmitted thereto.

In some embodiments, the pulse generation system also includes a driver circuit configured to generate the driving signal pulse, and a plurality of switches each connected between the driver circuit and one of the plurality of pulse generator circuits, where the controller is configured to selectively connect the plurality of pulse generator circuits to the driver circuit with the switches.

In some embodiments, each pulse generator circuit includes a plurality of pulse generator stages configured to cooperatively generate the output voltage pulse in response to the driving signal pulse being transmitted from the driver circuit.

In some embodiments, each pulse generator circuit includes a pulse generator stage driver configured to receive the driving signal pulse from the driver circuit and to generate a signal pulse for the pulse generator stages, and where the pulse generator stages are configured to cooperatively generate the output voltage pulse in response to the signal pulse.

In some embodiments, the pulse generation system also includes a plurality of driver circuits each configured to generate a driving signal pulse for one of the pulse generator circuits in response to a received input pulse, where the controller is configured to cause an input pulse to be transmitted to any selected one or more of the driver circuits, and to cause no input pulse to be transmitted to any selected one or more other driver circuits.

In some embodiments, each pulse generator circuit includes a plurality of pulse generator stages configured to cooperatively generate the output voltage pulse in response to the driving signal pulse being transmitted from one of the driver circuits.

In some embodiments, each pulse generator circuit includes a pulse generator stage driver configured to receive the driving signal pulse from one of the driver circuits and to generate a signal pulse for the pulse generator stages, and where the pulse generator stages are configured to cooperatively generate the output voltage pulse in response to the signal pulse.

In some embodiments, the pulse generation system also includes a plurality of pulse generator stage drivers, each connected to one of the pulse generator stages, where each pulse generator stage driver is configured to generate a signal pulse for the pulse generator stage connected thereto, and where the pulse generator stages are configured to cooperatively generate the output voltage pulse in response to the signal pulses.

In some embodiments, the pulse generation system also includes a plurality of switch drivers, where each pulse generator stage includes a plurality of serially connected switches, where each of the switch drivers is connected to one of the switches, and where each switch driver is configured to generate a pulse for the switch connected thereto, and where the switches are configured to cooperatively generate the output voltage pulse in response to the pulses generated by the switch drivers.

Another inventive aspect is a method of operating a pulse generation system including a plurality of portions, each portion of the plurality of portions configured to generate a pulse, the method including selecting a first portion of the pulse generation system for use, transmitting a first signal to the selected first portion, where one or more unselected portions of the pulse generation system do not receive the transmitted first signal, and in response to receiving the transmitted first signal, generating a first pulse with the selected first portion of the pulse generation system.

In some embodiments, the method also includes receiving a first indication of a current or a voltage of the generated first pulse, and determining whether the selected first portion of the pulse generation system is operational based on the received first indication.

In some embodiments, the method also includes recording whether the selected first portion of the pulse generation system is operational in a memory, selecting a second portion of the pulse generation system for use, transmitting a second signal to the selected second portion, in response to receiving the transmitted second signal, generating a second pulse with the selected second portion of the pulse generation system, receiving a second indication of a current or a voltage of the generated second pulse, determining whether the selected second portion of the pulse generation system is operational based on the received second indication, recording whether the selected second portion of the pulse generation system is operational in the memory, and delivering pulses with one or more portions of the pulse generation system determined to be operational.

In some embodiments, the method also includes determining that the pulse generation system is not operating properly, recording whether the selected first portion of the pulse generation system is operational in a memory, selecting a second portion of the pulse generation system for use, transmitting a second signal to the selected second portion, in response to receiving the transmitted second signal, generating a second pulse with the selected second portion of the pulse generation system, receiving a second indication of a current or a voltage of the generated second pulse, determining whether the selected second portion of the pulse generation system is operational based on the received second indication, recording whether the selected second portion of the pulse generation system is operational in the memory, and taking a corrective action for each of the portions of the pulse generation system determined to be not operational.

In some embodiments, the method also includes connecting an electrode to a load, delivering a pulse from the pulse generation system to the load via the electrode, and determining a value for the load, where the first portion of the pulse generation system selected for use is selected based at least in part on the value of the load.

In some embodiments, the one or more unselected portions do not generate the first pulse.

In some embodiments, the method also includes selecting a second portion of the pulse generation system for use, transmitting a second signal to the selected second portion, and in response to receiving the transmitted second signal, generating a second pulse with the selected second portion of the pulse generation system, where the first pulse generated with the selected first portion of the pulse generation system and the second pulse generated with the selected second portion of the pulse generation system have different voltages.

In some embodiments, the method also includes charging the selected first portion of the pulse generator to a first charge voltage, and charging the selected second portion of the pulse generator to a second charge voltage.

In some embodiments, method also includes the selected first portion of the pulse generator is charged to the first charge voltage while the second pulse is generated with the selected second portion of the pulse generator, and where the selected second portion of the pulse generator is charged to the second charge voltage while the first pulse is generated with the selected first portion of the pulse generator.

Another inventive aspect is a method of operating a pulse generation system configured to deliver a pulse to a load, the system including a plurality of portions, each portion of the plurality of portions configured to generate the pulse or to cooperatively generate the pulse with one or more other portions, the method including based on a value of the load, selecting a number of the portions of the pulse generation system for use, transmitting one or more signals to the selected portions, where one or more unselected portions of the pulse generation system do not receive the transmitted signals, and in response to receiving the transmitted signals, generating a first pulse with the selected portions of the pulse generation system.

In some embodiments, the method also includes determining the value of the load.

In some embodiments, determining the load includes delivering a pulse to the load and dividing the delivered voltage by the delivered current.

In some embodiments, the one or more unselected portions do not generate the first pulse.

DETAILED DESCRIPTION

It has been shown that nsPEF treatments can be used to cause cancerous tumor cells to undergo apoptosis, a programmed cell death. Tests have shown that tumors can shrink to nonexistence after treatment. No drugs may be necessary. It has also been shown that the subject's immune system may be stimulated to attack all similar tumor cells, including those of tumors that are not within the nsPEF-treated tumor.

A "tumor" includes any neoplasm or abnormal, unwanted growth of tissue on or within a subject, or as otherwise known in the art. A tumor can include a collection of one or more cells exhibiting abnormal growth. There are many types of tumors. A malignant tumor is cancerous, a premalignant tumor is precancerous, and a benign tumor is noncancerous. Examples of tumors include a benign prostatic hyperplasia (BPH), uterine fibroid, pancreatic carcinoma, liver carcinoma, kidney carcinoma, colon carcinoma, pre-basal cell carcinoma, and tissue associated with Barrett's esophagus.

A "disease" includes any abnormal condition in or on a subject that is associated with abnormal, uncontrolled growths of tissue, including those that are cancerous, precancerous, and benign, or other diseases as known in the art.

"Apoptosis" of a tumor or cell includes an orderly, programmed cell death, or as otherwise known in the art.

"Immunogenic apoptosis" of a tumor or cell includes a programmed cell death that is followed by an immune system response, or as otherwise known in the art. The immune system response is thought to be engaged when the apoptotic cells express calreticulin or another antigen on their surfaces, which stimulates dendritic cells to engulf, consume, or otherwise commit phagocytosis of the targeted cells leading to the consequent activation of a specific T cell response against the target tumor or cell.

Pulse lengths of between 10 and 900 nanoseconds for nsPEF have been particularly studied to be effective in stimulating an immune response. Pulse lengths of about 100 nanoseconds are of particular interest in that they are long enough to carry sufficient energy to be effective at low pulse numbers but short enough to be effective in the manner desired.

A time of "about" a certain number of nanoseconds includes times within a tolerance of ±1%, 2%, 3%, 4%, 5%, 7.5%, 10%, 15%, 20%, 25% or other percentages, or fixed tolerances, such as ±0.1, ±0.2, ±0.3, ±0.4, ±0.5, ±0.7, ±1.0, ±2.0, ±3.0, ±4.0 ±5.0, ±7.0, ±10, ±15, ±20, ±25, ±30, ±40, ±50, ±75 ns, or other tolerances as acceptable in the art in conformance with the effectivity of the time period.

Immune system biomarkers can be measured before and/or after nsPEF treatment in order to confirm that the immune response has been triggered in a patient. Further, nsPEF treatment can be paired with a CD47-blocking antibody treatment to better train CD8+T cells (i.e., cytotoxic T cells) for attacking the cancer.

Figure 1:
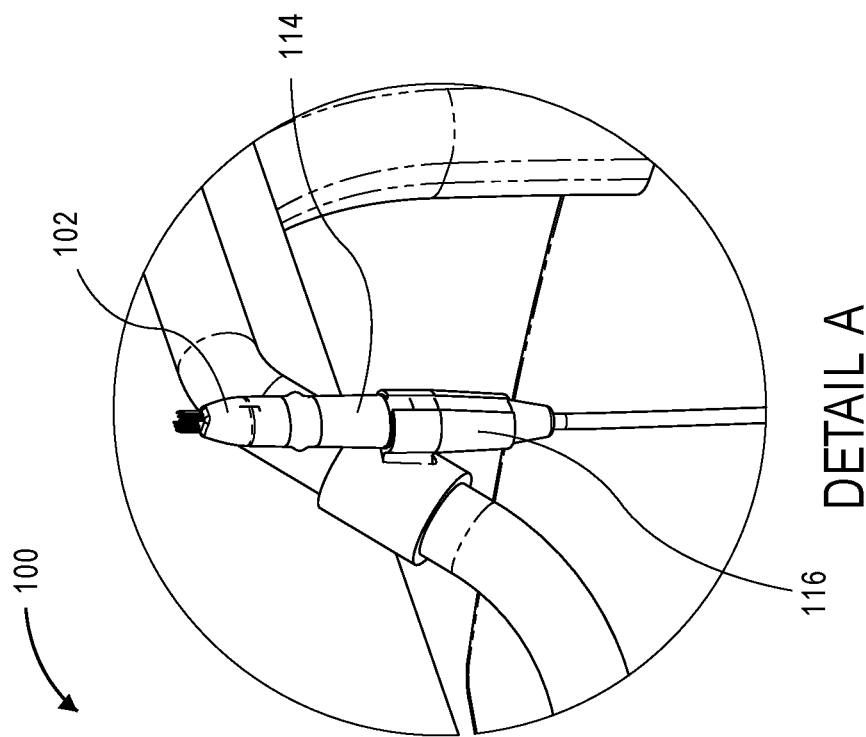
FIG. 1 illustrates a nanosecond pulse generator apparatus in accordance with an embodiment.
Figure 1:
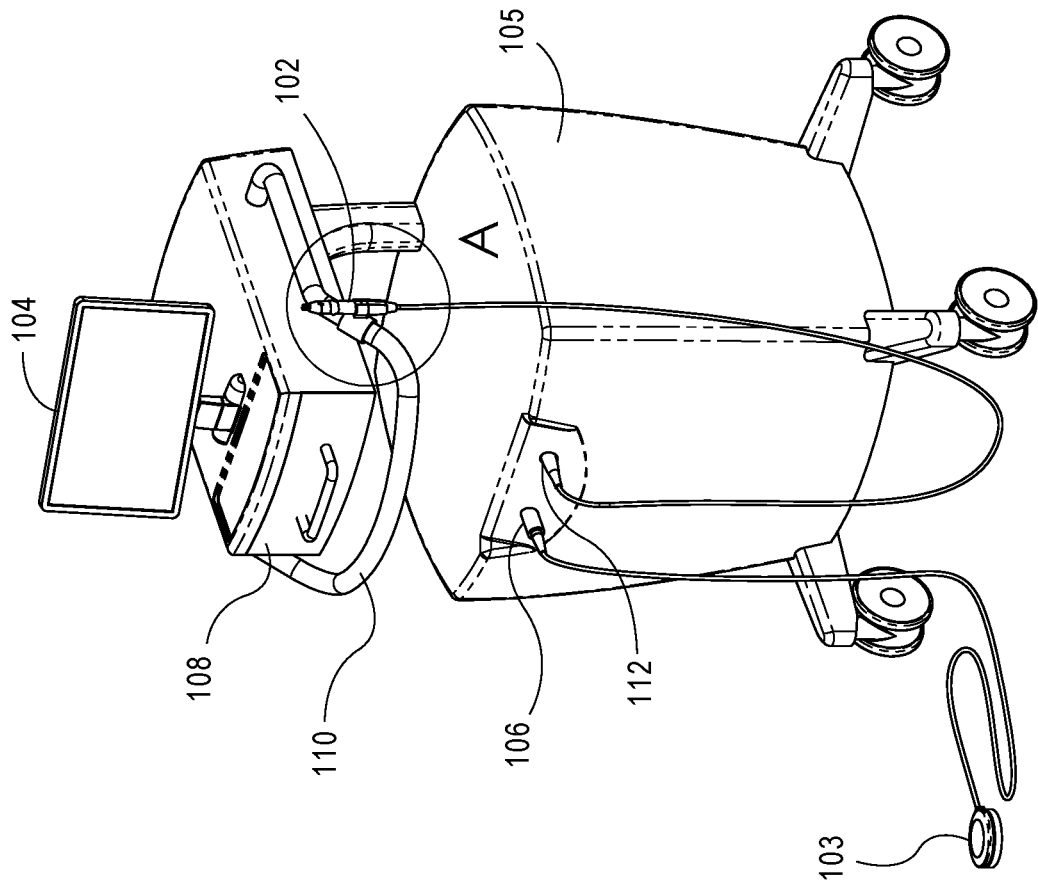

FIG. 1 illustrates a nanosecond pulse generator system in accordance with an embodiment. NsPEF system 100 includes electrode 102, footswitch 103, and interface 104. Footswitch 103 is connected to housing 105 and the electronic components therein through connector 106. Electrode 102 is connected to housing 105 and the electronic components therein through high voltage connector 112. NsPEF system 100 also includes a handle 110 and storage drawer 108. As shown in DETAIL A portion of FIG. 1, nsPEF system 100 also includes holster 116, which is configured to hold electrode 102 at its handle portion 114.

A human operator inputs a number of pulses, amplitude, pulse duration, and frequency information, for example, into a numeric keypad or a touch screen of interface 104. In some embodiments, the pulse width can be varied. A microcontroller sends signals to pulse control elements within nsPEF system 100. In some embodiments, fiber optic cables allow control signaling while also electrically isolating the contents of the metal cabinet with nsPEF generation system 100, the high voltage circuit, from the outside. In order to further isolate the system, system 100 may be battery powered instead of from a wall outlet.

Figure 2:
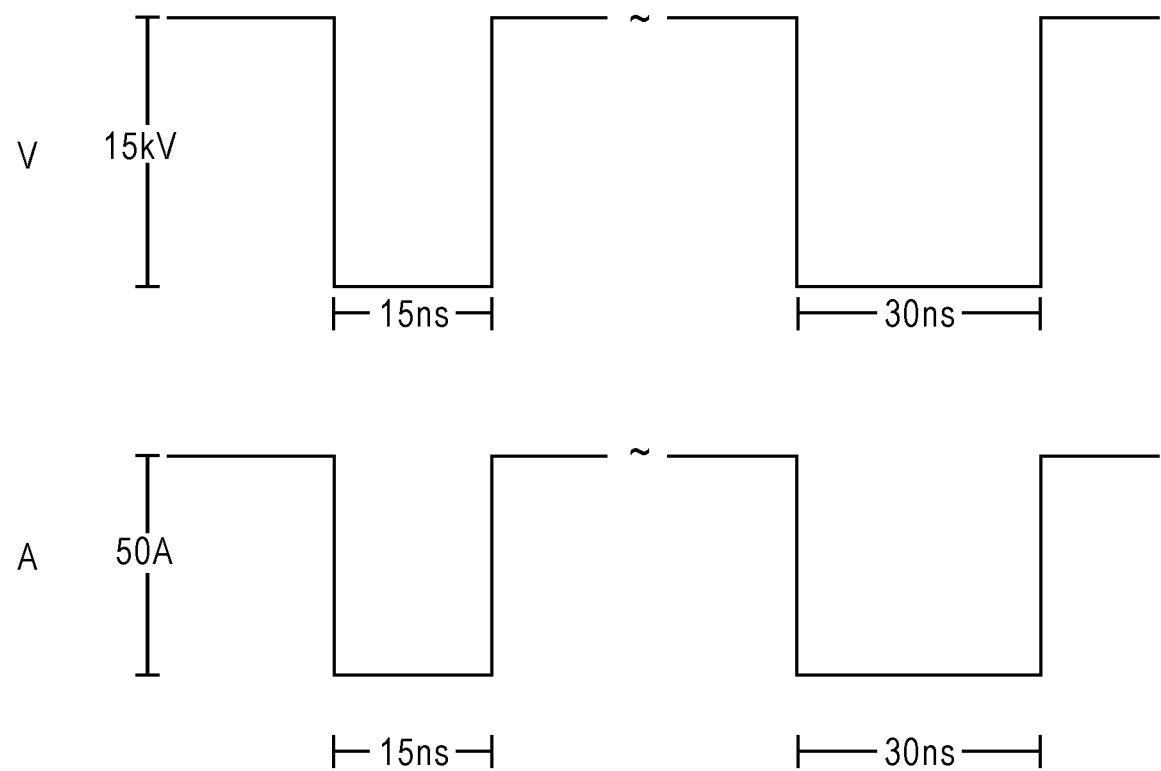
FIG. 2 illustrates a pulse profile for both voltage and current in accordance with an embodiment.

FIG. 2 illustrates a pulse profile for both voltage and current in accordance with an embodiment. Output from the nsPEF system 100 with voltage on the top of the figure and current on the bottom for a first and second pulses. The first pulse has an amplitude of about 15 kV, a current of about 50 A, and a duration of about 15 ns. The second pulse has an amplitude of about 15 kV, a current of about 50 A, and a duration of about 30 ns. Thus, 15 kV may be applied to suction electrodes having 4 mm between the plates so that the tumors experience 47.5 kV/cm, and current between 12 and 50 A. Given a voltage, current depends heavily on the electrode type and tissue resistance.

While FIG. 2 illustrates a specific example, other pulse profiles may also be generated. For example, in some embodiments, rise and/or fall times for pulses may be less than 20 ns, about 20 ns, about 25 ns, about 30 ns, about 40 ns, about 50 ns, about 60 ns, about 75 ns, or greater than 75 ns. In some embodiments, the pulse voltage may be less than 5 kV, about 5 kV, about 10 kV, about 15 kV, about 20 kV, about 25 kV, about 30 kV, or greater than 30 kV. In some embodiments, the current may be less than 10 A, about 10 A, about 25 A, about 40 A, about 50 A, about 60 A, about 75 A, about 100 A, about 125 A, about 150 A, about 175 A, about 200 A, or more than 200 A. In some embodiments, the pulse duration may be less than 10 ns, about 10 ns, about 15 ns, about 20 ns, about 25 ns, about 30 ns, about 40 ns, about 50 ns, about 60 ns, about 75 ns, about 100 ns, about 125 ns, about 150 ns, about 175 ns, about 200 ns, about 300 ns, about 400 ns, about 500 ns, about 750 ns, about 1 μs, about 2 μs, about 3 μs, about 4 μs, about 5 μs, or greater than 5 μs.

Figure 3:
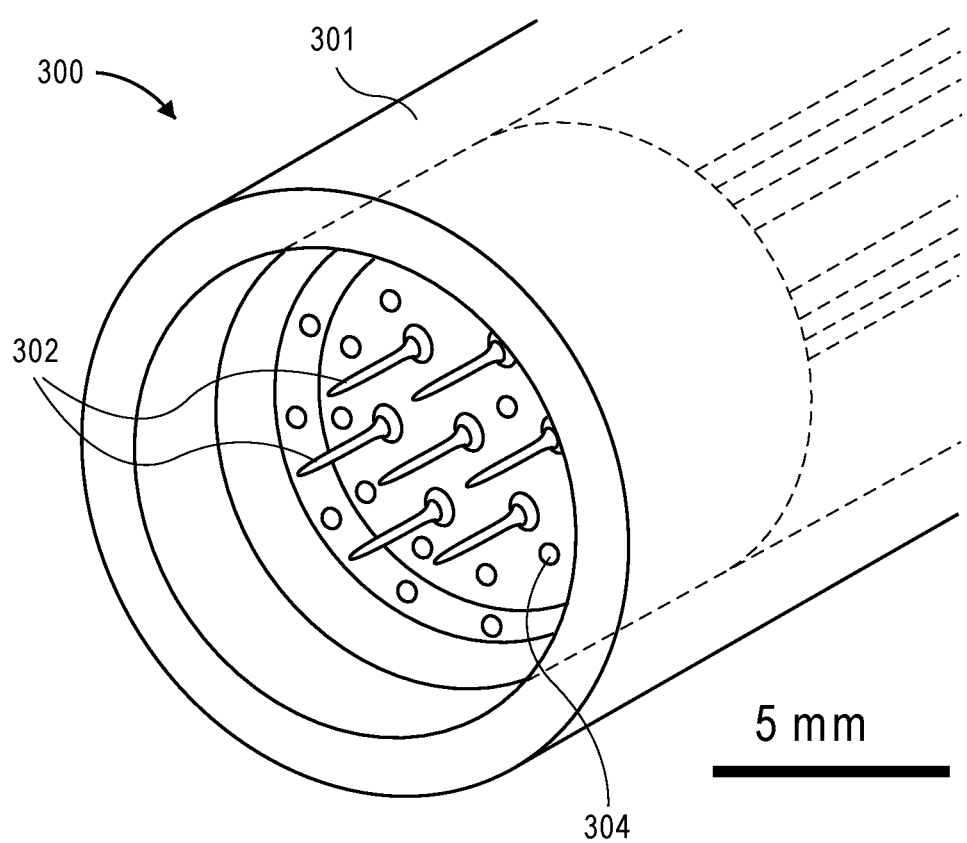
FIG. 3 illustrates a perspective view of a seven-needle electrode in accordance with an embodiment.

FIG. 3 illustrates a perspective view of a seven-needle suction electrode 300 in accordance with an embodiment. In electrode 300, sheath 301 surrounds seven sharp terminals 302 with a broad opening at a distal end. When the open end is placed against a tumor, air is evacuated from the resulting chamber through vacuum holes 304 to draw the entire tumor or a portion thereof into the chamber. The tumor is drawn so that one or more of the terminals 302 preferably penetrates the tumor. Sharp ends of the terminals 302 are configured to pierce the tumor. The center terminal 302 may be at one polarity, and the outer six terminals 302 may be at the opposite polarity. Electric fields, such as nanopulse electric fields can then be precisely applied to the tumor using, for example, nsPEF system 100 (see FIG. 1).

The terminals 302 can be apposed, one of each positive and negative pair of terminals 302 on one side of a tumor and the other electrode of the pair on an opposing side of the tumor. Opposing sides of a tumor can include areas outside or within a tumor, such as if a needle terminal 302 pierces a portion of the tumor.

Figure 4:
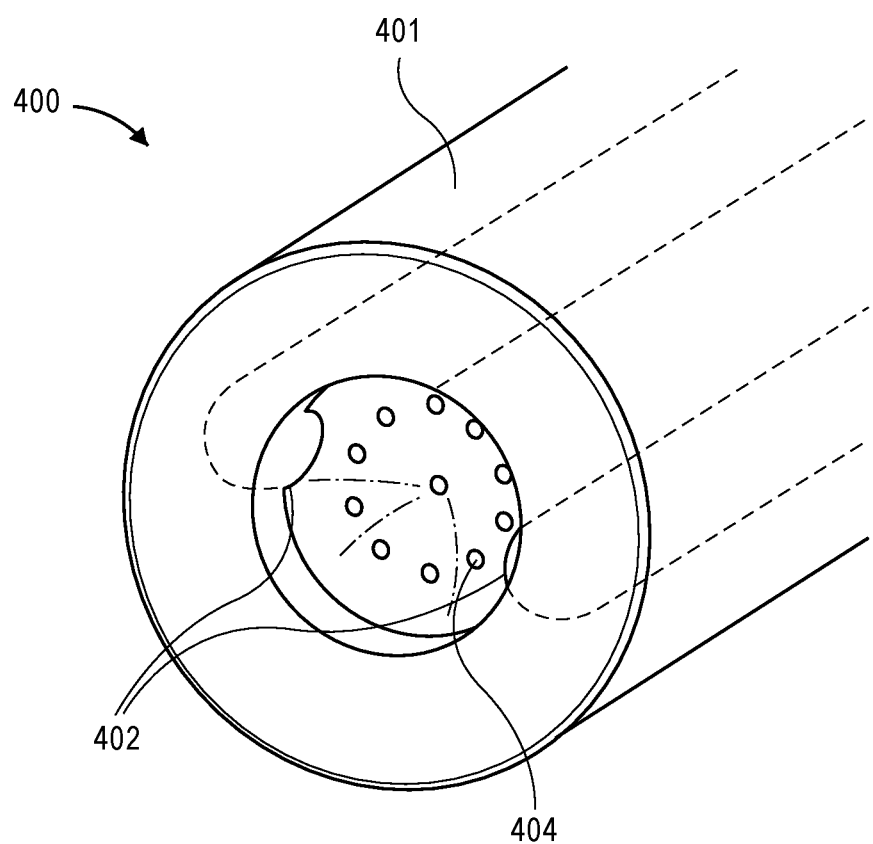
FIG. 4 illustrates a perspective view of a two-pole electrode in accordance with an embodiment.

FIG. 4 illustrates a two-pole suction electrode 400 in accordance with an embodiment. In electrode device 400, sheath 401 surrounds two broad terminals 402 on opposite sides of a chamber. When air is evacuated through vacuum holes 404 and a tumor is pulled within the chamber, the opposing terminals 402 apply nsPEF pulses to the tumor.

The nature of the electrode used mainly depends upon the shape of the tumor. Its physical size and stiffness can also be taken into account in selection of a particular electrode type.

U.S. Pat. No. 8,688,227 B2 (to Nuccitelli et al.) discloses other suction electrode-based medical instruments and systems for therapeutic electrotherapy, and it is hereby incorporated by reference.

If there are multiple tumors in a subject, a surgeon can select a single tumor to treat based on the tumor's compatibility with electrodes. For example, a tumor that is adjacent to a stomach wall may be more easily accessible than one adjacent a spine or the brain. Because a nsPEF pulse is preferably applied so that the electric field transits through as much tumor mass as possible while minimizing the mass of non-tumor cells that are affected, a clear path to two opposed 'poles' of a tumor may also be a selection criterion.

For tumors on or just underneath the skin of subject, needle terminals can be used percutaneously. For locations deeper within a subject, a retractable terminal can fit into a gastroscope, bronchoscope, colonoscope, or other endoscope or laparoscope. For example, a tumor in a patient's colon can be accessed and treated using a terminal within a colonoscope.

Barrett's esophagus, in which portions of tissue lining a patient's esophagus are damaged, may be treated using an electrode placed on an inflatable balloon.

Embodiments of nanosecond pulsed power generators produce electric pulses in the range of single nanoseconds to single microseconds. The pulses are created by rapid release of energy stored in, for example, a capacitive or inductive energy reservoir to a load in a period that is generally much shorter than the charging time of the energy reservoir.

Conventional capacitive-type pulsed generators include pulse forming networks, which provide fixed pulse duration and impedance. With prior knowledge of a load's resistance, a pulse forming network with impedance that matches the load can be used. But for broader applications, especially when the load resistance is unknown, it is desirable to have a pulse generator with a flexibility of impedance matching and variation of pulse duration. Such flexibility can be implemented by switching a capacitor with a controllable switch. In this case, the capacitor can be regarded as a "voltage source" and can adapt to various load resistances. The switched pulse amplitude can then have the same voltage as the voltage of the capacitor. The pulse width is accordingly determined by the switch "on" time.

The selection of switches in nanosecond pulse generators is limited because of the high voltages, high currents, and fast switching times involved.

Spark gap switches, typically used in pulsed power technology, are capable of switching high voltages and conducting high currents. But they can only be turned on, and stopping the current flow in the middle of conduction is impossible. Besides spark gaps, other types of high voltage, high power switches are available, such as: magnetic switches, vacuum switches (Thyratrons for example), and certain high-voltage semiconductor switches.

Magnetic switches, relying on the saturation of magnetic core, change from high impedance to low impedance in the circuit. They can be turned on above a certain current threshold but will not be turned off until all the current is depleted by the load.

Vacuum switches are a good option for high voltage and high repletion rate operation, but similar to magnetic switches, they also can be only turned on, but cannot be turned off at a predetermined time.

Some types of high-voltage semi-conductor switches may also be considered. Thyristors and insulated gate bipolar transistors (IGBTs) may, in some embodiments be used. However, the turn-on times of Thyristors and IGBTs limit their usefulness.

Metal-oxide-semiconductor field-effect transistors (MOSFETs) have insufficient maximum drain to source voltage ratings (e.g. <1 kV) and insufficient maximum drain to source current ratings (e.g. <50 A) to be used in conventional pulse generator architectures to produce the voltage and current necessary for the applications discussed herein. If they were used, a large number of stages would be needed in order to produce high-amplitude output voltages. However, in conventional Marx generator architectures with a large number of stages, the Marx generator goes into an underdamped mode instead of a critically damped mode, resulting in loss in overshoot. As a result, the overall voltage efficiency decreases. For example, a voltage efficiency of a Marx generator may be 80% at 5 stages but decrease to 50% at 20 stages.

Furthermore, as the number of stages is increased, the impedance of the Marx generator also increases. This reduces the total energy deliverable to the load. This is particularly unfavorable for driving low impedance loads and long pulses.

In addition, the charging losses in the charging resistors also increases with the increased number of stages. As a result, such Marx generators are unsuitable for high repetition rate operation.

Therefore, in order to produce high voltage pulses, simply increasing the number of stages will cause a series of problems, including low efficiency, high impedance, etc. Because there is a tradeoff between the number of the stages and the actual output voltage, using conventional Marx generators cannot produce high voltage pulses which are sufficient for the applications discussed herein.

Some embodiments of this disclosure include a tunable, high voltage, nanosecond pulse generator. The switches may be power MOSFETs, which may, for example, be rated for a voltage of 1 kV and current of up to 30A. Voltage is scaled up by a Marx-switch stack hybrid circuit. In each Marx generator stage, a particularly configured stack of MOSFETs is used. As a result, the charging voltage for each stage is greater than the rated maximum for a single switch.

A technical advantage of the configuration is that the overall output voltage can be increased with just a few stages (e.g. <=5). As a result, the problems discussed above with Marx generators having a large number of stages are avoided and high efficiency, low impedance, and large variability in the pulse duration can be achieved.

Such an architecture also allows much easier control as only one trigger circuit may be needed for each stage. One additional benefit is that the pulse generator has low impedance, so it will be able to drive various loads with high current and extended pulse duration. The scaling up of the current is implemented by combining multiple Marx-switch stack circuits in parallel. The pulse duration is controlled by the closing and opening of the switch stack switches.

Figure 5:
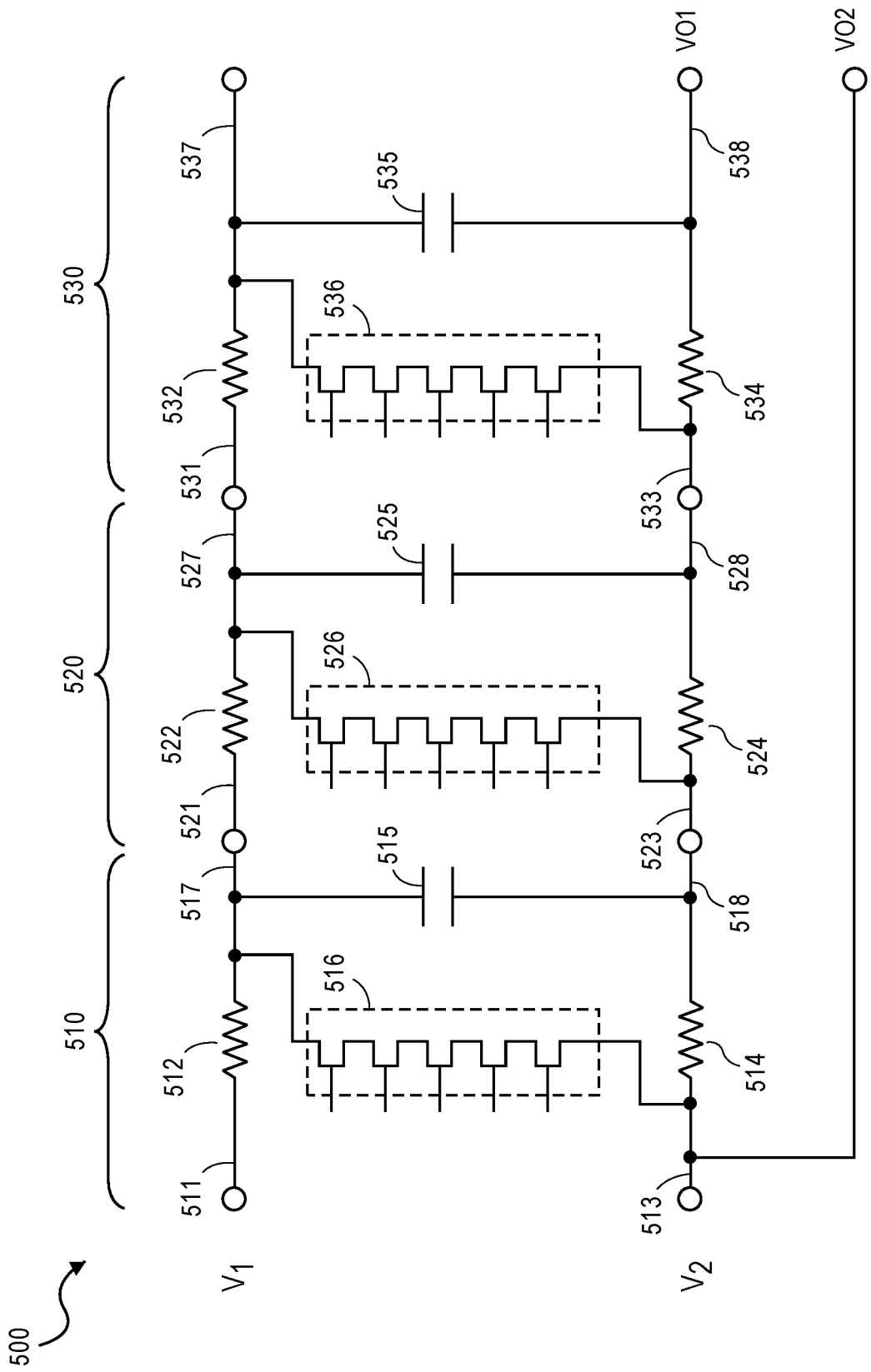
FIG. 5 is an electrical schematic of a pulse generator in accordance with an embodiment.

FIG. 5 illustrates a pulse generator circuit 500 which may be used inside nsPEF system 100 of FIG. 1. Pulse generator circuit 500 illustrates a panel comprising a Marx generator switched by three switch stacks. The nsPEF system can have a single pulse generator circuit panel. In some embodiments, a nsPEF system includes multiple panels in parallel.

Circuit 500 includes three stages—510, 520, and 530. In some embodiments, another number of stages is used. For example, in some embodiments, 2, 4, 5, 6, 7, 8, 9, or 10 stages are used. Stage 510 includes resistors 512 and 514, capacitor 515, and switch stack 516. Likewise, stage 520 includes resistors 522 and 524, capacitor 525, and switch stack 526, and stage 530 includes resistors 532 and 534, capacitor 535, and switch stack 536. Each of these elements have structure and functionality which is similar to the corresponding elements of stage 510.

Stage 510 has first and second input voltage input terminals 511 and 513 and first and second voltage output terminals 517 and 518. Stage 520 has first and second input voltage input terminals 521 and 523, and first and second voltage output terminals 527 and 528. Stage 530 has first and second input voltage input terminals 531 and 533, and first and second voltage output terminals 537 and 538.

The first and second voltage input terminals 511 and 513 of stage 510 are respectively connected to first and second power supply input terminals V1 and V2. The first and second voltage output terminals 517 and 518 of stage 510 are respectively connected to the first and second voltage input terminals 521 and 523 of stage 520. The first and second voltage output terminals 527 and 528 of stage 520 are respectively connected to the first and second voltage input terminals 531 and 533 of stage 530. The second voltage output terminal 538 of stage 530 and second voltage input terminal 513 of stage 510 are respectively connected to first and second power output terminals VO1 and VO2.

Pulse generator circuit 500 operates in a charge mode, and in a discharge mode. During the charge mode, described below with reference to FIG. 6A in more detail, capacitors 515, 525, and 535 are charged by current received from the first and second power supply input terminals V1 and V2. During the discharge mode, described below with reference to FIG. 6B in more detail, capacitors 515, 525, and 535 are discharged to provide a current to a load (not shown) connected across first and second power output terminals VO1 and VO2.

Figure 6A:
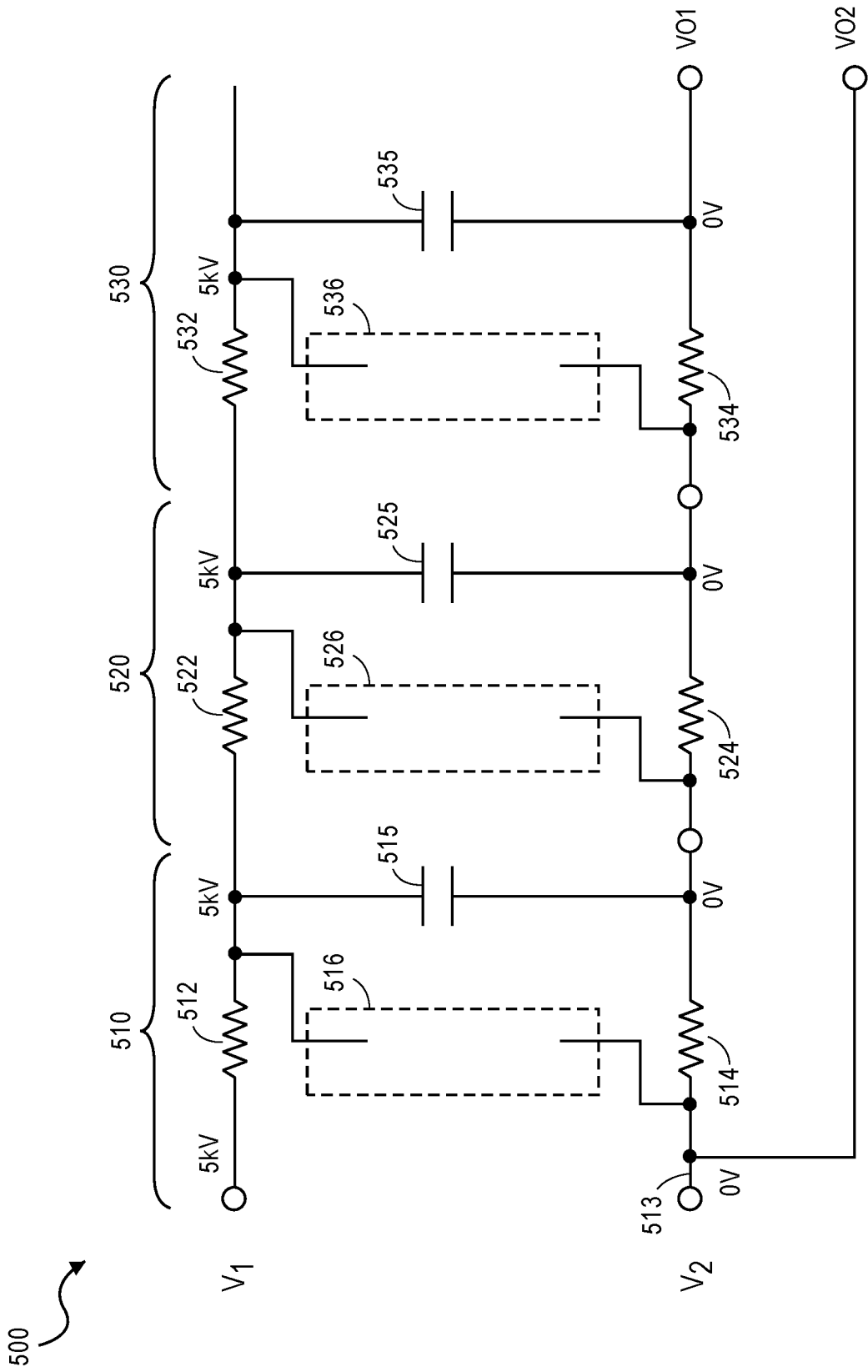
FIG. 6A is a schematic illustrating the pulse generator shown in FIG. 5 during charge mode.

FIG. 6A illustrates pulse generator circuit 500 during charge mode. First and second input voltages are respectively applied to first and second power supply input terminals V1 and V2 while each of switch stacks 516, 526, and 536 are nonconductive or open, and while first and second power output terminals may be disconnected from the load (not shown). Because each of switch stacks 516, 526, and 536 are open, substantially no current flows therethrough, and they are represented as open circuits in FIG. 6A. During the charge mode, each of capacitors 515, 525, and 535 are charged by current flowing through resistors 512, 522, 532, 534, 524, and 514 to or toward a voltage equal to the difference between the first and second input voltages.

Each of the switches of switch stacks 516, 526, and 536 has a breakdown voltage rating which should not be exceeded. However, because the switches are serially connected, the capacitors 515, 525, and 535 may be charged to a voltage significantly greater than the breakdown voltage of the individual switches. For example, the breakdown voltage of the switches may be 1 kV, and the capacitors 515, 525, and 535 may be charged to a voltage of 5 kV, when 5 or more switches are used in each switch stack.

For example, the first and second input voltages may respectively be 5 kV and 0V. In such an example, each of the capacitors 515, 525, and 535 is charged to or toward a voltage equal to 5 kV. In some embodiments, the difference between the first and second input voltages is limited to be less than 10 kV.

Figure 6B:
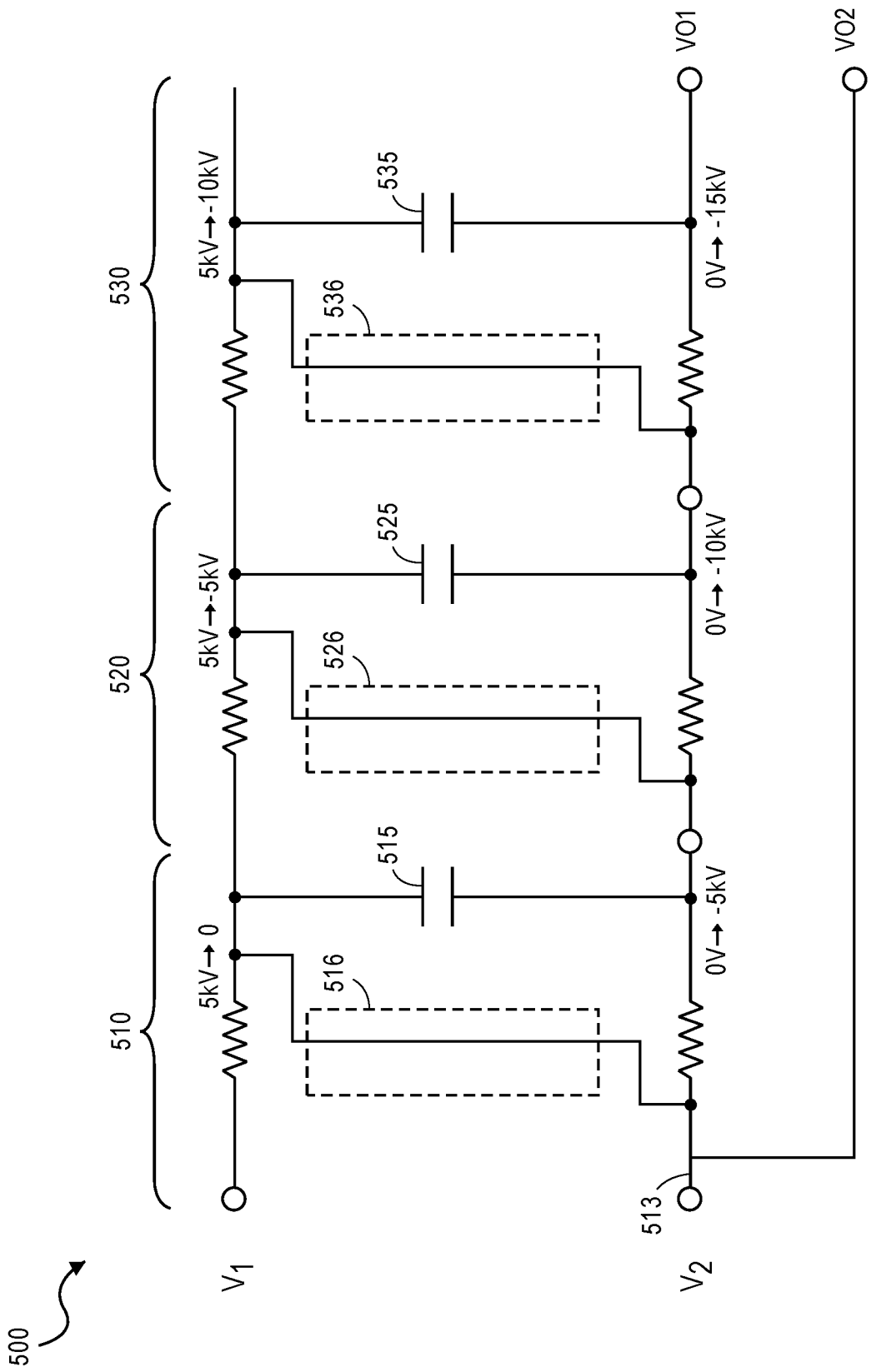
FIG. 6B is a schematic illustrating the pulse generator shown in FIG. 5 during discharge mode.

FIG. 6B illustrates pulse generator circuit 500 during discharge mode. First power supply input terminal V1 may be disconnected from the first input voltage. In some embodiments, first power supply input terminal V1 remains connected to the first input voltage. Second power supply input terminal V2 remains connected to the second input voltage. In addition, each of switch stacks 516, 526, and 536 are conductive or closed. Because each of switch stacks 516, 526, and 536 are closed, current flows therethrough, and they are represented as conductive wires in FIG. 6B. As a result, a low impedance electrical path from power supply input terminal V2 to power output terminal VO1 is formed by switch stack 516, capacitor 515, switch stack 526, capacitor 525, switch stack 536, and capacitor 535. Consequently, the difference between the voltages at the power output terminals VO1 and VO2 is equal to the number of stages (in this example, 3) times the difference between the first and second input voltages.

Where the first and second input voltages are respectively 5 kV and 0V, a voltage difference of 15 kV is developed across the power output terminals VO1 and VO2.

Figure 7:
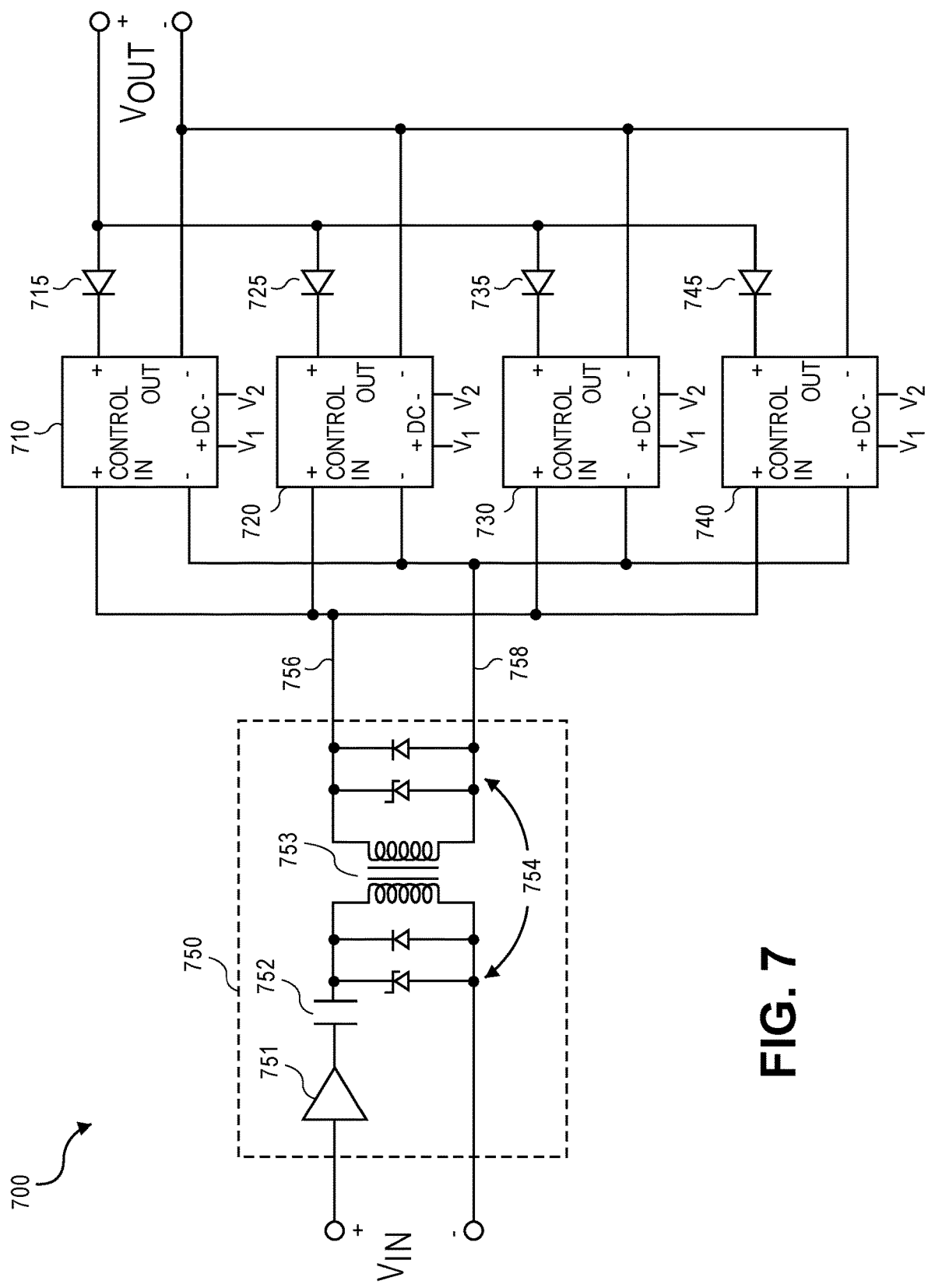
FIG. 7 is an electrical schematic of an assembly of pulse generator circuits.

FIG. 7 illustrates an alternative pulse generator circuit 700 which may be used inside nsPEF system 100 of FIG. 1. This pulse generator includes panels in parallel. The number of panels can be adjusted to allow the system to generate different amounts of current and power.

Pulse generator circuit 700 receives input pulses across input port Vin, and generates output pulses across output port Vout in response to the received input pulses.

Pulse generator circuit 700 includes multiple panels or pulse generator circuits 710, 720, 730, and 740. Pulse generator circuit 700 also includes driver 750. In this embodiment, four pulse generator circuits are used. An alternative embodiments, fewer or more pulse generator circuits are used. For example, in some embodiments, 2, 3, 5, 6, 7, 8, 9, 10 or another number of pulse generator circuits are used.

Each of the pulse generator circuits 710, 720, 730, and 740 may have characteristics similar to other pulse generator circuits discussed herein. For example, each the pulse generator circuits 710, 720, 730, and 740 may have characteristics similar to pulse generator circuit 500 discussed above with reference to FIGS. 5, 6A, and 6B.

Each of pulse generator circuits 710, 720, 730, and 740 has positive and negative DC input terminals, positive and negative control input terminals, and positive and negative output terminals, and is configured to generate output voltage pulses across the positive and negative output terminals in response to driving signal pulses applied across the positive and negative control input terminals. The output voltage pulses are also based on power voltages received across positive and negative DC power input terminals.

The driving signal pulses are generated across conductors 756 and 758 by driver 750, which includes amplifier circuit 751, capacitor 752, and transformer 753. In some embodiments, driver 750 also includes clamp circuits 754.

Driver 750 receives an input signal pulse at input port Vin and generates a driving signal pulse across conductors 756 and 758 in response to the input signal pulse. Amplifier circuit 751 receives the input signal pulse and drives transformer 753 through capacitor 752, which blocks low frequency and DC signals. In response to being driven by amplifier circuit 751, transformer 753 generates an output voltage pulse across conductors 756 and 758, such that the duration of the output voltage pulse is equal to or substantially equal (e.g. within 10% or 1%) to the duration of the input signal pulse at input port Vin.

In some embodiments, clamp circuits 754 are included at least to dampen potential signals, which may otherwise be caused by resonance. Clamp circuits 754 include parallel diodes, which provide a short-circuit path for any current reversal, and also clamp the maximum voltage across the components connected to the clamp circuits 754.

In some embodiments, transformer 753 has a 1:1 turns ratio. In alternative embodiments, a different turns ratio is used.

Each of pulse generator circuits 710, 720, 730, and 740 receives the voltage pulses from driver 750 across the positive and negative control input terminals and generates corresponding voltage pulses across the positive and negative output terminals in response to the received voltage pulses from driver 750. The voltage pulses generated across the positive and negative output terminals have durations which are equal to or substantially equal (e.g. within 10% or 1%) to the durations of the voltage pulses received from driver 750.

In this embodiment, the negative output terminals of pulse generator circuits 710, 720, 730, and 740 are directly connected to the negative Vout terminal of the output port Vout of pulse generator circuit 700. In addition, in this embodiment, the positive output terminals of pulse generator circuits 710, 720, 730, and 740 are respectively connected to the positive Vout terminal of the output port Vout of pulse generator circuit 700 through diodes 715, 725, 735, and 745. Diodes 715, 725, 735, and 745 decouple pulse generator circuits 710, 720, 730, and 740 from one another. As a consequence, interference and the associated pulse distortion that would otherwise occur is substantially eliminated. For example, diodes 715, 725, 735, and 745 prevent current from one of pulse generator circuits 710, 720, 730, and 740 to another of pulse generator circuits 710, 720, 730, and 740 if the switching is not perfectly synchronous. Diodes 715, 725, 735, and 745 also prevent current from flowing from the pulse generator circuits 710, 720, 730, and 740 while they are charging.

In this embodiment, diodes 715, 725, 735, and 745 each include a single diode. In alternative embodiments, diodes 715, 725, 735, and 745 each include multiple diodes connected serially based at least upon voltage ratings of the serially connected diodes. Additionally or alternatively, in some embodiments, diodes 715, 725, 735, and 745 each include multiple diodes connected in parallel based at least upon the current ratings of the parallel connected diodes.

In this embodiment, diodes 715, 725, 735, and 745 are connected so as to conduct current from the positive terminal of output port Vout toward pulse generator circuits 710, 720, 730, and 740, as pulse generator circuits 710, 720, 730, and 740 in this embodiment are configured to generate negative pulses. In alternative embodiments, where pulse generator circuits are configured to generate positive pulses, diodes may be similarly connected so as to conduct current from the pulse generator circuits to the positive terminal of the output port.

Figure 8:
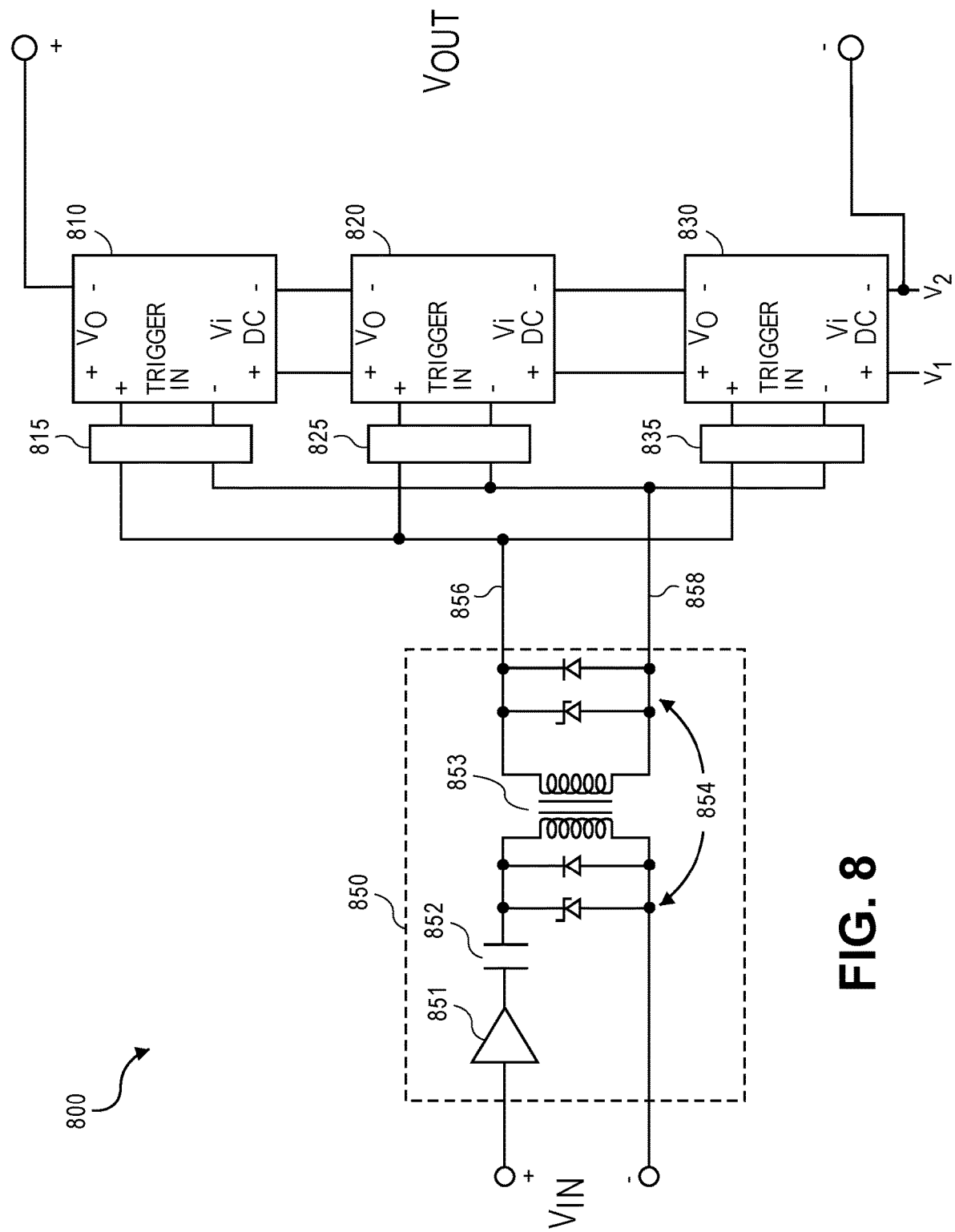
FIG. 8 is an electrical schematic of one of the pulse generator circuits shown in FIG. 7.

FIG. 8 illustrates a pulse generator circuit 800 which may be used for pulse generator circuits 710, 720, 730, and 740 of pulse generator circuit 1000 of FIG. 7.

Pulse generator circuit 800 receives input pulses across input port Vin, and generates output pulses across output port Vout in response to the received input pulses.

Pulse generator circuit 800 includes multiple pulse generator stages 810, 820, and 830. In this embodiment, pulse generator circuit 700 also includes driver 850, and optional common mode chokes 815, 825, and 835.

Each of the pulse generator stages 810, 820, and 830 may have characteristics similar to other pulse generator stages discussed herein. For example, each the pulse generator stages 810, 820, and 830 may have characteristics similar to stages 510, 520, and 530 of pulse generator circuit 500 discussed above with reference to FIGS. 5, 6A, and 6B. In some embodiments, fewer or more pulse generator stages may be used.

Each of pulse generator stages 810, 820, and 830 has positive and negative trigger input terminals, power positive and negative DC input terminals, and positive and negative Vo output terminals, and is configured to generate output voltage pulses across the positive and negative Vo output terminals in response to driving signal pulses applied across the positive and negative trigger input terminals. The output voltage pulses are also based on power voltages V1 and V2 respectively received at power positive and negative DC input terminals.

In this embodiment, the negative Vi input terminal of pulse generator stage 830 is connected with the negative terminal of the output port Vout of pulse generator circuit 800. In addition, in this embodiment, the negative Vo output terminal of pulse generator stage 810 is connected with the positive terminal of the output port Vout of pulse generator circuit 800.

In addition, as shown, the positive Vo output terminal of pulse generator 830 is connected with the positive Vi input terminal of pulse generator 820, and the negative Vo output terminal of pulse generator 830 is connected with the negative Vi input terminal of pulse generator 820. Furthermore, the positive Vo output terminal of pulse generator 820 is connected with the positive Vi input terminal of pulse generator 810, and the negative Vo output terminal of pulse generator 820 is connected with the negative Vi input terminal of pulse generator 810.

The driving signal pulses for pulse generator stages 810, 820, and 830 are generated across conductors 856 and 858 by driver 850, which includes amplifier circuit 851, capacitor 852, and transformer 853. In some embodiments, driver 850 also includes clamp circuits 854.

Driver 850 receives an input signal pulse at input port Vin, which is connected to conductors 856 and 858, as shown in FIG. 8. Driver 850 generates a driving signal pulse across conductors 856 and 858 in response to the input signal pulse. Amplifier circuit 851 receives the input signal pulse, and drives transformer 853 through capacitor 852, which reduces or blocks low frequency and DC signals. In response to being driven by amplifier circuit 851, transformer 853 generates an output voltage pulse across conductors 856 and 858, such that the duration of the output voltage pulse is equal to or substantially equal (e.g. within 10% or 1%) to the duration of the input signal pulse at input port Vin.

In some embodiments, clamp circuits 854 are included at least to dampen potential signals, which may otherwise be caused by resonance. Clamp circuits 854 include parallel diodes, which provide a short-circuit path for any current reversal, and also clamp the maximum voltage across the components connected to the clamp circuits 854.

In some embodiments, transformer 853 has a 1:1 turns ratio. In alternative embodiments, a different turns ratio is used.

Each of pulse generator stages 810, 820, and 830 receives the voltage pulses from driver 850 through a corresponding choke 815, 825, or 835, which blocks high frequency signals, for example, from coupling from the high voltage pulse generator stages 810, 820, and 830. The voltage pulses are received at the positive and negative trigger input terminals and the pulse generator stages 810, 820, and 830 each generate corresponding voltage pulses across the positive and negative Vo output terminals in response to the received voltage pulses from driver 850. The voltage pulses generated across the positive and negative Vo output terminals have durations which are equal to or substantially equal (e.g. within 10% or 1%) to the durations of the voltage pulses received from driver 850.

Figure 9:
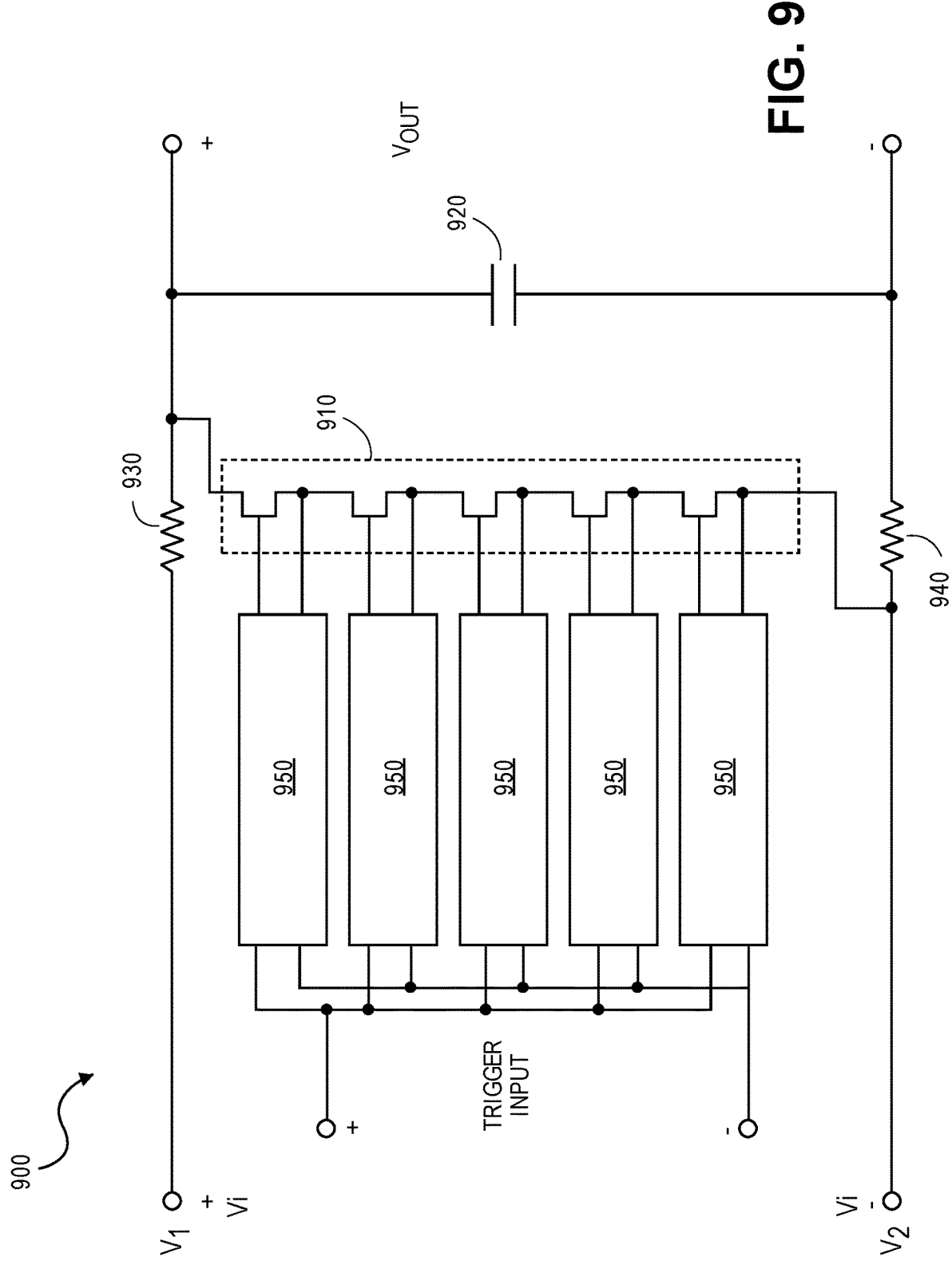
FIG. 9 is an electrical schematic of one of the pulse generator stages shown in FIG. 8.

FIG. 9 illustrates a pulse generator stage 900 which may be used as one of the pulse generator stages 810, 820, and 830 of pulse generator circuit 800 shown in FIG. 8.

Pulse generator stage 900 receives trigger pulses across input port trigger input, and generates output voltages at output port Vout in response to the received trigger pulses. The output voltages are also generated based on power voltages received at power input terminals V1 and V2. Pulse generator stage 900 includes multiple switch drivers 950. Pulse generator stage 900 also includes switch stack 910, capacitor 920, and resistors 930 and 940.

Switch drivers 950 are configured to receive the trigger pulses, and to generate control signals for the switches of switch stack 910 in response to the received trigger pulses, as discussed in further detail below. Each of the control signals is referenced to a voltage specific to the switch being driven. Accordingly, a first switch receives a control signal pulse between first and second voltages, and a second switch receives a control signal pulse between third and fourth voltages, where each of the first, second, third, and fourth voltages are different. In some embodiments, the difference between the first and second voltages is substantially the same as the difference between the third and fourth voltages.

Switch stack 910, capacitor 920, and resistors 930 and 940 cooperatively function with corresponding elements in the other pulse generator stages of pulse generator circuit 800, discussed above with reference to FIG. 8, to generate the voltage pulses across the positive and negative Vo output terminals of pulse generator circuit 800. These elements may, for example, cooperatively function as the corresponding elements discussed above with reference to pulse generator circuit 500 shown in FIGS. 5, 6A, and 6B. For example, these elements may cooperate to generate the voltage pulses across the positive and negative Vo output terminals of pulse generator circuit 800 in response to the power voltages applied to power input terminals V1 and V2 and to the control signals applied to the switches of switch stack 910.

Because the control signals are generated in response to the input pulses received across input port Vin of pulse generator circuit 700 illustrated in FIG. 7 through multiple stages of driving, the control signals cause all of the switches of the switch stacks of pulse generator circuit 700 to be turned on and to be turned off substantially simultaneously. For example, a 15V input pulse having a duration of, for example 100 ns, received at input port Vin of pulse generator circuit 700 may cause the pulse generator circuit 700 to generate a high-voltage (e.g. ~15 kV) output pulse having a duration of about 100 ns. Similarly, a 15V input pulse having a duration of, for example 5 μs, received at input port Vin of pulse generator circuit 700 may cause the pulse generator circuit 700 to generate a high-voltage (e.g. ~15 kV) output pulse having a duration of about 5 μs. Accordingly, the duration of the high-voltage output pulse is substantially the same as a selected duration of an input pulse.

Figure 10:
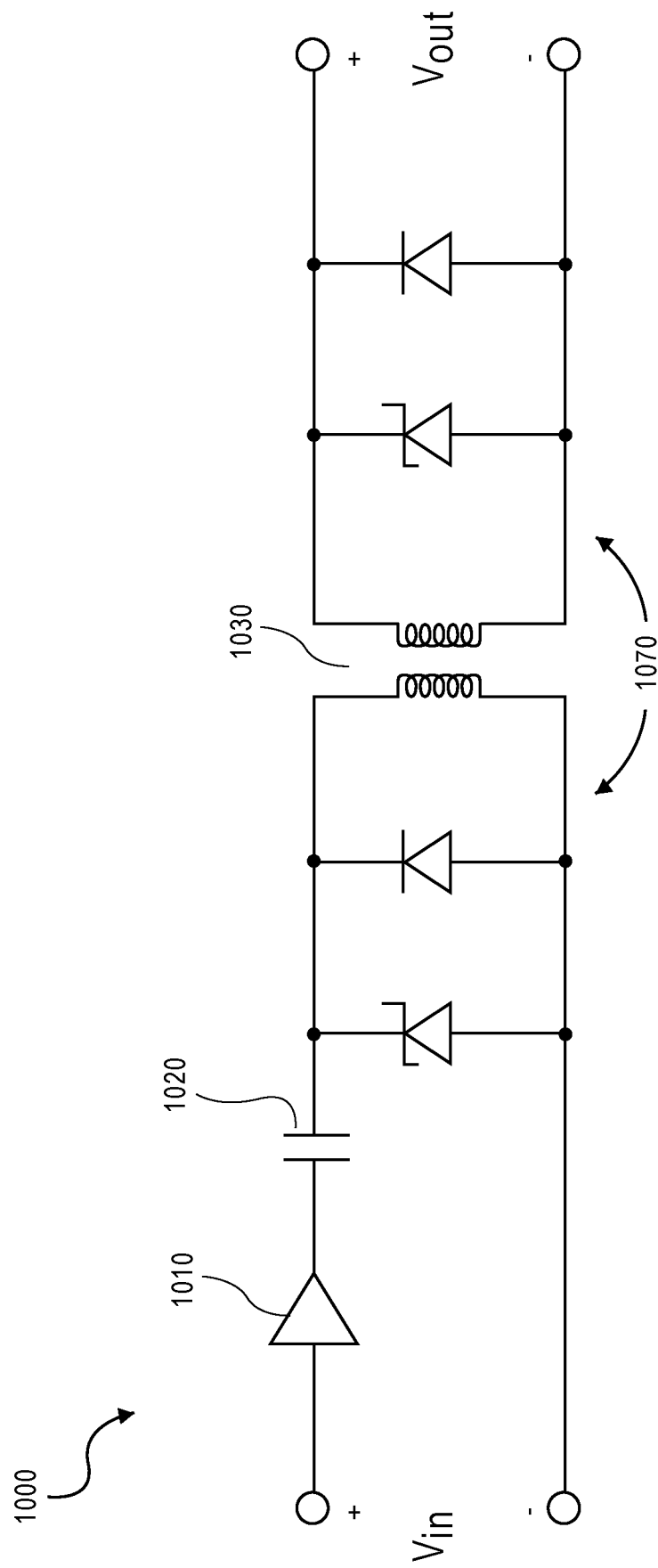
FIG. 10 is an electrical schematic of one of the switch drivers shown in FIG. 9.

FIG. 10 illustrates a switch driver 1000 which may be used as one of the switch drivers shown in FIG. 9.

Switch driver 1000 receives trigger pulses across input port Vin, and generates control signal pulses at output port Vout in response to the received trigger pulses. Switch driver 1000 includes amplifier circuit 1010, capacitor 1020, and transformer 1030. In some embodiments, switch driver 1000 also includes clamps circuits 1070.

Amplifier circuit 1010 receives the trigger pulses, and drives transformer 1030 through capacitor 1020, which reduces or blocks low frequency and DC signals. In response to being driven by amplifier circuit 1010, transformer 1030 generates control signal pulses across optional clamp circuits 1070 at output port Vout, such that the duration of the control signal pulses is equal to or substantially equal (e.g. within 10% or 1%) to the duration of the trigger pulses at input port Vin.

In some embodiments, amplifier circuit 1010 includes multiple amplifier integrated circuits. For example, for increased current driving capability, multiple amplifier integrated circuits may be connected in parallel to form amplifier circuit 1010. For example, 2, 3, 4, 5, 6, 7, 8 or another number of amplifier integrated circuits may be used.

In some embodiments, clamp circuits 1070 are included at least to dampen potential signals, which may otherwise be caused by resonance. Clamp circuits 1070 include parallel diodes, which provide a short-circuit path for any current reversal, and also clamp the maximum voltage across the components connected to the clamp circuits 1070.

In some embodiments, the drivers 750, 850, and 1000 receive power from a DC-DC power module which is isolated from the power supply for the Marx generator. This ensures the cutoff of ground coupling.

In some embodiments, transformer 1030 has a 1:1 turns ratio. In alternative embodiments, a different turns ratio is used.

In some embodiments, in order to obtain very fast switching, the transformers 1030 has fewer than 5 turns in the primary winding and fewer than 5 turns in the secondary winding. For example, in some embodiments, the transformer 1030 has 1, 2, 3, or 4 turns in each of the primary and secondary windings. In some embodiments, the transformer 1030 has less than a complete turn, for example, ½ turn in the primary and secondary windings. The low number of turns in each of the primary and secondary windings allows for a low inductance loop and increases the current risetime in the secondary winding, which charges the input capacitance of the MOSFET switches.

Transformers for triggering MOSFETs in conventional applications require high coupling, high permeability, and a low-loss core in order to ensure current transfer efficiency. From pulse to pulse, the residual flux in the core needs to be cleared in order to avoid saturation when the transformer is operated at high frequency. Conventionally, a resetting circuit, which involves a third winding, to dissipate the core energy is used.

In some embodiments, lossy transformers, such as that typically used as an electromagnetic interference (EMI) choke to confine high frequency signals and dissipate their energy as heat are used to trigger the switches. For example, the transformers may have a voltage time constant less than 100 Vµs. In some embodiments, the transformers have a voltage time constant less than 50 Vµs, 30 Vµs, 20 Vµs, 10 Vµs, or 5 Vµs. The use of the lossy transformer is contrary to the common practice in power electronics.

Although the high frequency flux is dampened due to the loss of the core (eddy loss, hysteresis loss, and resistive loss), the lossy transformers still allow sufficient confinement of the magnetic flux and provides sufficient coupling. In addition, the flux also decreases quickly enough. The flux decay process usually takes approximately several microseconds.

Having such a transformer conventionally seems disadvantageous, but for coupling nanosecond to a few microsecond pulses, such a transformer is preferably used. Consequently, the following benefits are achieved: 1) high voltage, high frequency transient coupling from the high-voltage Marx generators to the low-voltage drivers is suppressed; 2) because of the loss in the transformer cores, the residual flux from previous pulses are dissipated faster than common low-loss transformer cores, such that the resetting winding is not needed and is not present.

A benefit of the switch driver 1000 is that it limits the output pulse duration. Because the switch control signals are generated by transformer 1030, even if circuitry generating the input trigger signals at input port Vin were to generate a pulse of indefinite length, the transformer would saturate, causing the control signals to turn off the switches.

Figure 11:
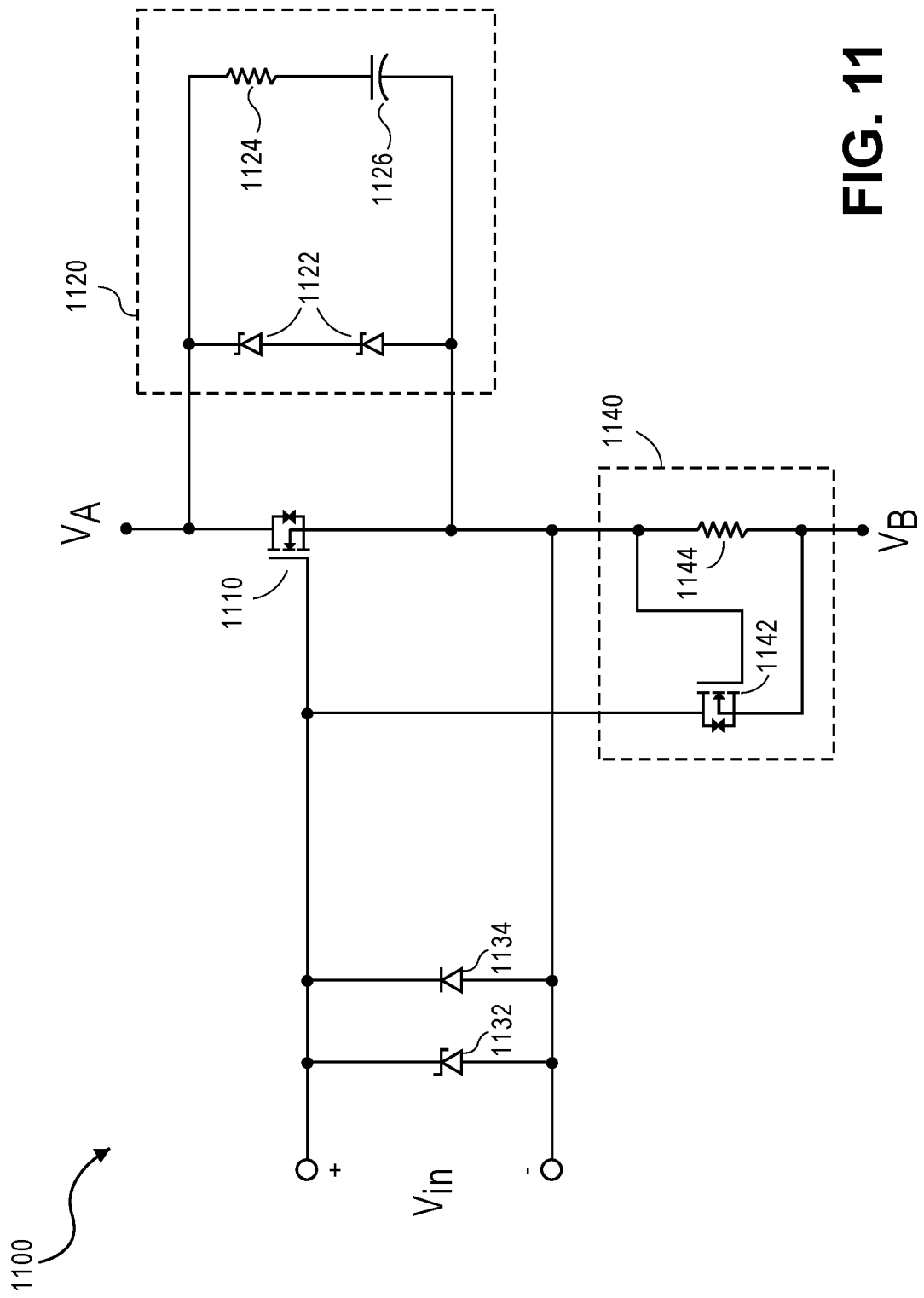
FIG. 11 is an electrical schematic of an alternative switch element.

FIG. 11 illustrates an example of a switch element 1100 comprising components which may be used in the switch stacks discussed here. Switch element 1100 includes switch 1110, and selectively forms a conductive or low resistance path between terminals VA and VB in response to a control voltage applied to input port Vin.

In some embodiments, switch 1110 is a transistor, such as a MOSFET. In some embodiments, switch 1110 is another type of switch. In some embodiments, switch 1110 has a turn on time of less than 5 ns, about 5 ns, about 10 ns, about 25 ns, about 15 ns, about 75 ns, about 100 ns, or greater than 100 ns.

In some embodiments, switch element 1100 also includes snubber circuit 1120. In some embodiments, the turn on times of the switches of the switch stacks are not identical. In order to prevent voltages greater than that which switch 1110 can tolerate, snubber circuit 1120 provides a current shunt path bypassing switch 1110. Diodes 1122 provide a low-frequency current path, and the combination of the capacitor 1126 and resistor 1124 provide a high-frequency current path.

In some embodiments, switch element 1100 also includes optional overcurrent protection circuit 1140. Overcurrent protection circuit 1140 includes switch 1142 and sense resistor 1144.

Current flowing from terminal VA to terminal VB is conducted through sense resistor 1144. Accordingly, a voltage is generated across sense resistor 1144 when the current flows from terminal VA to terminal VB. The generated voltage controls a conductive state of switch 1142. If the current flowing from terminal VA to terminal VB is greater than a threshold, the generated voltage causes the switch 1142 to conduct. As a result, switch 1142 reduces the control voltage of switch 1110. In response to the reduced control voltage, switch 1110 becomes less conductive or turns off. Consequently, the current which may be conducted from terminal VA to terminal VB is limited by overcurrent protection circuit 1140.

In the embodiments discussed herein, MOSFET switches are used. In alternative embodiments, other switches are used. For example, in some embodiments, thyristors, IGBTs or other semiconductor switches are used.

Figure 12:
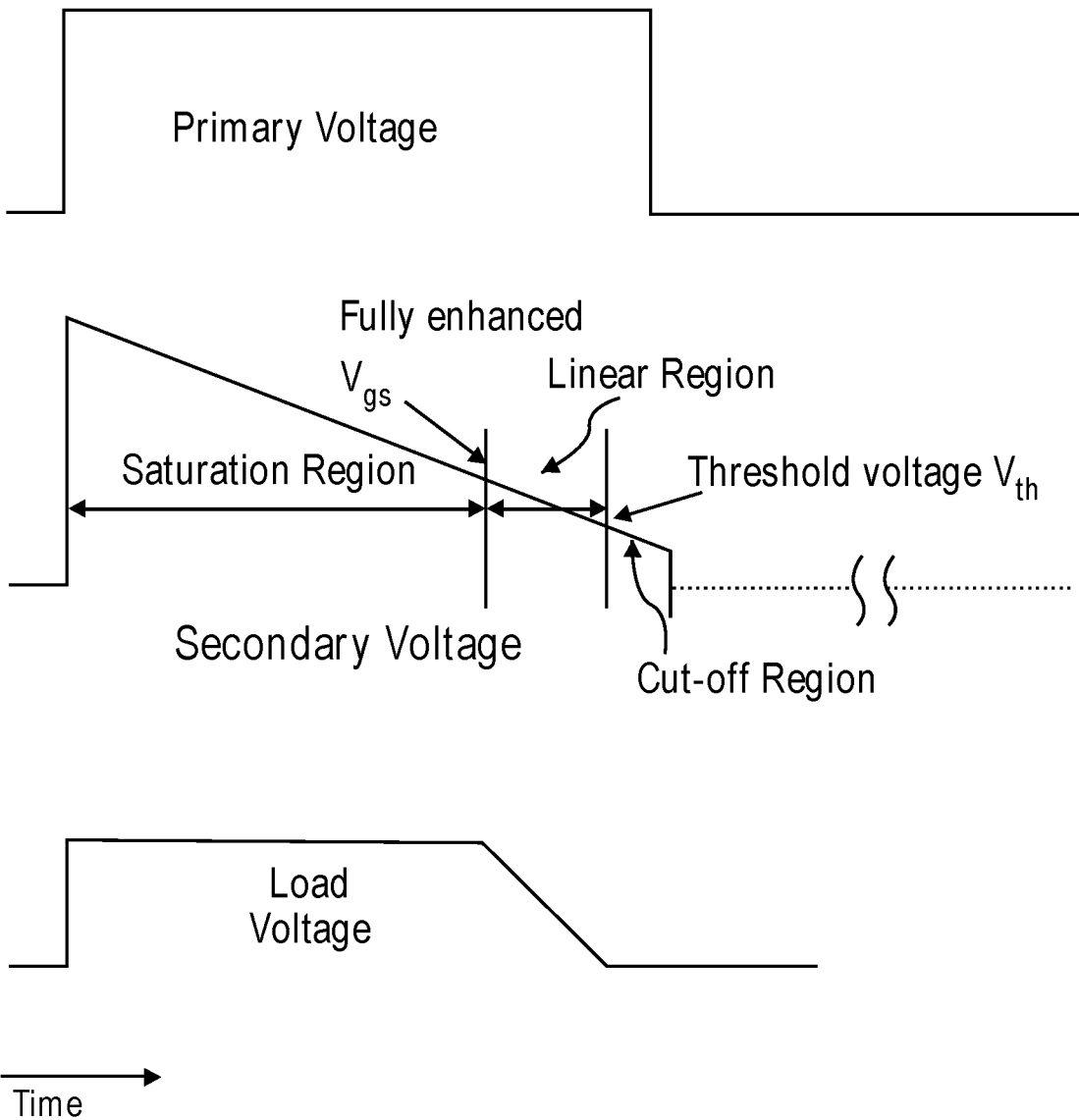
FIG. 12 is a waveform diagram illustrating the operation of a transformer and a control voltage to a MOSFET gate.

An example of the operation of the transformer is illustrated in FIG. 12. The voltage at the input primary inductor is substantially a square waveform, but the voltage at the secondary inductor, which is the MOSFET's gate-source voltage, tapers as the voltage magnitude decreases toward zero, for example, within a period of several microseconds. After a reduction in voltage at the secondary inductor, the switch receiving the voltage enters a linear region of operation from a saturation region of operation when the voltage is lower than the fully enhanced Vgs. As a result, the resistance of the switch increases and the output voltage across the load also shows a tapered profile. When the voltage at the secondary inductor decreases to a value less than the turn-on threshold of a MOSFET (Vth), the MOSFET will be shut off. Once the MOSFET is off, even if the duration of the trigger signal is extended, the voltage at the load goes to zero. The waveform of the voltage at the secondary inductor therefore limits the duration of high voltage output pulses from each panel, for example, to be several microseconds or less.

In some embodiments, the duration of the trigger signal is short enough that the switches remain in saturation because the reduction in voltage at the secondary inductor is insufficient to cause the switches to enter linear region operation. In such embodiments, the load voltage pulses do not exhibit the tapering illustrated in FIG. 12. For example, in such embodiments the load voltage pulses may be substantially square.

In some embodiments, the switch stacks discussed herein include switches, as discussed above, as well as other components.

In some embodiments, when generating pulses of a duration less than a threshold, the shape of the pulses are substantially square. In some embodiments, when generating pulses of the duration greater than a threshold, the shape of the pulses are substantially square for a duration substantially equal (e.g. within 10% or 1%) to the threshold. During the time after the threshold, the voltage of such long pulses drops toward 0 V. In some embodiments, the drop toward 0 V is substantially linear. In some embodiments, the drop toward 0 V is substantially exponential.

Figure 13:
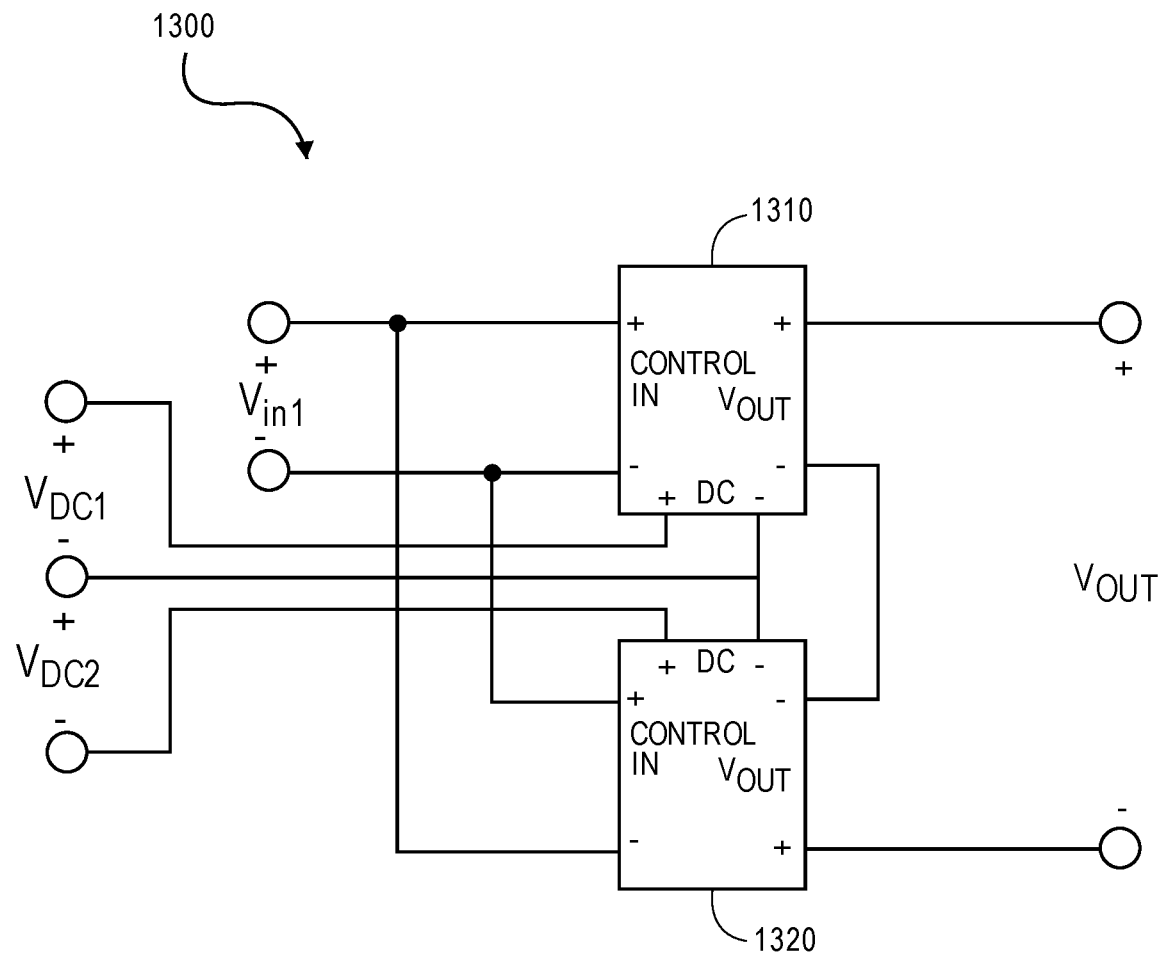
FIG. 13 is an alternative electrical schematic of a pulse generator shown in FIG. 1.

FIG. 13 illustrates an alternative pulse generator circuit 1300 which may be used inside nsPEF system 100 of FIG. 1.

Pulse generator circuit 1300 receives input pulses across input port Vin and DC voltages at input ports VDC1 and VDC2, and generates output pulses across output port Vout in response to the received input pulses and DC voltages.

Pulse generator circuit 1300 includes multiple pulse generator circuits 1310 and 1320. In this embodiment, two pulse generator circuits are used. In alternative embodiments, more pulse generator circuits are used. For example, in some embodiments, 3, 4, 5, 10 or another number of pulse generator circuits having their output ports serially connected, as discussed below with reference to pulse generator circuit 1300, are used.

Each of pulse generator circuits 1310 and 1320 may be similar to the other pulse generator circuits discussed herein. For example pulse generator circuits 1310 and 1320 may be similar to or may be substantially identical to pulse generator circuit 700 discussed above with reference to FIG. 7.

Each of pulse generator circuits 1310 and 1320 receive the same input pulse signal across their respective Control In input ports. In response, each of pulse generator circuits 1310 and 1320 generate high voltage pulses across their respective Vout output ports. Because the Vout output ports of pulse generator circuits 1310 1320 are serially connected, the voltage pulse generated by pulse generator circuits 1310 and 1320 across output port Vout of pulse generator circuit 1300 is substantially equal (e.g. within 10% or 1%) to the sum of the voltages of the pulses respectively generated by pulse generator circuits 1310 and 1320.

Figure 14:
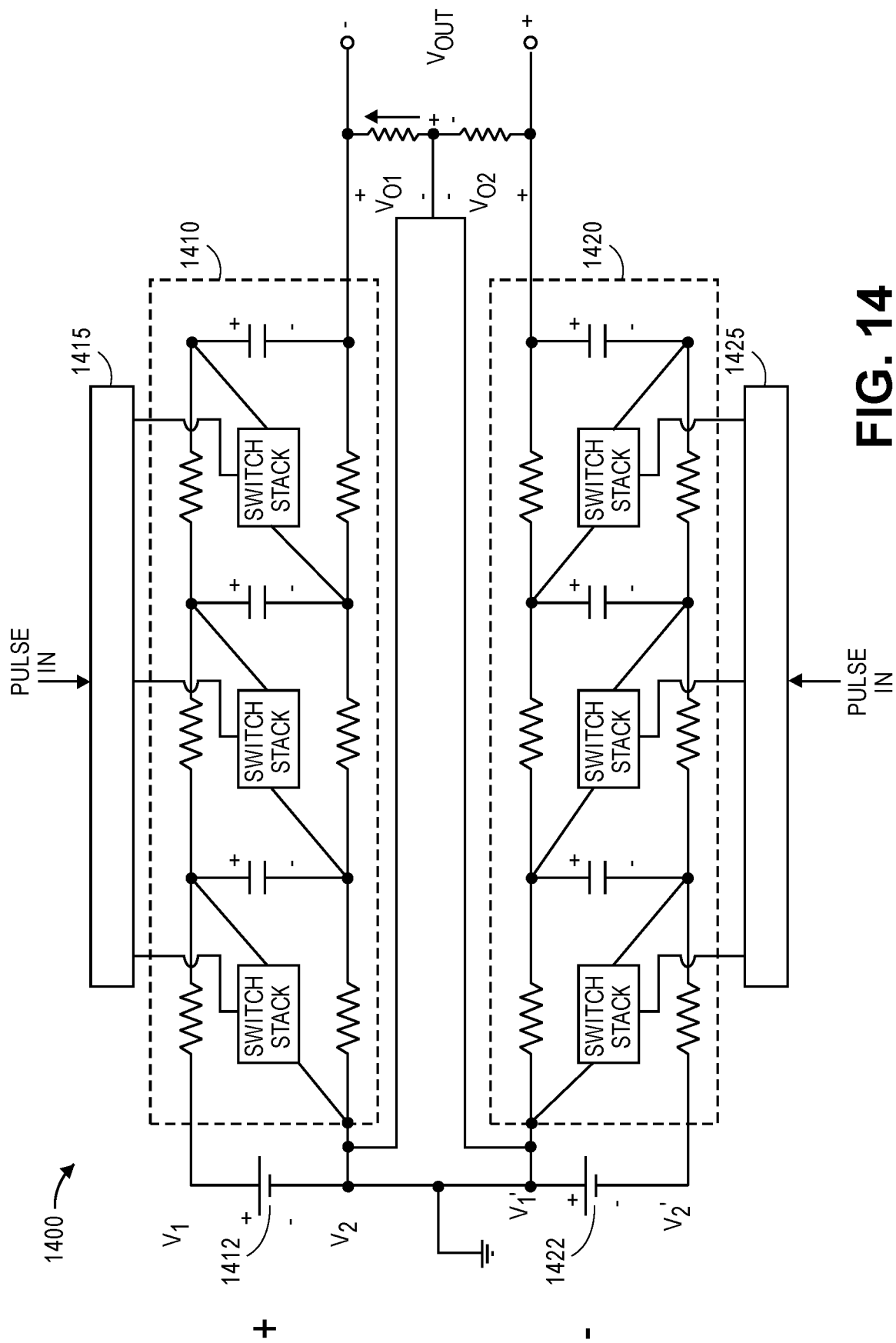
FIG. 14 is an alternative electrical schematic of a pulse generator shown in FIG. 1.

FIG. 14 illustrates an alternative pulse generator circuit 1400 which may be used inside nsPEF system 100 of FIG. 1, and which has characteristics similar to the pulse generator 1300 of FIG. 13. Pulse generator circuit 1400 includes pulse generators 1410 and 1420, drivers 1415 and 1425, and power supplies 1412 and 1422.

Pulse generator circuit 1400 includes multiple pulse generator circuits 1410 and 1420. In this embodiment, two pulse generator circuits are used. In alternative embodiments, more pulse generator circuits are used. Each of pulse generator circuits 1410 and 1420 may be similar to the other pulse generator circuits discussed herein.

Pulse generator circuit 1400 receives input pulses at each of drivers 1415 and 1425, which may be similar to driver 850 discussed above with reference to FIG. 8. Pulse generator circuit 1400 generates output pulses across output port Vout in response to the received input pulses. The output voltage pulses are also based on power voltages received from power supplies 1412 and 1422.

Each of drivers 1415 and 1425 receive an input pulse signal. In response to the received input signals, drivers 1415 and 1425 respectively generate driving signal pulses for pulse generator circuits 1410 and 1420. In response to the driving signal pulses, each of pulse generator circuits 1410 and 1420 generate high voltage pulses across their respective output ports Vo1 and Vo2. Because the Vo1 and Vo2 output ports of pulse generator circuits 1410 and 1420 are serially connected, the voltage pulse generated by pulse generator circuits 1410 and 1420 across output port Vout of pulse generator circuit 1400 is substantially equal (e.g. within 10% or 1%) to the sum of the voltages of the pulses respectively generated by pulse generator circuits 1410 and 1420.

In this embodiment, pulse generator circuit 1410 generates a high voltage pulse across its output port Vo1 which is substantially equal (e.g. within 10% or 1%) to three times the voltage of power supply 1412, (−3×[V1−V2]). In addition, pulse generator circuit 1420 generates a high voltage pulse across its output port Vo2 which is substantially equal (e.g. within 10% or 1%) to three times the voltage of power supply 1422 (3×[V'1−V'2]). As a result, pulse generator circuit 1400 generates a voltage of (3×[V'1−V'2])−(−3×[V1−V2]) across its output port Vout.

In some embodiments, a single driver circuit connected to both pulse generator circuit 1410 and 1420 is used instead of drivers 1415 and 1425. In such embodiments, the single driver circuit generates driving signal pulses for both pulse generator circuits 1410 and 1420 in response to an input pulse signal.

Figure 15:
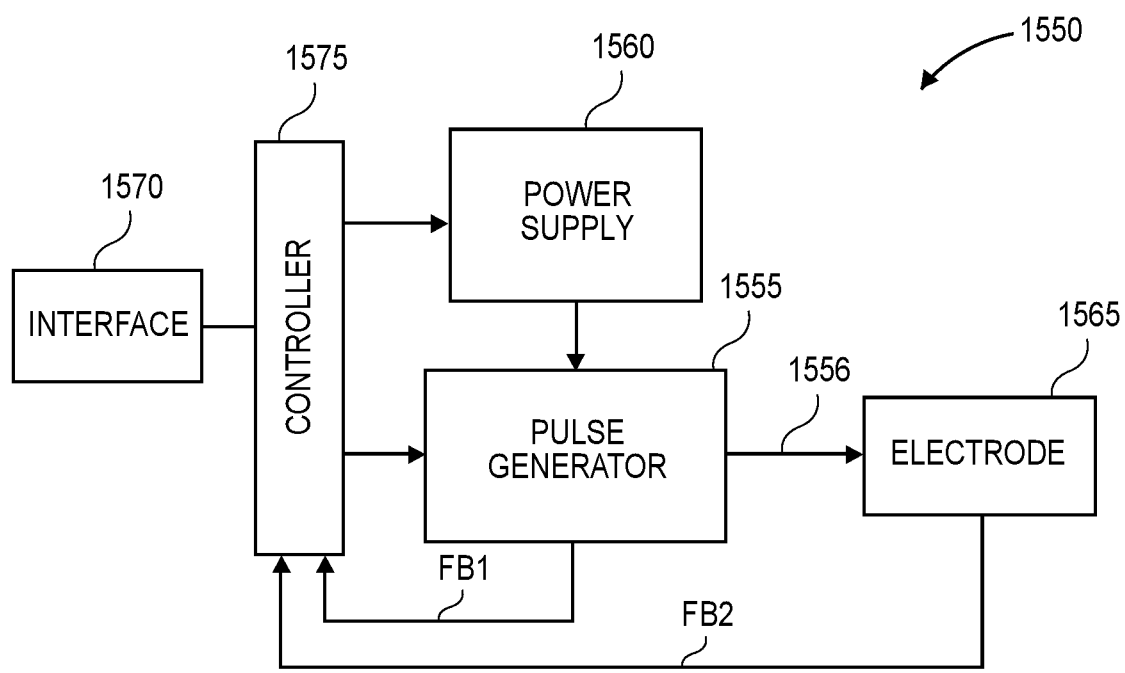
FIG. 15 is a block diagram of a nsPEF treatment system.

FIG. 15 is a block diagram of a nsPEF treatment system 1550, which has characteristics similar to or identical to those of nsPEF system 100 illustrated in FIG. 1. NsPEF treatment system 1550 includes pulse generator 1555, power supply 1560, electrode 1565, interface 1570, and controller 1575.

Pulse generator 1555 may be similar or identical to any of the pulse generator circuits discussed herein. For example, pulse generator 1555 may be configured to generate pulses having a voltage magnitude corresponding with power voltages received from power supply 1560 and having pulse widths and other characteristics corresponding with control signals received from controller 1575. In alternative embodiments, other pulse generator circuits may be used.

Electrode 1565 may be similar or identical to any of the electrodes discussed herein. For example, electrode 1565 may be similar or identical to electrodes 300 and 400 discussed above with reference to FIGS. 3 and 4. Electrode 1565 is configured to receive nsPEF pulses generated by pulse generator 1555 from conductor 1556 and is configured to deliver nsPEF pulses to a patient undergoing therapeutic nsPEF treatment. In alternative embodiments, other therapeutic electrodes may be used.

Power supply 1560 is configured to provide power voltages to pulse generator 1555. For example, in embodiments where pulse generator 1555 is similar to pulse generator circuit 700 illustrated in FIG. 7, power supply 1560 may be configured to provide power voltages corresponding with power voltages V1 and V2 of pulse generator circuit 700. In some embodiments, power supply 1560 generates and provides power voltages which have a voltage level corresponding with a control signal from controller 1575.

Interface 1570 is configured to receive input from a user identifying various parameters and characteristics of the nsPEF pulses to be applied to the patient. For example, interface 1570 may be configured to receive input identifying or specifying values for one or more characteristics of one or more nsPEF pulses to be applied to the patient. For example, the characteristics may include one or more of an amplitude, a polarity, a width, a rise time, and a fall time of one or more nsPEF pulses to be applied to the patient. Additionally or alternatively, the characteristics may include one or more of a frequency and a pulse quantity of a sequence of nsPEF pulses to be applied to the patient. Furthermore, the characteristics may additionally or alternatively include a result of the nsPEF pulses to be applied to the patient, such as a maximum temperature for the treated tissue of the patient or total energy delivered to the treated tissue of the patient. Other characteristics may additionally or alternatively be identified or specified by the received input.

In addition, interface 1570 is configured to communicate the characteristics identified or specified by the received input to controller 1575.

Controller 1575 is configured to generate and provide one or more control signals to pulse generator 1555 and to power supply 1560 based at least partly on the communicated characteristics received from interface 1570. Additionally, pulse generator 1555, power supply 1560, and electrode 1565 are collectively configured to, in response to the control signals from controller 1575, generate nsPEF pulses having characteristics corresponding with the control signals.

In this embodiment, one or both of pulse generator 1555 and electrode 1565 are configured to generate feedback signals FB1 and FB2 corresponding with or representing measured parametric characteristics of the nsPEF pulses applied to the patient. In some embodiments, the parametric characteristics of the nsPEF pulses represented by the feedback signals FB1 and FB2 include one or more of an amplitude, a polarity, a width, a rise time, and a fall time of the nsPEF pulses. Additionally or alternatively, the parametric characteristics may include a frequency of a sequence of nsPEF pulses. Furthermore, the parametric characteristics may additionally or alternatively include a temperature of the treated tissue of the patient. The feedback signals FB1 and FB2 may correspond or represent other measured parametric characteristics of one or more of the nsPEF pulses applied to the patient, the patient, the environment, and the nsPEF treatment system 1550. In alternative embodiments, only one of feedback signals FB1 and FB2 are generated. In some embodiments, neither of feedback signals FB1 and FB2 are generated.

In some embodiments, controller 1575, power supply 1560, pulse generator 1555, and electrode 1565 collectively form a feedback loop which causes one or more parametric characteristics of the nsPEF pulses applied to the patient to have measured values substantially equal (e.g. within 10% or 1%) to the values of corresponding characteristics identified in the input received by interface 1570.

For example, interface 1570 may receive input specifying a value of 15 kV for an amplitude of the nsPEF pulses applied to the patient. In addition, the controller 1575 may be configured to, in response to a feedback signal FB2 from electrode 1565 or a feedback signal FB1 from pulse generator 1555 indicating that the measured amplitude of the nsPEF pulses applied to the patient is less than (or greater than) 15 kV, change a control signal provided to power supply 1560. In response to the changed control signal, power supply 1560 may be configured to increase (or decrease) the voltage of power signals provided to pulse generator 1555 such that the amplitude of the nsPEF pulses generated and applied to the patient increases (or decreases) to or toward 15 kV.

Similarly, interface 1570 may receive input specifying a value of 150 ns for a pulse width of the nsPEF pulses applied to the patient. The controller 1575 may be configured to, in response to a feedback signal FB2 from electrode 1565 or a feedback signal FB1 from pulse generator 1555 indicating that the measured pulse width of the nsPEF pulses applied to the patient is greater than (or less than) 150 ns, change a control signal provided to pulse generator 1555. In response to the changed control signal, pulse generator 1555 may be configured to generate and apply to the patient nsPEF pulses having decreased (or increased) pulse width. As a result, the feedback signal FB1 or FB2 causes the controller 1575 to generate control signals which cause the pulse generator 1555 to generate and apply nsPEF pulses having pulse widths decreased (or increased) to or toward 150 ns.

In some embodiments, the feedback loop is controlled using a Proportional-Integral-Derivative (PID) method. For example, controller 1575 may be configured to continuously or substantially continuously calculate an error value as the difference between a desired value perceived at interface 1570 and a corresponding measured parameter. In addition, controller 1575 may be configured to continuously or substantially continuously calculate the control signals as a sum of one or more of: a first constant times the error signal, a second constant times an integral of the error signal, and a third constant times a derivative of the error signal.

In some embodiments, the feedback loop is controlled using a lookup table to determine a next value based on a measured value. In some embodiments, the feedback loop is controlled by reducing or increasing a value by a fixed amount or step size based on a determination of whether a measured value is greater than or less than a threshold.

Figure 16:
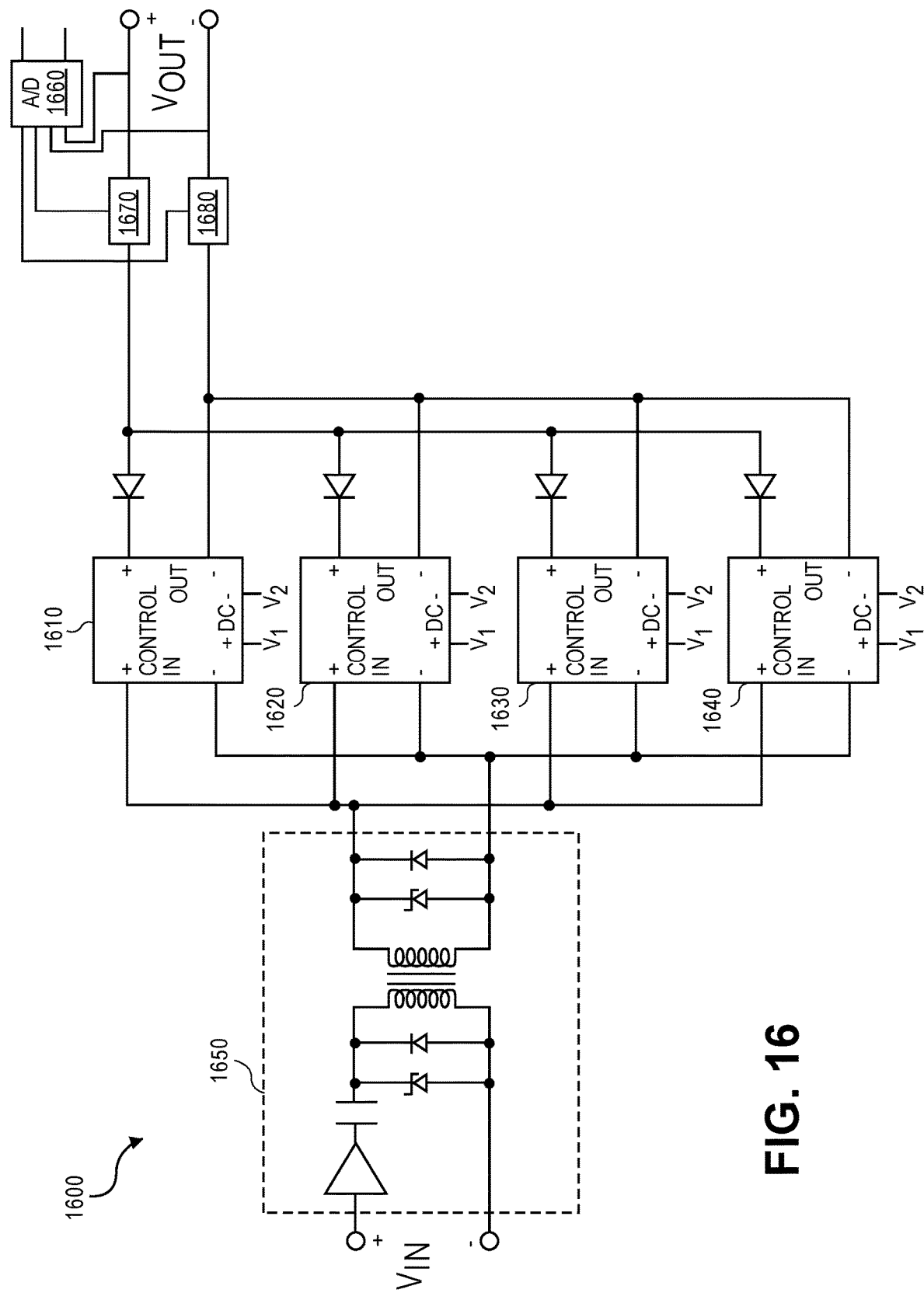
FIG. 16 is a schematic illustration of an alternative pulse generator.

FIG. 16 illustrates an alternative pulse generator 1600 which may be used as pulse generator 1555 of nsPEF treatment system 1550 illustrated in FIG. 15. Pulse generator 1600 may have features similar to or identical to other pulse generator circuits discussed herein. For example, pulse generator circuit 1600 may have features similar to or identical to pulse generator circuit 700 of FIG. 7.

For example, pulse generator 1600 includes the driver circuit 1650 which may be similar to or identical to driver 750 of pulse generator circuit 700. In addition, pulse generator 1600 includes pulse generator circuits 1610, 1620, 1630, and 1640, which may respectively be similar or identical to pulse generator circuits 710, 720, 730, and 740.

Pulse generator 1600 also includes, or in some embodiments is connected to, analog-to-digital converter 1660. Furthermore, pulse generator 1600 additionally or alternatively includes, or in some embodiments is connected to, current monitors 1670 and 1680.

In this embodiment, analog-to-digital (A/D) converter 1660 includes a first channel or group of channels having inputs which are respectively connected to the positive (+) and negative (−) voltage output terminals of pulse generator 1600. In some embodiments, a first differential buffer (not shown) is connected to the positive (+) and negative (−) voltage output terminals of pulse generator 1600, and drives the inputs of analog-to-digital converter 1660. In some embodiments, a probe, such as a Tektronix P6015A Passive High Voltage Probe (not shown) or similar probe is connected to the positive (+) and negative (−) voltage output terminals of pulse generator 1600, and drives the inputs of analog-to-digital converter 1660.

In some embodiments, only the positive (+) voltage output terminal is connected to analog-to-digital converter 1660. In some embodiments, the positive (+) voltage output terminal is connected to analog-to-digital converter 1660 through a voltage divider. In such embodiments, the voltage at the positive (+) voltage output terminal is ground referenced, and the ground is also connected to analog-to-digital converter 1660. For example, the positive (+) voltage output terminal is ground referenced if the negative (−) voltage output terminal of pulse generator 1600 is at the ground voltage.

In addition, analog-to-digital converter 1660 is configured to generate a first digital output representing the voltage difference between the positive (+) and negative (−) voltage output terminals of pulse generator 1600. When used in the nsPEF treatment system 1550 of FIG. 15, the first digital output may be used as a feedback signal for controller 1575. In some embodiments, analog-to-digital converter 1660 generates the first digital output based on either, but not both, of the voltages at the positive (+) and negative (−) voltage output terminals.

In this embodiment, analog-to-digital converter 1660 also includes a second channel or group of channels having inputs which are respectively connected to the current monitors 1670 and 1680, and the current monitors 1670 and 1680 are respectively connected to the positive (+) and negative (−) voltage output terminals of pulse generator 1600. In some embodiments, a second differential buffer (not shown) is connected to the current monitors 1670 and 1680, and drives the inputs of analog-to-digital converter 1660.

In addition, analog-to-digital converter 1660 is configured to generate a second digital output representing the current difference between the currents flowing through positive (+) and negative (−) voltage output terminals of pulse generator 1600. When used in the nsPEF treatment system 1550 of FIG. 15, the second digital output may be used as a feedback signal for controller 1575. In some embodiments, analog-to-digital converter 1660 generates the second digital output based on either, but not both, of inputs from the current monitors 1670 and 1680.

In some embodiments, current monitors 1670 and 1680 each include a sense resistor and an amplifier. The sense resistor is configured to generate a voltage response of the current flowing therethrough, and the amplifier generates an input for the analog-to-digital converter based on the voltage across the sense resistor.

In some embodiments, current monitors 1670 and 1680 include a current monitor, such as Pearson Current Monitor 2878, or another current monitor, which generates a voltage in response to a sensed current.

In some embodiments, pulse generator 1600 generates either, but not both, of the first and second digital outputs. In some embodiments, one or more single channel analog-to-digital converters are used instead of or in addition to analog-to-digital converter 1660.

In some embodiments, only single current monitor is used. The single current monitor may monitor the current of either of the positive (+) and negative (−) voltage output terminals of pulse generator 1600.

Figure 17:
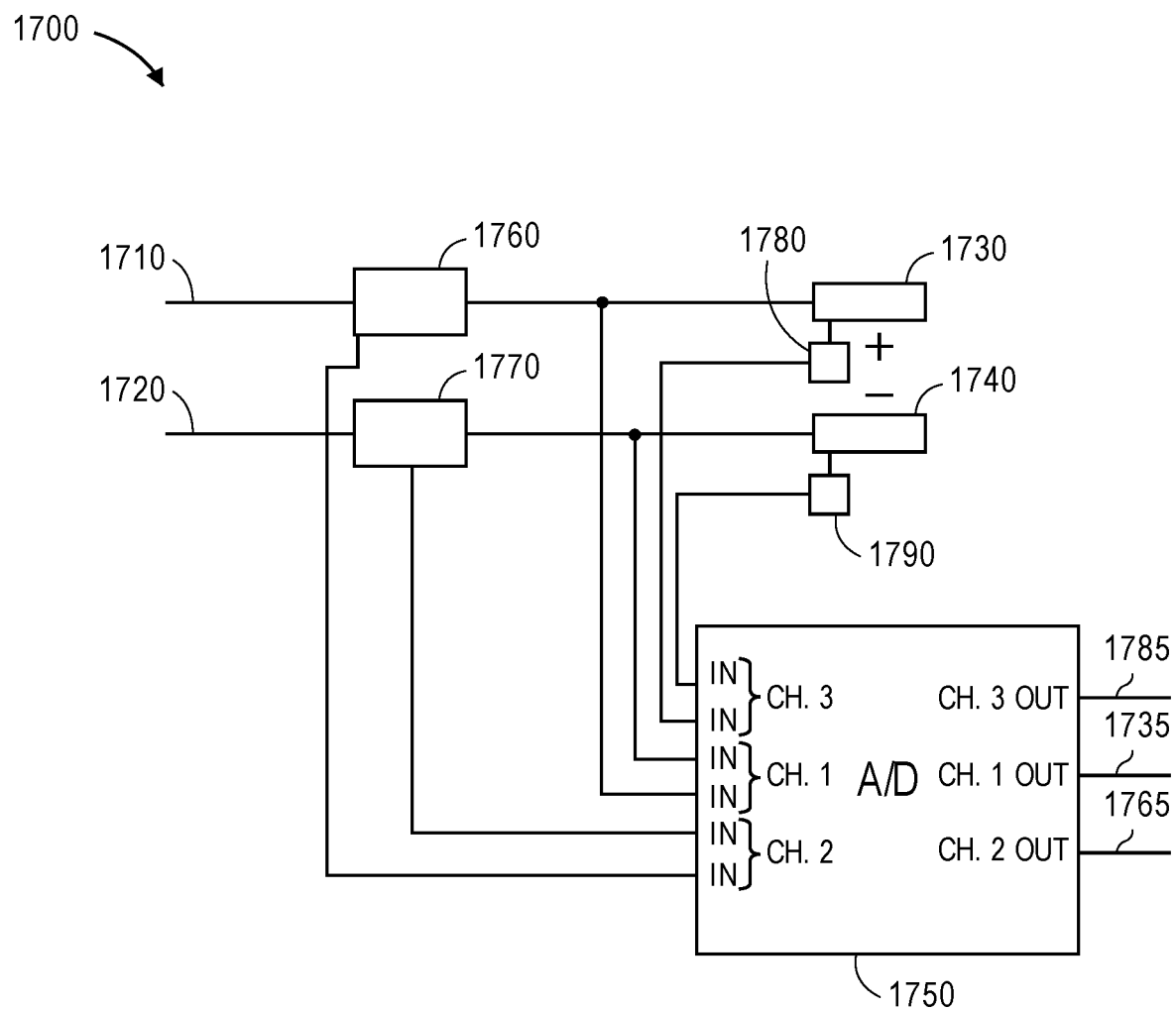
FIG. 17 is a schematic illustration of an electrode which may be used in the nsPEF treatment system of FIG. 15.

FIG. 17 is a schematic illustration of an electrode 1700 which may, for example, be used as electrode 1565 in nsPEF treatment system 1550 of FIG. 15. Electrode 1700 may be similar or identical to any of the electrodes discussed herein. For example, electrode 1700 may be similar or identical to electrodes 300 and 400 discussed above with reference to FIGS. 3 and 4.

Electrode 1700 is configured to receive nsPEF pulses across input terminals 1710 and 1720 and to deliver nsPEF pulses to a patient undergoing therapeutic nsPEF treatment through positive (+) and negative (−) output therapeutic electrodes 1730 and 1740.

Electrode 1700 includes, or in some embodiments is connected to, analog-to-digital converter 1750. Furthermore, electrode 1700 additionally or alternatively includes, or in some embodiments is connected to, current monitors 1760 and 1770. In addition, electrode 1700 includes thermal sensors 1780 and 1790. In some embodiments, electrode 1700 includes either but not both of thermal sensors 1780 and 1790.

In this embodiment, analog-to-digital converter 1750 includes a first channel having inputs which are respectively connected to the positive (+) and negative (−) voltage output therapeutic electrodes 1730 and 1740. In some embodiments, a first differential buffer (not shown) is connected to the positive (+) and negative (−) voltage output therapeutic electrodes 1730 and 1740 and drives the inputs of the first channel of analog-to-digital converter 1750. In some embodiments, a probe, such as a Tektronix P6015A Passive High Voltage Probe (not shown) is connected to the positive (+) and negative (−) voltage output therapeutic electrodes 1730 and 1740, and drives the inputs of analog-to-digital converter 1750.

In addition, analog-to-digital converter 1750 is configured to generate a first digital output at output terminal 1735 representing the voltage difference between the positive (+) and negative (−) voltage output therapeutic electrodes 1730 and 1740. When used in the nsPEF treatment system 1550 of FIG. 15, the first digital output may be used as a feedback signal for controller 1575. In some embodiments, analog-to-digital converter 1750 generates the first digital output based on either, but not both, of the voltages at the positive (+) and negative (−) voltage output therapeutic electrodes 1730 and 1740.

In this embodiment, analog-to-digital converter 1750 also includes a second channel having inputs which are respectively connected to the current monitors 1760 and 1770, and the current monitors 1760 and 1770 are respectively connected to the positive (+) and negative (−) voltage output therapeutic electrodes 1730 and 1740. In some embodiments, a second differential buffer (not shown) is connected to the current monitors 1760 and 1770 and drives the inputs of the second channel of analog-to-digital converter 1750.

In addition, analog-to-digital converter 1750 is configured to generate a second digital output at output terminal 1765 representing the current difference between the currents flowing through positive (+) and negative (−) voltage output therapeutic electrodes 1730 and 1740. When used in the nsPEF treatment system 1550 of FIG. 15, the second digital output may be used as a feedback signal for controller 1575. In some embodiments, analog-to-digital converter 1750 generates the second digital output based on either, but not both, of inputs from the current monitors 1760 and 1770.

In this embodiment, analog-to-digital converter 1750 also includes a third channel having inputs which are respectively connected to the thermal sensors 1780 and 1790, and the thermal sensors 1780 and 1790 are respectively thermally coupled to the positive (+) and negative (−) voltage output therapeutic electrodes 1730 and 1740.

In some embodiments, a third low input impedance differential buffer (not shown) is connected to the thermal sensors 1780 and 1790, and drives the inputs of the third channel of analog-to-digital converter 1750.

Analog-to-digital converter 1750 may be configured to generate a third digital output at output terminal 1785 representing a temperature of at least one of positive (+) and negative (−) voltage output therapeutic electrodes 1730 and 1740. When used in the nsPEF treatment system 1550 of FIG. 15, the third digital output may be used as a feedback signal for controller 1575. In some embodiments, analog-to-digital converter 1750 generates the third digital output based on either, but not both, of inputs from the thermal sensors 1780 and 1790.

In some embodiments, the thermal sensors 1780 and 1790 are not coupled to the positive (+) and negative (−) voltage output therapeutic electrodes 1730 and 1740, but are, instead, coupled to first and second pins which contact the patient. In such embodiments, the first and second pins may contact the patient to sense tissue temperature, and the therapeutic electrodes 1730 and 1740 may contact the patient to deliver nsPEF pulses.

In some embodiments, one or more thermal sensors separate from electrode 1565 contact the patient and have a cable providing thermal information to controller 1575, where at least part of the cable is different from the cable connecting electrode 1565 and controller 1575.

In some embodiments, electrode 1565 includes at least one laser thermometer, such as an IR laser thermometer, which provides thermal information corresponding with that of thermal sensors 1780 and 1790.

In various embodiments, pulse generator 1700 generates any one, two, or all of the first, second, and third digital outputs. In some embodiments, one or more single channel analog-to-digital converters are used instead of or in addition to analog-to-digital converter 1750.

Figure 18:
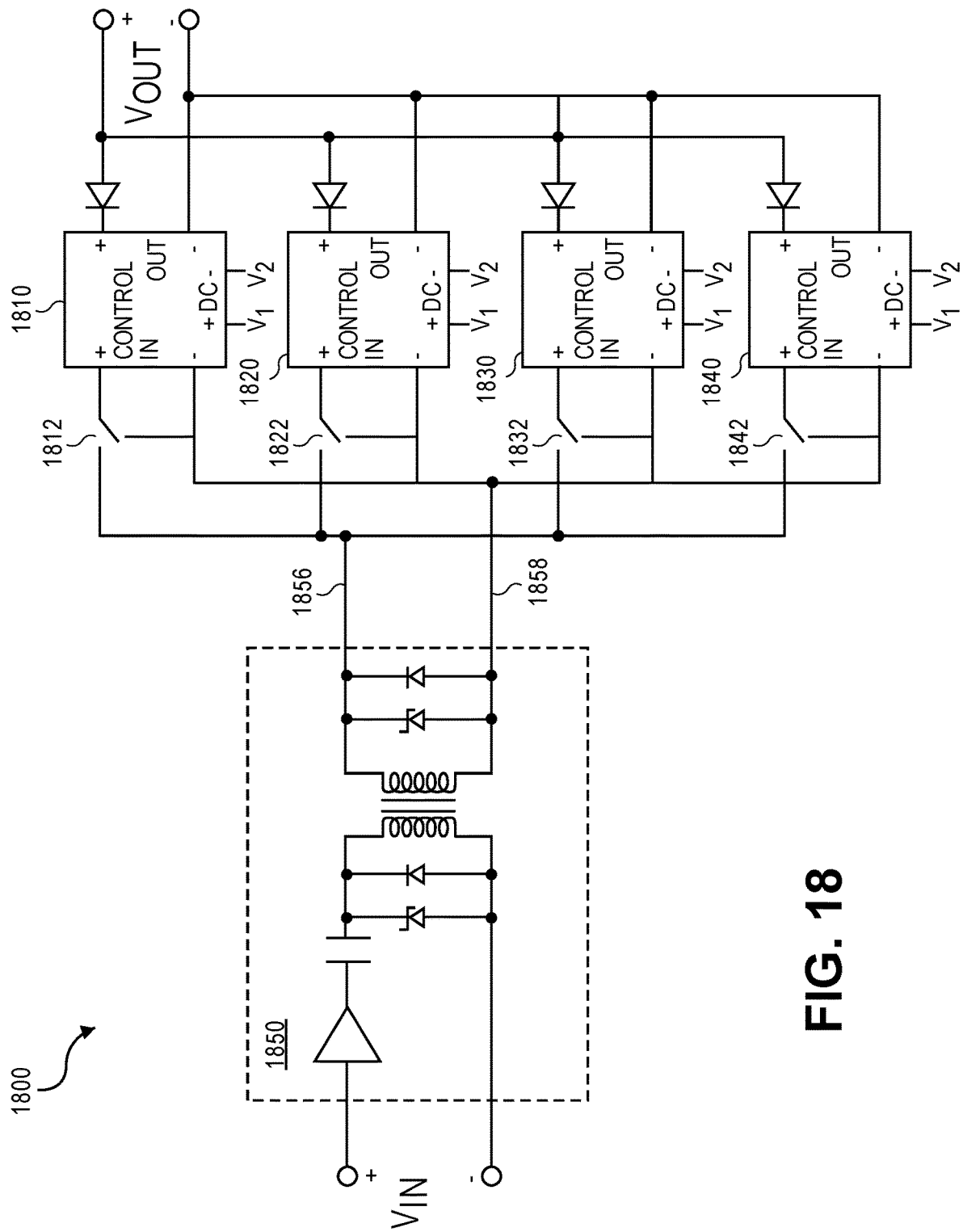
FIG. 18 is a schematic illustration of an alternative pulse generator which may be used in the nsPEF treatment system of FIG. 15.

FIG. 18 illustrates an alternative pulse generator 1800 which may be used as pulse generator 1555 of nsPEF treatment system 1550 illustrated in FIG. 15. Pulse generator 1800 may have features similar to or identical to other pulse generator circuits discussed herein. For example, pulse generator circuit 1800 may have features similar to or identical to pulse generator circuit 700 of FIG. 7.

For example, pulse generator 1800 includes the driver circuit 1850 which may be similar to or identical to driver 750 of pulse generator circuit 700. In addition, pulse generator 1800 includes pulse generator circuits 1810, 1820, 1830, and 1840, which may respectively be similar or identical to pulse generator circuits 710, 720, 730, and 740.

In some embodiments, it may be desirable to select which of pulse generator circuits 1810, 1820, 1830, and 1840 to use for causing an nsPEF pulse to be generated. For example, prior to using nsPEF treatment system 1550 for treatment of a patient, it may be desirable to verify correct operation of each of pulse generator circuits 1810, 1820, 1830, and 1840.

As illustrated, the negative control input terminals of each of pulse generator circuits 1810, 1820, 1830, and 1840 are connected with conductor 1858. Pulse generator 1800 also includes switches 1812, 1822, 1832, and 1842, which are respectively connected to the positive control input terminals of pulse generator circuits 1810, 1820, 1830, and 1840. Switches 1812, 1822, 1832, and 1842 are respectively configured to selectively connect the positive control input terminals of pulse generator circuits 1810, 1820, 1830, and 1840 with either conductor 1856 or conductor 1858 according to control signals (not illustrated) from a controller, such as controller 1575 of FIG. 15.

To generate an nsPEF pulse, the controller determines which of pulse generator circuits 1810, 1820, 1830, and 1840 is to be used. Based on the determination, the controller connects one or more of the positive control input terminals of pulse generator circuits 1810, 1820, 1830, and 1840 to conductor 1856 by controlling the state of switches 1812, 1822, 1832, and 1842. The controller then generates a signal causing driver circuit 1850 to receive an input signal pulse at input port Vin. In response to the input signal pulse, driver circuit 1850 generates a driving signal pulse across conductors 1856 and 1858. The driving signal pulse is selectively transmitted to the one or more of pulse generator circuits 1810, 1820, 1830, and 1840 determined to be used according to the state of the switches 1812, 1822, 1832, and 1842. In addition, according to the state of the switches 1812, 1822, 1832, and 1842, the driving signal is not transmitted to pulse generator circuits 1810, 1820, 1830, and 1840, which are not determined to be used. In response to the driving signal pulse, the determined one or more of pulse generator circuits 1810, 1820, 1830, and 1840 collectively deliver an nsPEF pulse to an electrode, such as electrode 1565 of FIG. 15.

Figure 19:
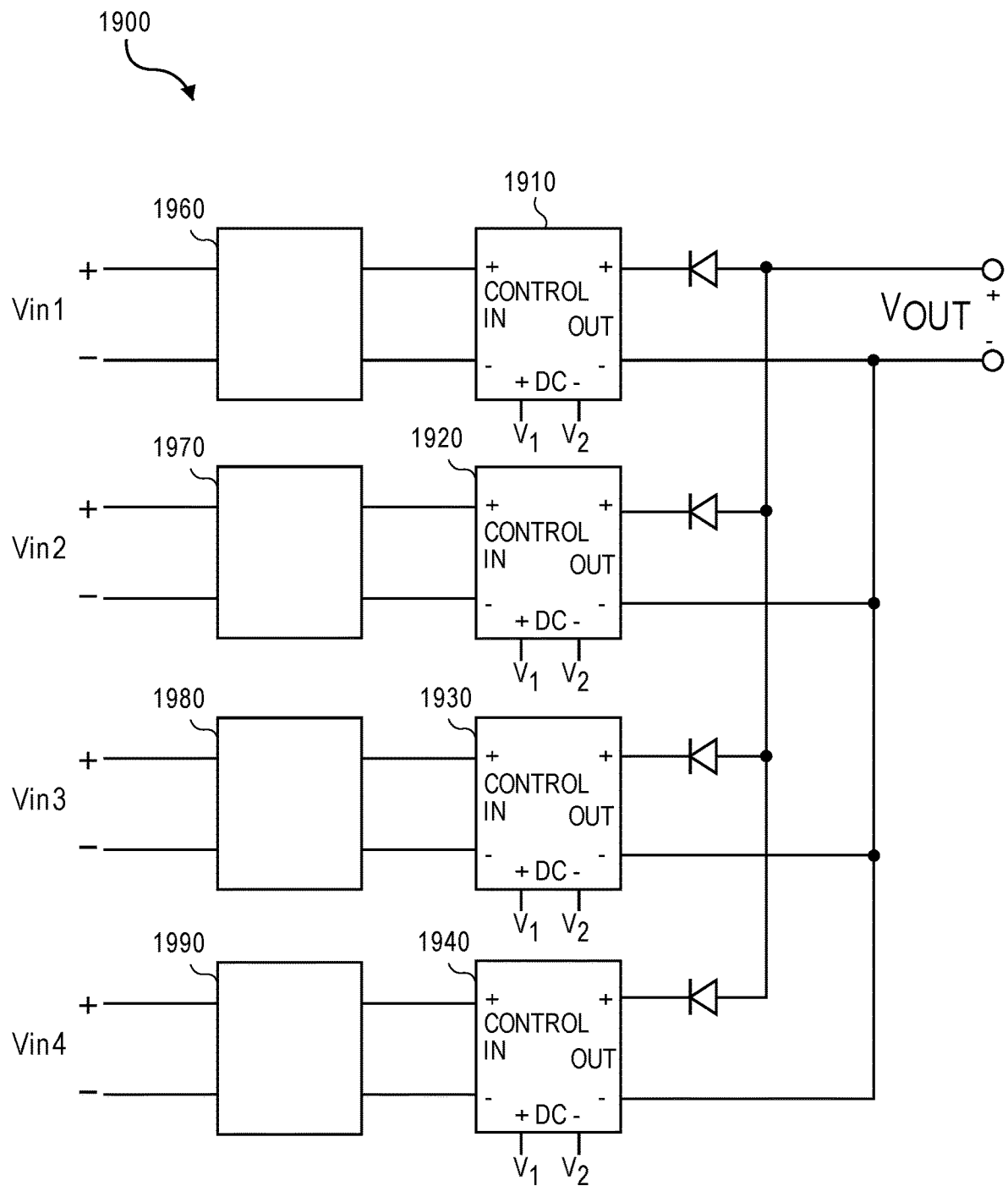
FIG. 19 is a schematic illustration of another alternative pulse generator which may be used in the nsPEF treatment system of FIG. 15.

FIG. 19 illustrates an alternative pulse generator 1900 which may be used as pulse generator 1555 of nsPEF treatment system 1550 illustrated in FIG. 15. Pulse generator 1900 may have features similar to or identical to other pulse generator circuits discussed herein. For example, pulse generator circuit 1900 may have features similar to or identical to pulse generator circuit 700 of FIG. 7.

For example, pulse generator 1900 includes driver circuits 1960, 1970, 1980, and 1990, which may be similar to or identical to driver 750 of pulse generator circuit 700. In addition, pulse generator 1900 includes pulse generator circuits 1910, 1920, 1930, and 1940, which may respectively be similar or identical to pulse generator circuits 710, 720, 730, and 740.

As illustrated, the positive and negative control input terminals of each of pulse generator circuits 1910, 1920, 1930, and 1940 are respectively connected with conductors from one of the driver circuits 1960, 1970, 1980, and 1990. Each of driver circuits 1960, 1970, 1980, and 1990 has a separate Vin input port. Therefore, a controller, such as controller 1575 of FIG. 15, may generate one or more signals causing one or more of driver circuits 1960, 1970, 1980, and 1990 to receive an input signal pulse at their respective Vin input ports.

To generate an nsPEF pulse, the controller determines which of pulse generator circuits 1910, 1920, 1930, and 1940 is to be used. Based on the determination, the controller generates one or more signals causing one or more of driver circuits 1960, 1970, 1980, and 1990 to receive an input signal pulse at their respective Vin input ports.

In some embodiments, the input signal pulses are synchronous. In some embodiments, the input signal pulses are asynchronous. In some embodiments, the input signal pulses have substantially equal pulse widths. In some embodiments, the input signal pulses have different pulse widths.

In response to the one or more received input signal pulses, the driver circuits 1960, 1970, 1980, and 1990 having received an input signal pulse each generate a driving signal pulse for the corresponding one of pulse generator circuits 1910, 1920, 1930, and 1940. In response to the driving signal pulses, the determined one or more of pulse generator circuits 1910, 1920, 1930, and 1940 deliver an nsPEF pulse to an electrode, such as electrode 1565 of FIG. 15.

Figure 20:
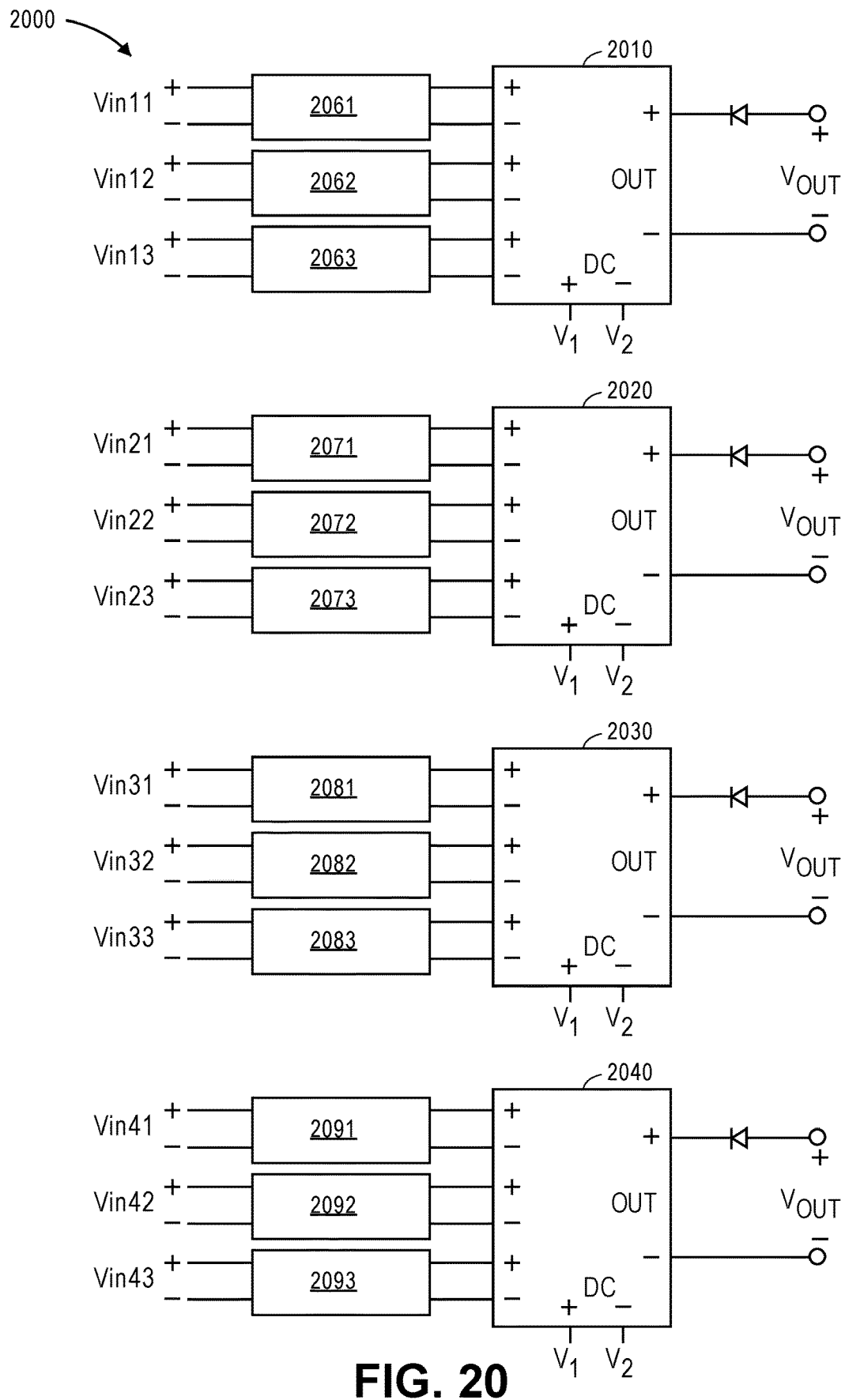
FIG. 20 is a schematic illustration of yet another alternative pulse generator which may be used in the nsPEF treatment system of FIG. 15.

FIG. 20 illustrates an alternative pulse generator 2000 which may be used as pulse generator 1555 of nsPEF treatment system 1550 illustrated in FIG. 15. Pulse generator 2000 may have features similar to or identical to other pulse generator circuits discussed herein. For example, pulse generator circuit 2000 may have features similar to or identical to pulse generator circuit 700 of FIG. 7.

For example, pulse generator 2000 includes pulse generator circuits 2010, 2020, 2030, and 2040, which may respectively be similar or identical to pulse generator circuits 710, 720, 730, and 740. In addition, pulse generator 2000 includes driver circuits 2061, 2062, 2063, 2071, 2072, 2073, 2081, 2082, 2083, 2091, 2092, and 2093, which may be similar to or identical to driver 750 of pulse generator circuit 700.

As illustrated, each of pulse generator circuits 2010, 2020, 2030, and 2040 has three control input ports, where each control input port has a corresponding positive and negative terminal. An embodiment of a pulse generator circuit which may be used for pulse generator circuits 2010, 2020, 2030, and 2040 is discussed below with reference to FIG. 21. The positive and negative control input terminals of each control input port are respectively connected with conductors from one of driver circuits 2061, 2062, 2063, 2071, 2072, 2073, 2081, 2082, 2083, 2091, 2092, and 2093, and each of driver circuits 2061, 2062, 2063, 2071, 2072, 2073, 2081, 2082, 2083, 2091, 2092, and 2093, has a separate Vin input port. Therefore, a controller, such as controller 1575 of FIG. 15, may generate one or more signals causing one or more of driver circuits 2061, 2062, 2063, 2071, 2072, 2073, 2081, 2082, 2083, 2091, 2092, and 2093, to receive an input signal pulse at their respective Vin input ports.

Figure 21:
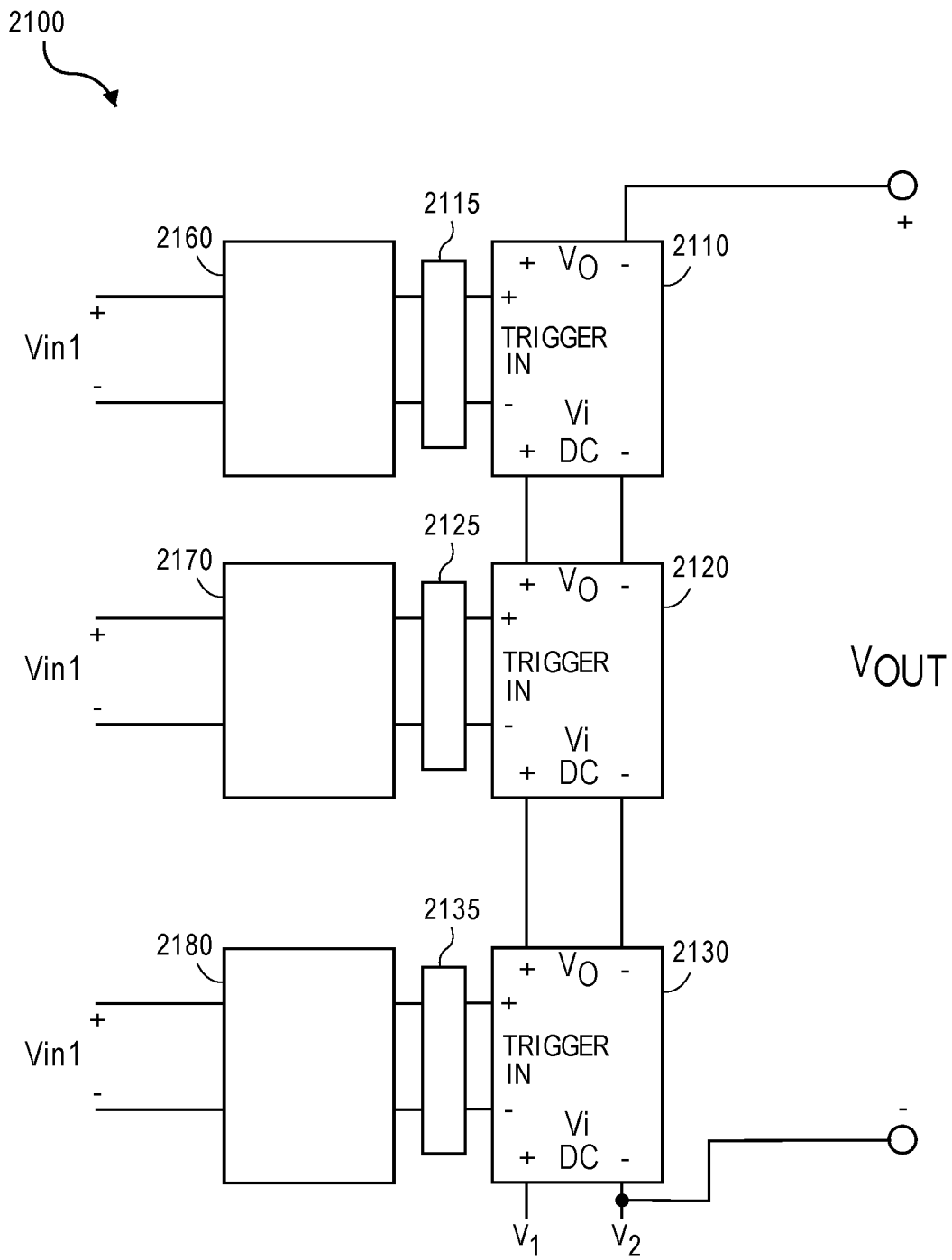
FIG. 21 is a schematic illustration of an embodiment of pulse generator circuit which may be used for the pulse generator circuits of FIG. 20.

FIG. 21 illustrates an embodiment of pulse generator circuit 2100 which may be used for pulse generator circuits 2010, 2020, 2030, and 2040 of FIG. 20. Pulse generator circuit 2100 may have features similar to or identical to other pulse generator circuits discussed herein. For example, pulse generator circuit 2100 may have features similar to or identical to pulse generator circuit 800 of FIG. 8.

For example, pulse generator 2100 includes pulse generator stages 2110, 2120, and 2130, which may respectively be similar or identical to pulse generator stages 810, 820, and 830. In addition, pulse generator 2100 includes driver circuits 2160, 2170, and 2180, which may be similar to or identical to driver 850 of pulse generator circuit 800. Furthermore, pulse generator 2100 includes optional common mode chokes 2115, 2125, and 2135, which may be similar or identical to optional common mode chokes 815, 825, and 835.

As illustrated, the positive and negative trigger input terminals of each of pulse generator stages 2110, 2120, and 2130 are respectively connected with conductors from one of the driver circuits 2160, 2170, and 2180 through one of common mode chokes 2115, 2125, and 2135. In alternative embodiments, driver circuits 2160, 2170, and 2180 are not included, and each of pulse generator stages 2110, 2120, and 2130 are respectively driven by a driver circuit, such as one of driver circuits 2061, 2062, 2063, 2071, 2072, 2073, 2081, 2082, 2083, 2091, 2092, and 2093 of FIG. 20. In this embodiment, each of driver circuits 2160, 2170, and 2180 has a separate Vin input port, and receives an input pulse from a driver circuit, such as one of driver circuits 2061, 2062, 2063, 2071, 2072, 2073, 2081, 2082, 2083, 2091, 2092, and 2093 of FIG. 20.

Therefore, a controller, such as controller 1575 of FIG. 15, may generate one or more signals causing one or more of driver circuits 2160, 2170, and 2180 to receive an input signal pulse at their respective Vin input ports.

To generate an nsPEF pulse using pulse generator 2000 of FIG. 20, the controller determines which one or more pulse generator stages 2110, 2120, and 2130 of which pulse generator circuits 2010, 2020, 2030, and 2040 are to be used. Based on the determination, the controller generates one or more signals causing one or more of driver circuits 2061, 2062, 2063, 2071, 2072, 2073, 2081, 2082, 2083, 2091, 2092, and 2093 to receive an input signal pulse at their respective Vin input ports. In response to the one or more received input signal pulses, the driver circuits 2061, 2062, 2063, 2071, 2072, 2073, 2081, 2082, 2083, 2091, 2092, and 2093 having received an input signal pulse each generate a driving signal pulse for the corresponding one of pulse generator stages 2110, 2120, and 2130 of the corresponding one of pulse generator circuits 2010, 2020, 2030, and 2040. In response to the driving signal pulse, the determined one or more pulse generator stages collectively deliver an nsPEF pulse to an electrode, such as electrode 1565 of FIG. 15.

Figure 22:
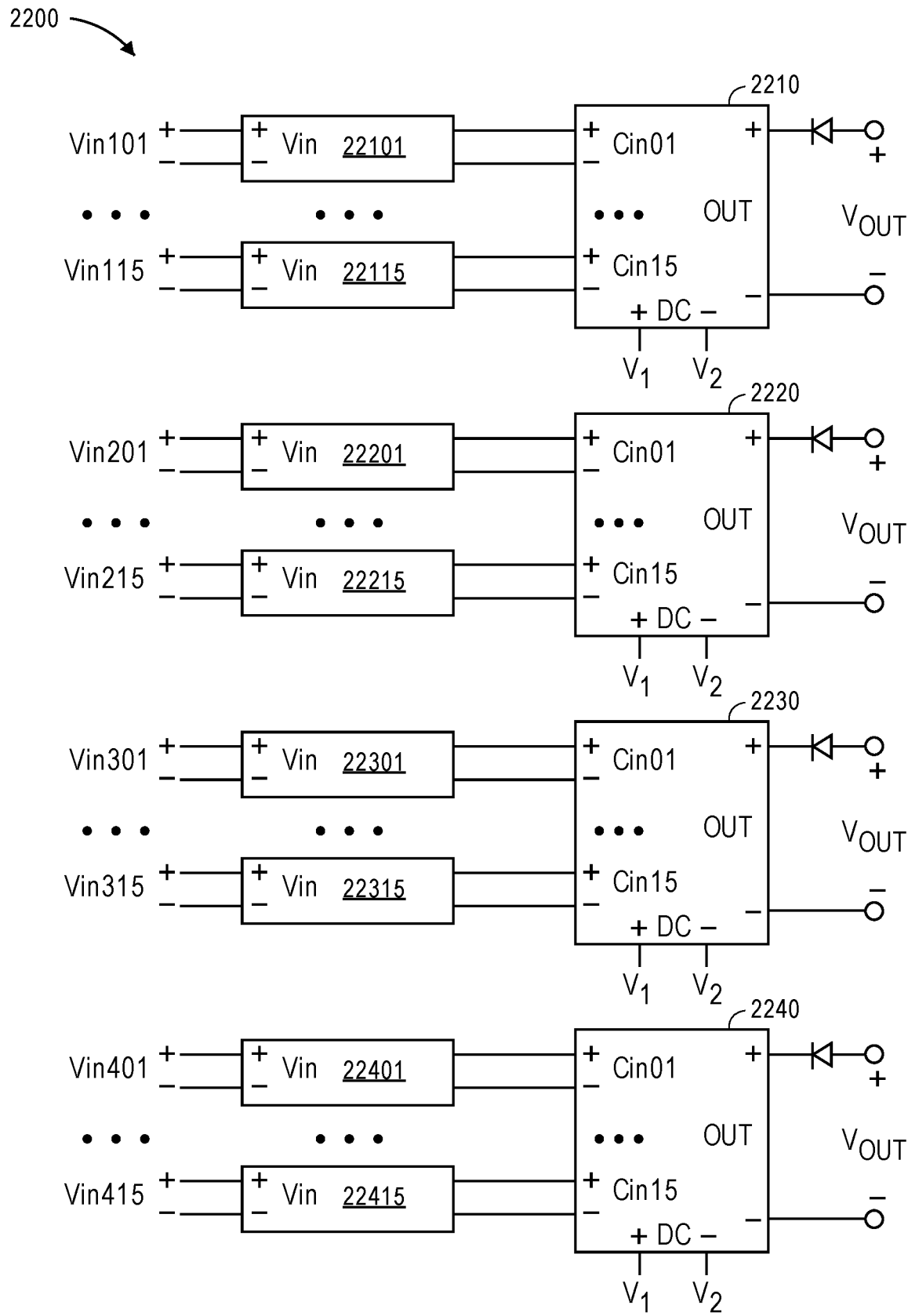
FIG. 22 is a schematic illustration of an alternative pulse generator which may be used in the nsPEF treatment system of FIG. 15.

FIG. 22 illustrates an alternative pulse generator 2200 which may be used as pulse generator 1555 of nsPEF treatment system 1550 illustrated in FIG. 15. Pulse generator 2200 may have features similar to or identical to other pulse generator circuits discussed herein. For example, pulse generator circuit 2200 may have features similar to or identical to pulse generator circuit 700 of FIG. 7.

For example, pulse generator 2200 includes pulse generator circuits 2210, 2220, 2230, and 2240, which may respectively be similar or identical to pulse generator circuits 710, 720, 730, and 740. In addition, pulse generator 2200 includes driver circuits 22101 . . . 22115, 22201 . . . 22215, 22301 . . . 22315, and 22401 . . . 22415, which may be similar to or identical to driver 750 of pulse generator circuit 700.

As illustrated, each of pulse generator circuits 2210, 2220, 2230, and 2240 has 15 control input ports Cin01 . . . Cin15, where each control input port has a corresponding positive and negative terminal. An embodiment of a pulse generator circuit which may be used for pulse generator circuits 2210, 2220, 2230, and 2240 is discussed below with reference to FIG. 23. The positive and negative control input terminals of each control input port are respectively connected with conductors from one of driver circuits 22101 . . . 22115, 22201 . . . 22215, 22301 . . . 22315, and 22401 . . . 22415, and each of driver circuits 22101 . . . 22115, 22201 . . . 22215, 22301 . . . 22315, and 22401 . . . 22415, has a separate Vin input port. Therefore, a controller, such as controller 1575 of FIG. 15, may generate one or more signals causing one or more of driver circuits 22101 . . . 22115, 22201 . . . 22215, 22301 . . . 22315, and 22401 . . . 22415, to receive an input signal pulse at their respective Vin input ports.

Figure 23:
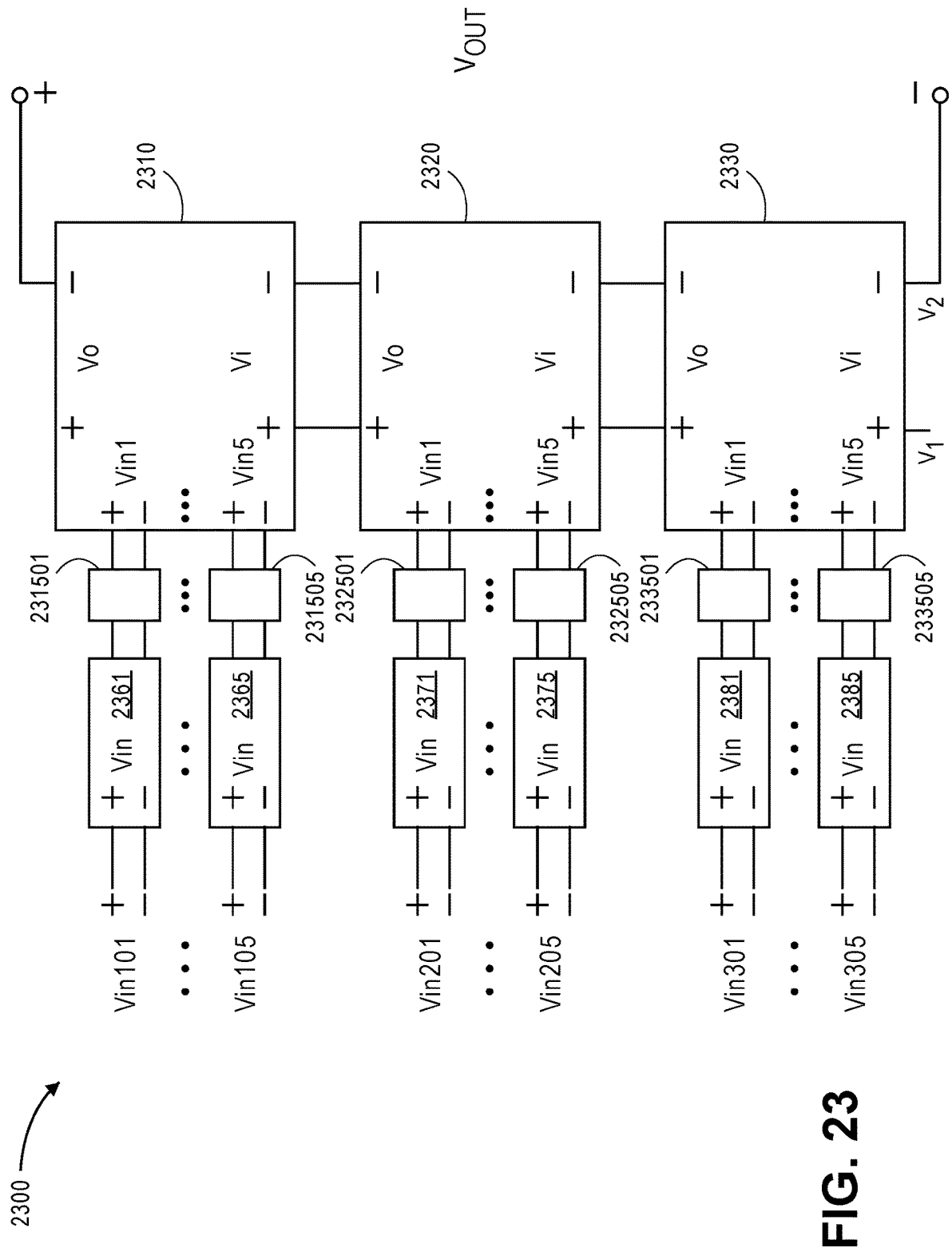
FIG. 23 is a schematic illustration of an embodiment of pulse generator circuit which may be used for the pulse generator circuits of FIG. 22.

FIG. 23 illustrates an embodiment of pulse generator circuit 2300 which may be used for pulse generator circuits 2210, 2220, 2230, and 2240 of FIG. 22. Pulse generator circuit 2300 may have features similar to or identical to other pulse generator circuits discussed herein. For example, pulse generator circuit 2300 may have features similar to or identical to pulse generator circuit 800 of FIG. 8.

For example, pulse generator 2300 includes pulse generator stages 2310, 2320, and 2330, which may respectively be similar or identical to pulse generator stages 810, 820, and 830. An embodiment of a pulse generator stage which may be used for stages 2310, 2320, and 2330 is discussed below with reference to FIG. 24. Pulse generator 2300 also includes driver circuits 2361 . . . 2365, 2371 . . . 2375, 2381 . . . 2385, which may be similar to or identical to driver 850 of pulse generator circuit 800. Furthermore, pulse generator 2300 includes optional common mode chokes 231501 . . . 223505, 232501 . . . 232505, and 233501 . . . 233505, which may be similar or identical to optional common mode chokes 815, 825, and 835.

As illustrated, each of pulse generator stages 2310, 2320, and 2330 has five input ports Vin1 . . . Vin5, and the positive and negative trigger input terminals of each input port is connected with conductors from one of the driver circuits 2361 . . . 2365, 2371 . . . 2375, 2381 . . . 2385 through one of common mode chokes 231501 . . . 223505, 232501 . . . 232505, and 233501 . . . 233505. In alternative embodiments, driver circuits 2361 . . . 2365, 2371 . . . 2375, 2381 . . . 2385 are not included, and each of pulse generator stages 2310, 2320, and 2330 are respectively driven by a driver circuit, such as one of driver circuits 22101 . . . 22115, 22201 . . . 22215, 22301 . . . 22315, and 22401 . . . 22415 of FIG. 22. In this embodiment, each of driver circuits 2361 . . . 2365, 2371 . . . 2375, 2381 . . . 2385 has a separate Vin input port, and receives an input pulse from a driver circuit, such as one of driver circuits 22101 . . . 22115, 22201 . . . 22215, 22301 . . . 22315, and 22401 . . . 22415 of FIG. 22.

Figure 24:
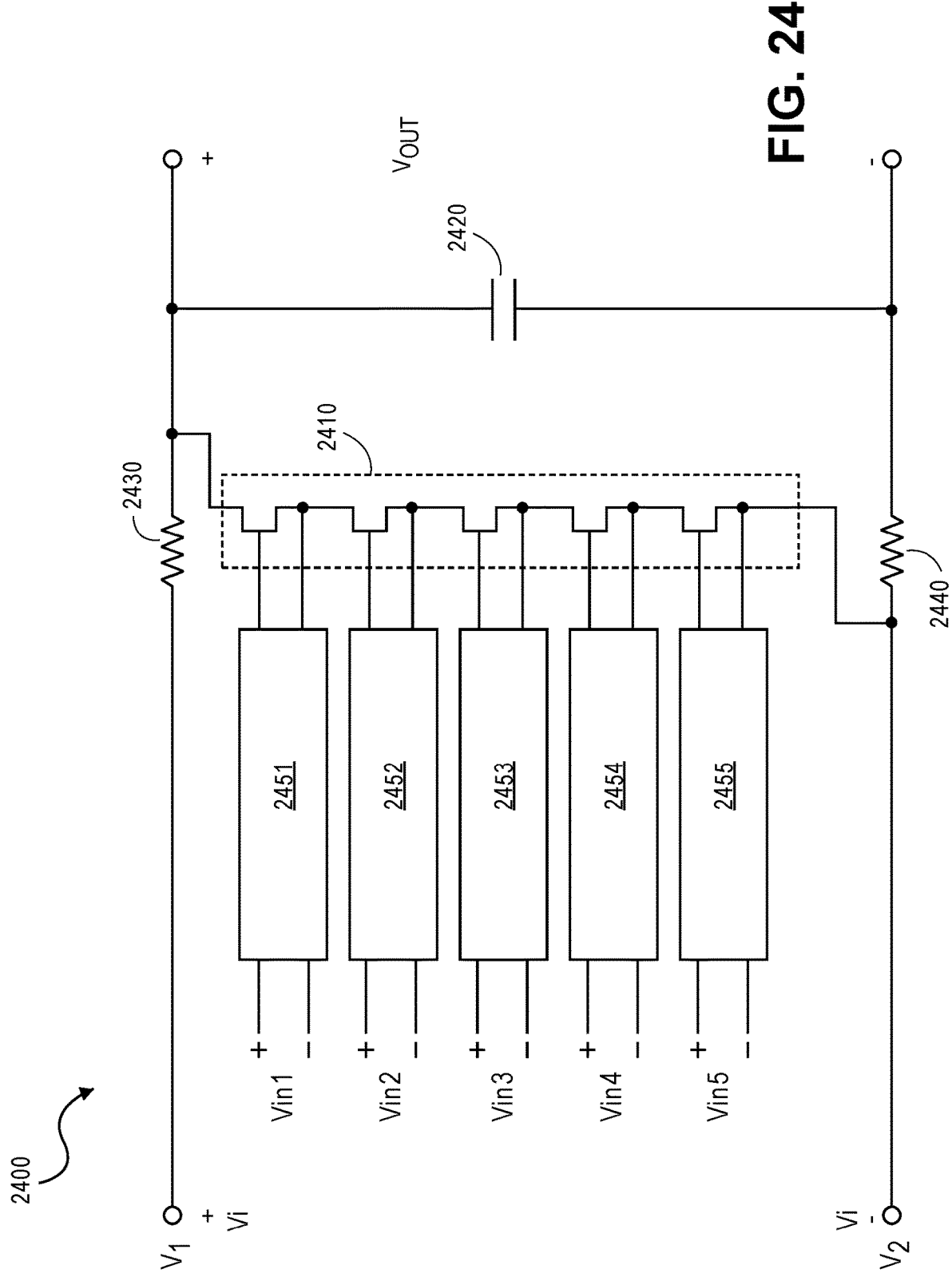
FIG. 24 is a schematic illustration of a pulse generator stage which may be used as one of the pulse generator stages of the pulse generator circuit illustrated in FIG. 23.

FIG. 24 illustrates a pulse generator stage 2400 which may be used as one of the pulse generator stages 2310, 2320, and 2330 of pulse generator circuit 2300 shown in FIG. 23. Pulse generator stage 2400 may have features similar to or identical to other pulse generator stages discussed herein. For example, pulse generator circuit 2400 may have features similar to or identical to pulse generator stage 900 of FIG. 9. For example, pulse generator circuit 2400 includes resistors 2430 and 2440, which may respectively be similar or identical to resistors 930 and 940 of pulse generator stage 900 of FIG. 9. Also, capacitor 2420 of pulse generator stage 2400 may be similar or identical to capacitor 930 of pulse generator stage 900 of FIG. 9.

Pulse generator stage 2400 receives five trigger pulses across input ports Vin1, Vin2, Vin3, Vin4, and Vin5, and generates output voltages at output port Vout in response to the received trigger pulses.

Switch drivers 2451, 2452, 2453, 2454, and 2455 are configured to receive the trigger pulses, and to generate control signals for the switches of switch stack 2410 in response to the received trigger pulses. Switch drivers 2451, 2452, 2453, 2454, and 2455 may have features similar to or identical to other pulse generator stages discussed herein. For example, Switch drivers 2451, 2452, 2453, 2454, and 2455 may have features similar to or identical to pulse switch drivers 950 of FIG. 9.

In alternative embodiments, switch drivers 2451, 2452, 2453, 2454, and 2455 are not included, and each of the switches of switch stack 2410 are respectively driven by a driver circuit, such as one of driver circuits 2361 . . . 2365, 2371 . . . 2375, 2381 . . . 2385 of FIG. 23 or one of driver circuits 22101 . . . 22115, 22201 . . . 22215, 22301 . . . 22315, and 22401 . . . 22415 of FIG. 22.

Therefore, a controller, such as controller 1575 of FIG. 15, may generate a group of signals causing one or more groups of driver circuits 22101 . . . 22115, 22201 . . . 22215, 22301 . . . 22315, and 22401 . . . 22415 of FIG. 22 to receive an input signal pulse at their respective Vin input ports, where each group of driver circuits includes five driver circuits respectively configured to directly or indirectly drive one of the switches of one of the instances of pulse generator stage 2400.

To generate an nsPEF pulse using pulse generator 2200 of FIG. 22, the controller determines which one or more pulse generator stages 2310, 2320, and 2330 of which pulse generator circuits 2210, 2220, 2230, and 2240 are to be used. Based on the determination, the controller generates one or more groups of signals causing the driver circuits of one or more groups of driver circuits 22101 . . . 22115, 22201 . . . 22215, 22301 . . . 22315, and 22401 . . . 22415 to receive an input signal pulse at their respective Vin input ports. In response to the one or more received input signal pulses, the driver circuits 22101 . . . 22115, 22201 . . . 22215, 22301 . . . 22315, and 22401 . . . 22415 having received an input signal pulse each generate a driving signal pulse for the corresponding one of the switches of one of the instances of pulse generator stage 2400. In response to the driving signal pulse, the determined one or more pulse generator stages collectively deliver an nsPEF pulse to an electrode, such as electrode 1565 of FIG. 15.

Figure 25:
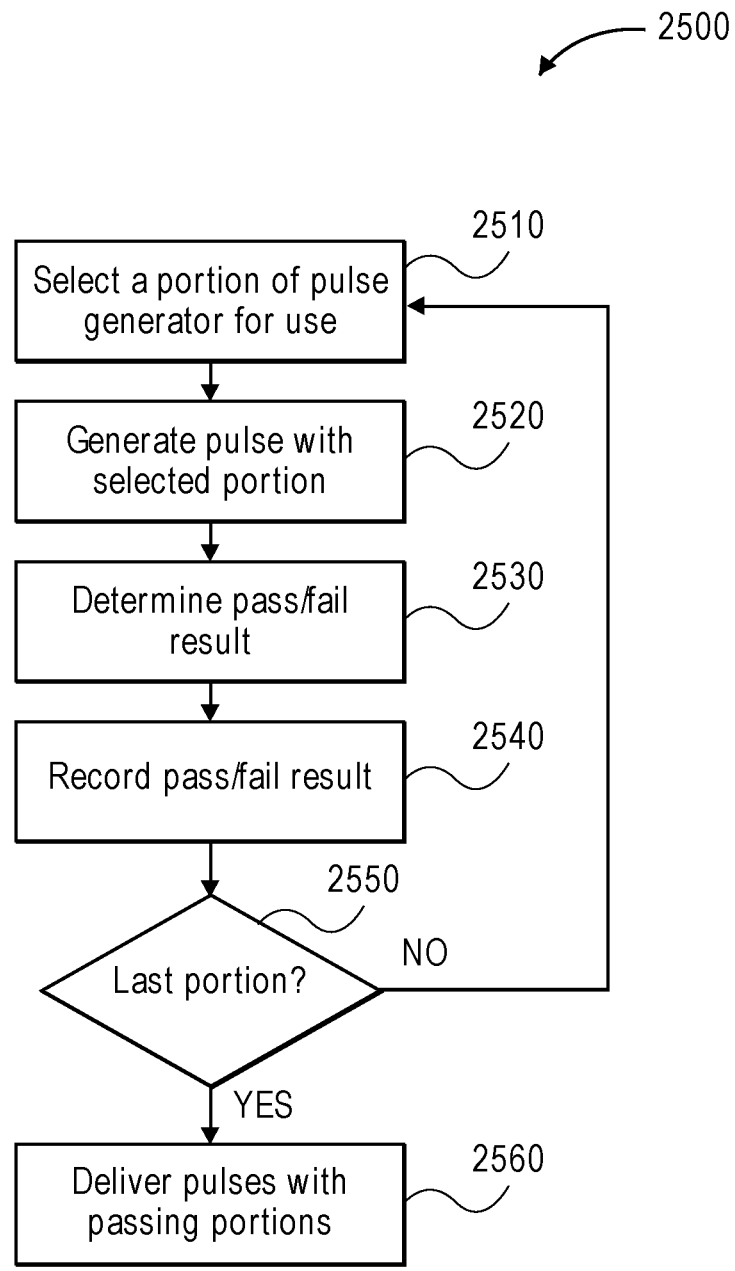
FIG. 25 is a flowchart illustrating a method of using a pulse generator system.

FIG. 25 is a flowchart illustrating a method 2500 of using a pulse generator system, such as any of the nsPEF systems described herein. The method 2500 may, for example, be used as part of a self-test routine performed prior to or as part of treating a patient.

At 2510, a processor of the pulse generator system selects a portion of the pulse generator system to be used. The selecting may, for example, include selecting a next portion of the pulse generator system, where the next portion has not been previously used in the self-test routine. In some embodiments, a portion of the pulse generator system may include one or more pulse generators of a plurality or of a larger plurality of pulse generators.

At 2520, the processor generates a pulse with the portion of the pulse generator system selected at 2510. For example, the processor may operate switches to connect the selected portion to one or more drivers, and subsequently deliver a signal to the one or more drivers. If the selected portion is operational, the delivered signal causes the selected portion to generate a pulse, for example, as discussed above. Alternatively, the processor may select one or more drivers associated with the selected portion, and subsequently deliver a signal to the one or more drivers. If the selected portion is operational, the delivered signal causes the selected portion to generate a pulse, for example, as discussed above.

At 2530, the processor determines whether the selected portion is operational based on whether it successfully generated a pulse in response to the delivered signal. For example, the processor may receive a signal indicating a current or a voltage from an electrode configured to deliver the pulse to a patient or to a load. The processor may compare the indicated current or voltage with a limit to determine whether the selected portion is operational.

At 2540, the processor records a result of the determination in a memory of the processor. For example, if, at 2530, the processor determines that the selected portion did not successfully generate a pulse, at 2540, the processor may store in the memory an indication that the selected portion failed. Likewise, if, at 2530, the processor determines that the selected portion did successfully generate a pulse, at 2540, the processor may store in the memory an indication that the selected portion passed.

At 2550, the processor determines whether an additional pulse generator portion is to be tested. If an additional pulse generator portions is to be tested, the method 2500 returns to 2510, where a next portion of the pulse generator to be tested is determined. If an additional pulse generator portion is not to be tested, the method continues to 2560.

At 2560, the pulse generator system is used to deliver pulses to a patient. When used, the pulse generator system delivers pulses with the pulse generator portions which were determined, at 2530, to have been operational, and does not use the pulse generator portions which were determined, at 2530, to have not been operational.

Figure 26:
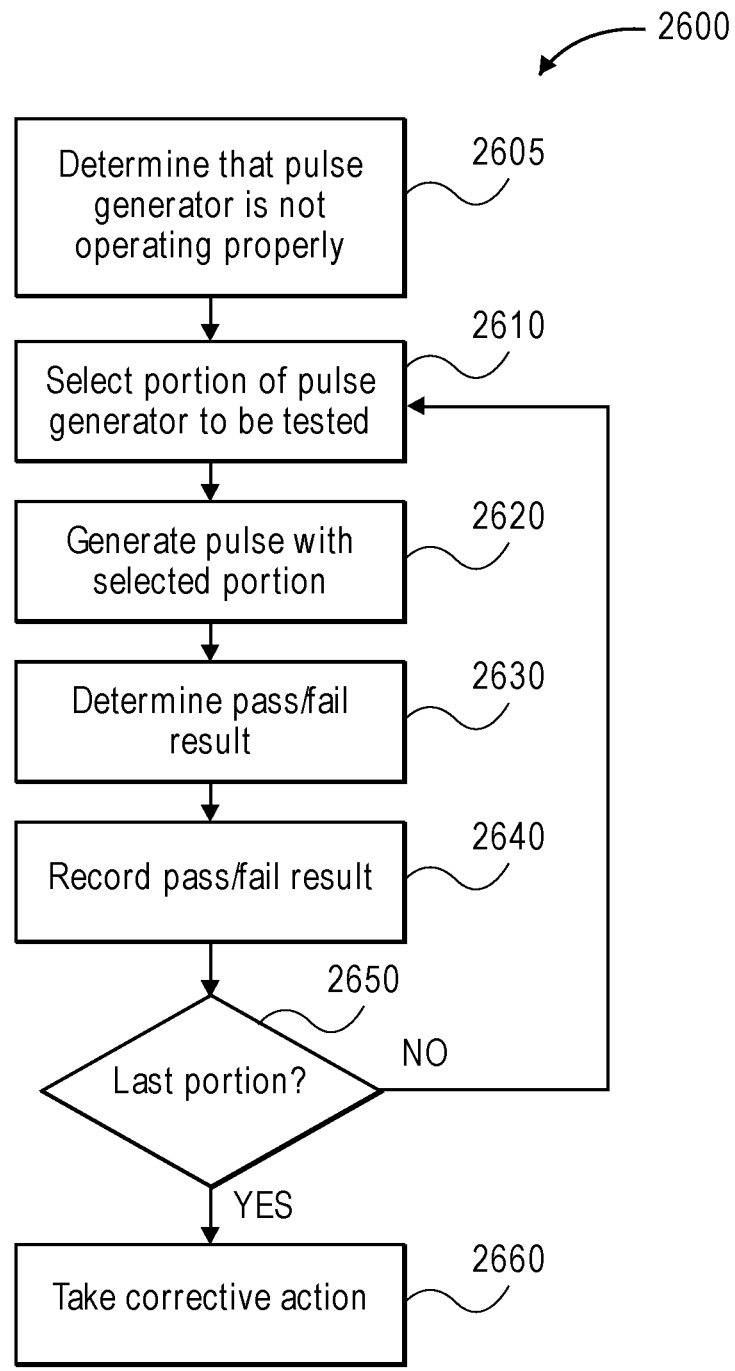
FIG. 26 is a flowchart illustrating a method of using a pulse generator system.

FIG. 26 is a flowchart illustrating a method 2600 of using a pulse generator system, such as any of the nsPEF systems described herein. The method 2600 may, for example, be used as part of a fault isolation procedure.

At 2605, a determination is made that the pulse generator is not operating properly.

At 2610, a processor of the pulse generator system determines a portion of the pulse generator system to be tested. The determination may, for example, include selecting a next portion of the pulse generator system, where the next portion has not been previously tested in the method.

At 2620, the processor generates a pulse with the portion of the pulse generator system determined at 2610. For example, the processor may operate switches to connect the selected portion to one or more drivers, and subsequently deliver a signal to the one or more drivers. If the selected portion is operational, the delivered signal causes the selected portion to generate a pulse, for example, as discussed above. Alternatively, the processor may select one or more drivers associated with the selected portion, and subsequently deliver a signal to the one or more drivers. If the selected portion is operational, the delivered signal causes the selected portion to generate a pulse, for example, as discussed above.

At 2630, the processor determines whether the selected portion is operational based on whether it successfully generated a pulse in response to the delivered signal. For example, the processor may receive a signal indicating a current or a voltage from an electrode configured to deliver the pulse to a patient or to a load. The processor may compare the indicated current or voltage with a limit to determine whether the selected portion is operational.

At 2640, the processor records a result of the determination in a memory of the processor. For example, if, at 2630, the processor determines that the selected portion did not successfully generate a pulse, at 2640, the processor may store in the memory an indication that the selected portion failed. Likewise, if, at 2630, the processor determines that the selected portion did successfully generate a pulse, at 2640, the processor may store in the memory an indication that the selected portion passed.

At 2650, the processor determines whether an additional pulse generator portion is to be tested. If an additional pulse generator portions is to be tested, the method 2600 returns to 2610, where a next portion of the pulse generator to be tested is determined. If an additional pulse generator portion is not to be tested, the method continues to 2660.

At 2660, corrective action is taken. For example, a component of the pulse generator system including a failed pulse generator portion may be replaced. Alternatively, the processor may indicate or mark a pulse generator portion identified at 2630 as having failed as not being available for use during subsequent treatment of a patient.

Figure 27:
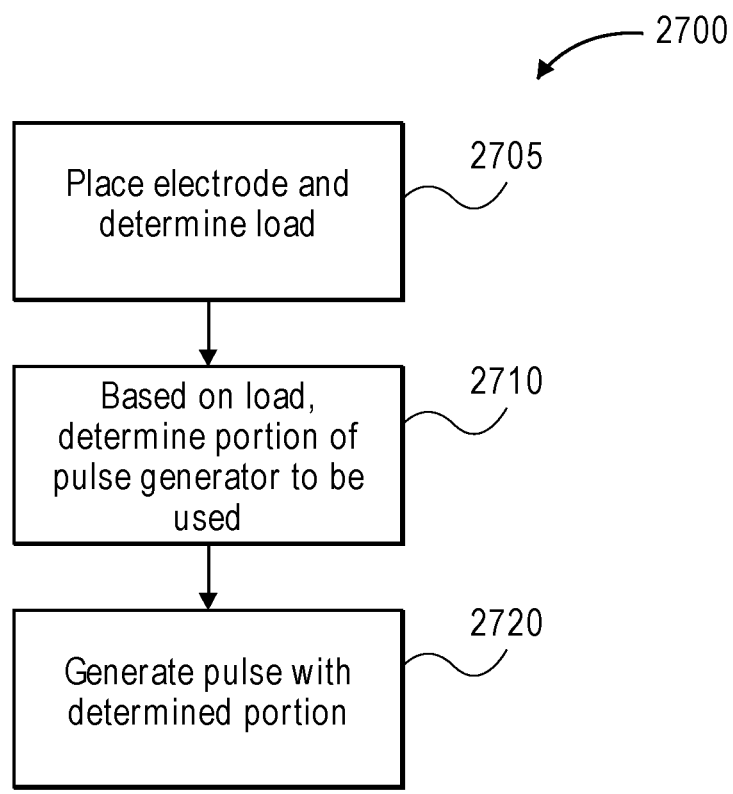
FIG. 27 is a flowchart illustrating a method of using a pulse generator system

FIG. 27 is a flowchart illustrating a method 2700 of using a pulse generator system, such as any of the nsPEF systems described herein. The method 2700 may, for example, be performed prior to or as part of treating a patient.

At 2705, an electrode, configured to deliver pulses, is placed on or in a patient. In addition, a processor of the pulse generator system determines an electrical load or impedance presented to the pulse generator system by the patient. For example, the processor may deliver a pulse to the electrode, monitor or measure the current and/or voltage, and determine the impedance or electrical load by dividing the delivered voltage by the delivered current.

At 2710, the processor determines a portion of the pulse generator to use based on the electrical load determined at 2705. For example, if the impedance of the electrical load is greater than a threshold, the processor may determine that a first portion of the pulse generator will be used, and that a second portion of the pulse generator will not be used. In some embodiments, the first portion of the pulse generator is selected for use based on its current drive capability being sufficient for the electrical load.

At 2720, the processor generates a pulse with the portion of the pulse generator system determined at 2710. For example, the processor may operate switches to connect the selected portion to one or more drivers, and subsequently deliver a signal to the one or more drivers. If the selected portion is operational, the delivered signal causes the selected portion to generate a pulse, for example, as discussed above. Alternatively, the processor may select one or more drivers associated with the selected portion, and subsequently deliver a signal to the one or more drivers. If the selected portion is operational, the delivered signal causes the selected portion to generate a pulse, for example, as discussed above.

It may be desirable to treat a patient with multiple voltages. In some embodiments, treating a patient with multiple voltages may be accomplished by using a first portion of the pulse generator to apply pulses of a first voltage and using a second portion of the pulse generator to apply pulses of a second voltage.

For example, pulse generator 1800, described above with reference to the FIG. 18, may be modified such that the DC positive (+) and negative (−) input ports of pulse generator circuits 1810, 1820, 1830, and 1840 are not all connected to the first and second power supply input terminals V1 and V2. Instead, the DC positive (+) and negative (−) input ports of one or more of pulse generator circuits 1810, 1820, 1830, and 1840 may be connected to additional power supply input terminals (not shown). In such embodiments, the pulse generator circuits 1810, 1820, 1830, and 1840 which are connected to the first and second power supply input terminals V1 and V2 may be charged to a different charge voltage than the pulse generator circuits 1810, 1820, 1830, and 1840 which are connected to the additional power supply input terminals. As a result, when used to apply pulses to a patient, the pulse generator circuits 1810, 1820, 1830, and 1840 which are connected to the first and second power supply input terminals V1 and V2 apply a different voltage than the pulse generator circuits 1810, 1820, 1830, and 1840 which are connected to the additional power supply input terminals.

Pulse generators 1900, 2000, and 2200 of FIGS. 19, 20, and 22, respectively, may be similarly modified and used.

Figure 28:
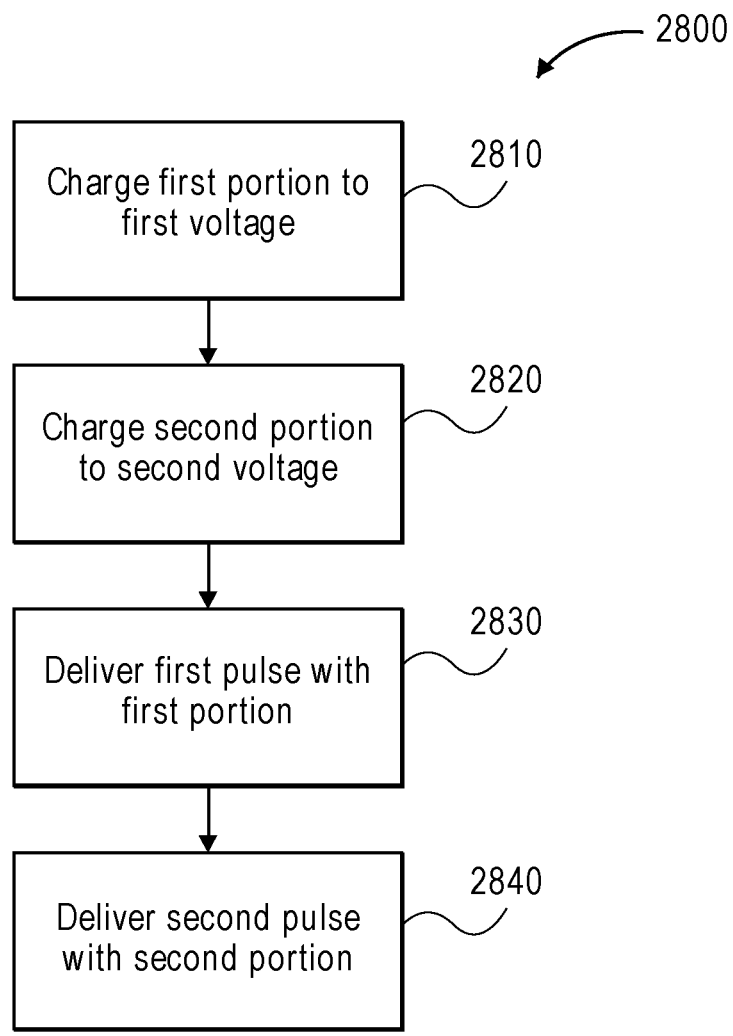
FIG. 28 is a flowchart illustrating a method of using a pulse generator system capable of delivering pulses of multiple voltage values.

FIG. 28 is a flowchart illustrating a method 2800 of using a pulse generator system capable of delivering pulses of multiple voltage values, such as any of the modified pulse generators 1800, 1900, 2000, and 2200 of FIGS. 18, 19, 20, and 22, respectively. The method 2800 may, for example, be performed as part of treating a patient.

At 2810, a processor charges a first portion of the pulse generator to a first charge voltage.

At 2820, the processor charges a second portion of the pulse generator to a second charge voltage. The second charge voltage may, for example, be different from the first charge voltage.

At 2830, the processor generates a first pulse with the first portion of the pulse generator system and delivers the generated pulse to a patient. For example, the processor may operate switches to connect the selected portion to one or more drivers, and subsequently deliver a signal to the one or more drivers. If the selected portion is operational, the delivered signal causes the selected portion to generate a pulse, for example, as discussed above. Alternatively, the processor may select one or more drivers associated with the selected portion, and subsequently deliver a signal to the one or more drivers. If the selected portion is operational, the delivered signal causes the selected portion to generate a pulse, for example, as discussed above.

At 2840, the processor generates a second pulse with the second portion of the pulse generator system and delivers the generated pulse to the patient. For example, the processor may operate switches to connect the selected portion to one or more drivers, and subsequently deliver a signal to the one or more drivers. If the selected portion is operational, the delivered signal causes the selected portion to generate a pulse, for example, as discussed above. Alternatively, the processor may select one or more drivers associated with the selected portion, and subsequently deliver a signal to the one or more drivers. If the selected portion is operational, the delivered signal causes the selected portion to generate a pulse, for example, as discussed above.

In some embodiments, the processor is configured to alternately deliver pulses to the patient with the first and second portions of the pulse generator system. In some embodiments, the processor is configured to deliver a first number of pulses to the patient with the first portion of the pulse generator system, and subsequently deliver a second number of pulses to the patient with the second portion of the pulse generator system.

In some embodiments, while the processor delivers one or more pulses to the patient using the first portion of the pulse generator system, the processor also causes the second portion of the pulse generator system to be charged, for example, to the second charge voltage. In addition, while the processor delivers one or more pulses to the patient using the second portion of the pulse generator system, the processor may also cause the first portion of the pulse generator system to be charged, for example, to the first charge voltage.

In some embodiments, one or more of the methods discussed herein may performed with a test load which is not a patient. For example, a test load, which may include one or more resistors, one or more capacitors, and/or one or more inductors, may be used. As a part of one or more of the methods, a pulse may be delivered to the test load. In some embodiments, the test load may be plugged into a housing of a system, such as a NsPEF system. In some embodiments, the test load may be plugged into a cable connected to a housing of a NsPEF system. In some embodiments, the test load may be connected to an electrode of a NsPEF system. In some embodiments, the test load is included in the NsPEF system, and is selectively connected to a pulse generator by one or more switches, for example, by one or more relays.

As used herein the term "patient" includes a subject, such as a test subject.

Applying nsPEF to a tumor sufficient to stimulate apoptosis may include at least the electrical characteristics found experimentally. For example, a 100 ns long pulse with a 20 ns rise time to 30 kV/cm (kilovolts per centimeter) at 1 to 7 pulses per second (pps) for 500 to 2000 pulses has been found to be sufficient to stimulate apoptosis, depending on the tumor type. Pulsed electric fields of at least 20 kV/cm have been shown to be effective. A number of pulses greater than 50 pulses has also been shown to be effective. Current values between 12 A and 60 A resulted, depending on the electrode type and skin resistance.

The embodiments of pulse generators described herein have many uses. Cancer that has metastasized through a subject's bloodstream may be treated using nsPEF's immune stimulation properties. For treatment, circulating tumor cells (CTCs) are isolated from the bloodstream and amassed in vial, test tube, or other suitable in vitro environment. In some cases, there may only be a few (e.g., 5, 10), tumor cells that are collected and amassed. Through this mass, an nsPEF electric field is applied in order to treat the cells. This may cause calreticulin or one or more other damage-associated molecular patterns (DAMPs) to be expressed on the surface membranes of the tumor cells. The tumor cells may then be introduced back into the subject's bloodstream by injection, infusion, or otherwise.

In an alternative embodiment, single CTCs may also be isolated from the bloodstream, and each tumor cell treated individually. An automated system that captures CTCs in whole blood using iron nanoparticles coated with a polymer layer carrying biotin analogues and conjugated with antibodies for capturing CTCs can automatically capture the tumor cells, and a magnet and or centrifuge can separate them. After separation from the antibodies, the CTCs may be treated with nsPEF through a small capillary and then reintroduced to the patient's bloodstream.

Examples in the application may be used for treatments of human and murine subjects, the treatment of other animals is also contemplated. Agricultural animals, such as horses and cows, or racing animals, such as horses, may be treated. Companion animals, such as cats and dogs, may find special use with the treatments described herein. It may be difficult for a veterinarian to remove many tumors from a small animal, and cancers may be caught relatively late because the animals cannot communicate their advancing pain. Further, the risk inherent in reinjecting tumor cells—albeit treated tumor cells—may be worth the potential benefits of potentially halting a metastasized cancer in a loved pet.

The methods of the present invention can be used for the treatment of any type of cancer, whether characterized as malignant, benign, soft tissue, or solid, and cancers of all stages and grades including pre- and post-metastatic cancers. Examples of different types of cancer include, but are not limited to, digestive and gastrointestinal cancers such as gastric cancer (e.g., stomach cancer), colorectal cancer, gastrointestinal stromal tumors, gastrointestinal carcinoid tumors, colon cancer, rectal cancer, anal cancer, bile duct cancer, small intestine cancer, and esophageal cancer; breast cancer; lung cancer; gallbladder cancer; liver cancer; pancreatic cancer; appendix cancer; prostate cancer, ovarian cancer; renal cancer (e.g., renal cell carcinoma); cancer of the central nervous system; skin cancer (e.g., melanoma); lymphomas; gliomas; choriocarcinomas; head and neck cancers; osteogenic sarcomas; and blood cancers.

Electrical characteristics of nsPEF treatments can be adjusted based on a size and/or a type of a tumor. Types of tumors may include tumors of different regions of the body, such as the cancerous tumors described above.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

As noted previously, all measurements, dimensions, and materials provided herein within the specification or within the figures are by way of example only.

A recitation of "a," "an," or "the" is intended to mean "one or more" unless specifically indicated to the contrary. Reference to a "first" component does not necessarily require that a second component be provided. Moreover reference to a "first" or a "second" component does not limit the referenced component to a particular location unless expressly stated.

As used herein, the term "patient" includes a person, an animal, or a tissue sample to which pulses are applied. The pulses may be applied for the purpose of treatment or for the purpose of experiment.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

What is claimed is:

1. A method of delivering pulses to a subject using a pulse generation system, the method comprising:
   transmitting a driving signal pulse to any selected one or more of a plurality of pulse generator circuits, wherein the driving signal pulse is not transmitted to at least one of the plurality of pulse generator circuits;
   generating, by each of the selected one or more of the plurality of pulse generator circuits, at least a portion of an output voltage pulse in response to the driving signal pulse being transmitted thereto, wherein each generated the at least the portion of the output voltage pulse is combined into a single output voltage pulse at an output terminal of the pulse generation system and wherein the at least one of the plurality of pulse generator circuits that does not receive the driving signal pulse does not generate any portion of the single output voltage pulse; and
   delivering the single output voltage pulse to the subject.

2. The method of claim 1, further comprising:
   generating the driving signal pulse with a driver circuit; and
   selectively connecting any pulse generator circuit of the plurality of pulse generator circuits to the driver circuit using one or more switches controlled by a controller.

3. The method of claim 2, further comprising:
   cooperatively generating, by a plurality of stages in a first pulse generator circuit of the selected one or more of the plurality of pulse generator circuits, the at least the portion of the output voltage pulse in response to the driving signal pulse being transmitted from the driver circuit.

4. The method of claim 3, further comprising:
   receiving, by a stage driver in at least some of the selected one or more of the plurality of pulse generator circuits, the driving signal pulse from the driver circuit; and
   generating, by the stage driver, a signal pulse for the plurality of stages of the corresponding selected pulse generator circuit, wherein the cooperatively generating the at least the portion of the output voltage pulse is further in response to the plurality of stages in the corresponding pulse generator circuit receiving the signal pulse.

5. The method of claim 1, further comprising:
   transmitting, by a controller, an input pulse to any selected one or more of a plurality of driver circuits; and
   generating, by each of the selected one or more of the plurality of driver circuits, a driving signal pulse for one of the selected one or more of the plurality of pulse generator circuits in response to receiving the input pulse.

6. The method of claim 5, further comprising:
   cooperatively generating, by a plurality of pulse generator stages of a first pulse generator circuit of the selected one or more of the plurality of pulse generator circuits, the at least the portion of the output voltage pulse in response to the driving signal pulse being transmitted from the corresponding driver circuit.

7. The method of claim 6, further comprising:
   generating, by a pulse generator stage driver of the first pulse generator circuit, a signal pulse in response to receiving the driving signal pulse from the corresponding driver circuit; and
   transmitting the signal pulse to the plurality of pulse generator stages, wherein the cooperatively generating the at least the portion of the output voltage pulse is further in response to the plurality of pulse generator stages receiving the signal pulse.

8. The method of claim 6, further comprising:
   generating, by each of a plurality of pulse generator stage drivers, a signal pulse in response to receiving the driving signal pulse from the corresponding driver circuit, wherein each of the pulse generator stage drivers is connected to one of the plurality of pulse generator stages; and
   transmitting the signal pulse to the corresponding pulse generator stage, wherein the cooperatively generating the at least the portion of the output voltage pulse is further in response to the plurality of pulse generator stages receiving the signal pulse.

9. The method of claim 8, further comprising:
   generating, by each of a plurality of switch drivers, a pulse that controls one of a plurality of serially connected switches in a first pulse generator stage of the plurality of pulse generator stages, wherein the cooperatively generating the at least the portion of the output voltage pulse is further in response to the pulses generated by the switch drivers.

10. The method of claim 1, wherein the selected one or more of the plurality of pulse generator circuits comprises a first selected pulse generator circuit, and wherein the first selected pulse generator circuit generates a first output voltage pulse, the method comprising:
    transmitting an input signal pulse to a driver circuit;
    receiving, by a controller, a first indication of a current or a voltage of the first output voltage pulse; and
    determining, by the controller, whether the first selected pulse generator circuit is operational based on the first indication.

11. The method of claim 10, further comprising:
    recording whether the first selected pulse generator circuit is operational in a memory;
    transmitting a second input signal to the driver circuit;
    in response to receiving the second input signal, transmitting, by the driver circuit, a second driving signal to a second selected pulse generator circuit of the plurality of pulse generator circuits;
    in response to receiving the second driving signal, generating, by the second selected pulse generator circuit, a second output voltage pulse;
    receiving, by the controller, a second indication of a current or a voltage of the second output voltage pulse;
    determining, by the controller, whether the second selected pulse generator circuit is operational based on the second indication;
    recording whether the second selected pulse generator circuit is operational in the memory; and
    transmitting input signals for driving one or more pulse generator circuits that are determined to be operational.

12. The method of claim 10, further comprising:
    transmitting a second input signal to the driver circuit;
    in response to receiving the second input signal, transmitting, by the driver circuit, a second driving signal to a second selected pulse generator circuit of the plurality of pulse generator circuits; and
    in response to receiving the second driving signal, generating, by the second selected pulse generator circuit, a second output voltage pulse, wherein the first output voltage pulse and the second output voltage pulse have different voltages.

13. The method of claim 10, further comprising:
determining whether each of the selected one or more of the plurality of pulse generator circuits is operational; and
taking a corrective action for each of the pulse generator circuits of the pulse generation system determined to be not operational.

14. The method of claim 10, further comprising:
connecting an electrode to a load;
delivering a pulse from the pulse generation system to the load via the electrode; and
determining a value for the load, wherein the selected first pulse generator circuit is selected based at least in part on the value of the load.

15. The method of claim 10, further comprising:
generating a digital output representing a temperature at an electrode receiving the single output voltage pulse.

16. The method of claim 10, wherein the first indication is a voltage, the method further comprising:
comparing the first indication with a threshold voltage to determine whether the first selected pulse generator circuit is operational.

17. The method of claim 10, wherein the first indication is a current, the method further comprising:
comparing the first indication with a threshold current to determine whether the first selected pulse generator circuit is operational.

18. The method of claim 1, the method comprising:
receiving, by a controller, an impedance value at the output terminal of the pulse generation system; and
selecting, by the controller, a first subset of the plurality of pulse generator circuits based at least in part on the impedance value.

19. The method of claim 18, wherein selecting the first subset of the plurality of pulse generator circuits is further based at least in part on current drive capability of the first subset of the plurality of pulse generator circuits.

20. The method of claim 1, further comprising:
measuring at least one of a current or a voltage of the single output voltage pulse delivered to the subject.

21. The method of claim 1, further comprising:
generating a series of single output voltage pulses, wherein the generating comprises repeating: 1) the transmitting the driving signal pulse and 2) the generating, by each selected one or more of the plurality of pulse generator circuits, the at least the portion of the output voltage pulse in response to the driving signal pulse being transmitted thereto.

22. The method of claim 1, wherein at least some of the plurality of pulse generator circuits comprise first and second circuit output terminals with differing polarities.

23. The method of claim 1,
wherein the delivering the single output voltage pulse to the subject comprises delivering the single output voltage pulse via an electrode.

24. The method of claim 23, wherein the electrode comprises at least two electrodes having differing polarities.

25. The method of claim 23, further comprising:
receiving feedback from the electrode;
selecting a new one or more of the plurality of pulse generator circuits based at least in part on the feedback; and
transmitting the driving signal pulse to the new one or more of the plurality of pulse generator circuits.

26. A method of operating a pulse generation system, the method comprising:
transmitting a driving signal pulse to any selected one or more of a plurality of pulse generator circuits, wherein the driving signal pulse is not transmitted to at least one of the plurality of pulse generator circuits;
generating, by each of the selected one or more of the plurality of pulse generator circuits, at least a portion of an output voltage pulse in response to the driving signal pulse being transmitted thereto, wherein each generated the at least the portion of the output voltage pulse is combined into a single output voltage pulse at an output terminal of the pulse generation system and wherein the at least one of the plurality of pulse generator circuits that does not receive the driving signal pulse does not generate any portion of the single output voltage pulse; and
delivering the single output voltage pulse to a load via an electrode, wherein the electrode comprises a plurality of electrode terminals.

27. The method of claim 26, the method comprises determining an impedance value of the load.

28. The method of claim 26, the method comprises delivering a series of the single output voltage pulse to the load, wherein the load is a test subject.

* * * * *